US010858637B2

(12) United States Patent
Jensen et al.

(10) Patent No.: US 10,858,637 B2
(45) Date of Patent: Dec. 8, 2020

(54) POLYPEPTIDES WITH LIPASE ACTIVITY AND POLYNUCLEOTIDES ENCODING SAME

(71) Applicant: NOVOZYMES A/S, Bagsvaerd (DK)

(72) Inventors: Kenneth Jensen, Oelsted (DK); Maria Louise Leth, Kbh V (DK); Anna Verena Reiser, København Ø (DK); Robert Piotr Olinski, Værløse (DK); Preben Nielsen, Hørsholm (DK); Lone Baunsgaard, Helsingør (DK)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 15/579,697

(22) PCT Filed: Jun. 13, 2016

(86) PCT No.: PCT/EP2016/063495
§ 371 (c)(1),
(2) Date: Dec. 5, 2017

(87) PCT Pub. No.: WO2016/202739
PCT Pub. Date: Dec. 22, 2016

(65) Prior Publication Data
US 2018/0171313 A1 Jun. 21, 2018

(30) Foreign Application Priority Data

Jun. 16, 2015 (EP) .................... 15172368

(51) Int. Cl.
*C11D 3/386* (2006.01)
*C12N 9/20* (2006.01)
*C11D 1/83* (2006.01)
*C11D 1/14* (2006.01)
*C11D 1/22* (2006.01)
*C11D 1/72* (2006.01)

(52) U.S. Cl.
CPC ................ *C12N 9/20* (2013.01); *C11D 1/83* (2013.01); *C11D 3/38627* (2013.01); *C12Y 301/01* (2013.01); *C11D 1/146* (2013.01); *C11D 1/22* (2013.01); *C11D 1/72* (2013.01)

(58) Field of Classification Search
None
See application file for complete search history.

(56) References Cited

U.S. PATENT DOCUMENTS

| 6,624,129 B1* | 9/2003 | Borch | ............... C11D 1/83 435/196 |
|---|---|---|---|
| 2008/0305531 A1 | 12/2008 | Lam | |
| 2015/0031111 A1 | 1/2015 | SKold-Joergensen et al. | |

OTHER PUBLICATIONS

Anonymous, 2015, NCBI accession No. WP_050657910.1.
Anonymous, 2015, NCBI accession No. WP_050657911.1.
Lai et al, 2012, J Bacteriol 194(24), 6937.
Lai et al, 2012, UniProt accession No. K2JK28.
Lai et al, 2012, UniProt accession No. K2JZA4.
Lucas et al, 2008, EBI accession No. FE810235.
Madan et al, 2009, Appl Microbiol Biotechnol 85(3), 597-604.
Martini et al, 2014, Micro Cell Fac 13(1), 171.
Martini et al, 2015, EBI accession No. KM023399.
Rosenau et al, 2004, Chembiochem 5(2), 152-161.
US 2008-0305531—XP002760601, EBI Accession No. AQZ64688, May 2010.
Anonymous, 2013, NCBI Reference sequence WP_008483634.1.
Lai et al, 2012, Genbank No. EKE75648.1.
Su et al, 2014, Food and oil, vol. 27, No. 6, pp. 1-4—Incl EnAb.

* cited by examiner

*Primary Examiner* — David Steadman
(74) *Attorney, Agent, or Firm* — Elias Lambiris

(57) ABSTRACT

The present invention relates to isolated polypeptides with lipase activity. The invention also relates to polynucleotides encoding the polypeptides; nucleic acid constructs, vectors, and host cells comprising the polynucleotides; compositions comprising the polynucleotides and methods of using the polypeptides or the compositions.

15 Claims, 1 Drawing Sheet
Specification includes a Sequence Listing.

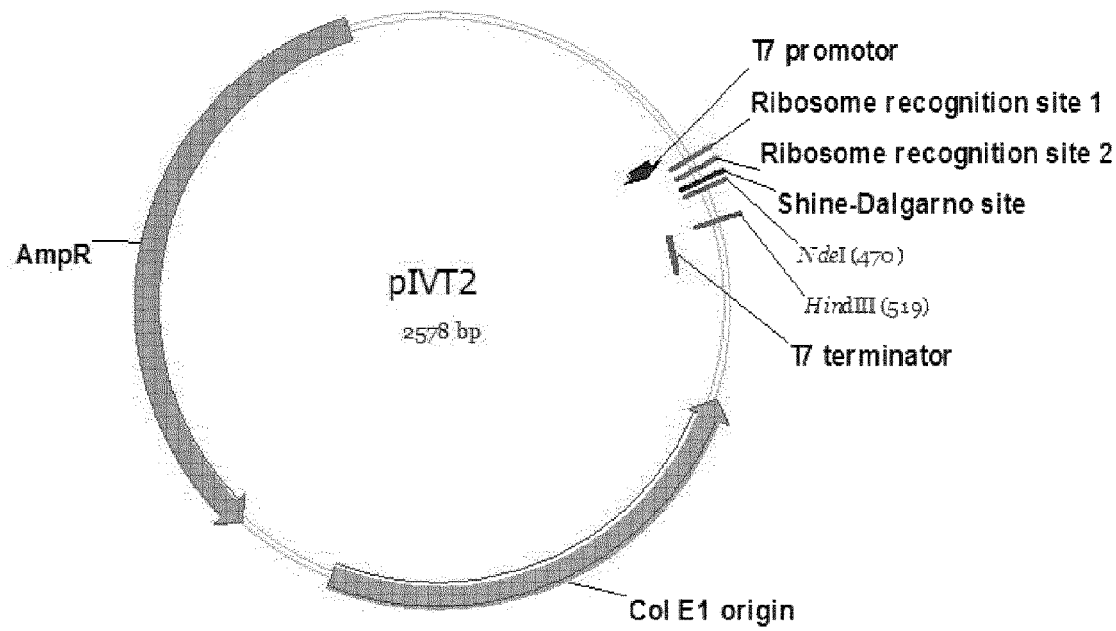
Figure 1: Plasmid map of pIVT2
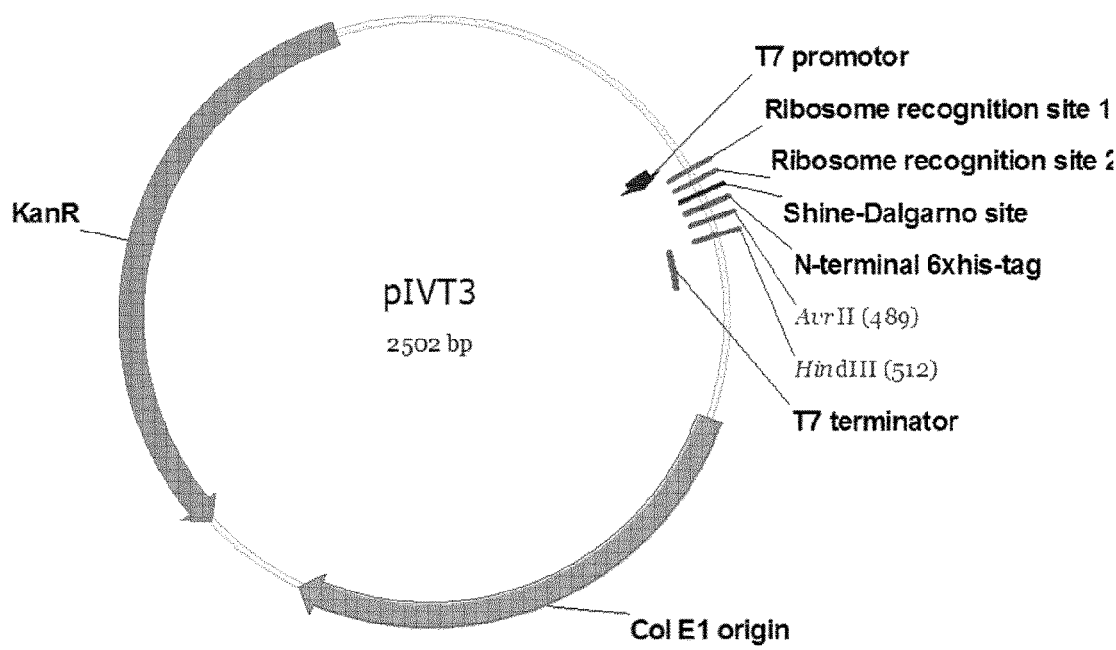
Figure 2: Plasmid map of pIVT3

POLYPEPTIDES WITH LIPASE ACTIVITY AND POLYNUCLEOTIDES ENCODING SAME

CROSS-REFERENCE TO RELATED APPLICATIONS

This application is a 35 U.S.C. 371 national application of PCT/EP2016/063495 filed Jun. 13, 2016, which claims priority or the benefit under 35 U.S.C. 119 of European application no. 15172368.1 filed Jun. 16, 2015, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides with lipase activity, polynucleotides encoding the polypeptides, methods of producing the polypeptides, and methods of using the polypeptides.

Description of the Related Art

Lipases are important biocatalysts which have shown to be useful for various applications and a large number of different lipases have been identified and many commercialized.

Lipases have been employed in compositions for the removal of lipid stains by hydrolyzing triglycerides to generate fatty acids. Current cleaning and/or fabric care compositions comprise many active ingredients which are interfering with the ability of lipases to remove lipid stains. Thus, the need exists for lipases that can function in the harsh environment of compositions used for cleaning. It is the object of the present application to provide lipases that has advantageous characteristics, such as improved performance when applied in cleaning compositions.

Extracellular lipases from a number of bacterial species require the assistance of specific steric chaperones. The lipase is dependent on the chaperone in order to fold into an enzymatically active conformation.

Such chaperones can bind their substrate lipases with high affinity to form 1:1 complexes in vitro, which are stable enough to allow copurification and co-immunoprecipitation of both proteins. These complexes have to be dissolved to release the activated lipase after completion of the folding process.

The genes encoding a lipase and its chaperone protein are usually encoded within an operon; this indicates that each chaperone protein interacts specifically with its cognate lipase.

A known lipase from *Gallaecimonas xiamenensis* (uniprot:K2JZA4) is 84% identical to the mature polypeptide of SEQ ID NO: 2 of the present application. The chaperone protein (uniprot:K2JK28) of the same *G. xiamenensis* lipase is 55% identical to the mature polypeptide of SEQ ID NO: 3 of the present application. The two *G. xiamenensis* sequences are disclosed by Qiliang Lai, et al., J. Bacteriol. December 2012 vol. 194 no. 24, page 6937 and shown in SEQ ID NO: 20 and SEQ ID NO: 21 of the present application.

SUMMARY OF THE INVENTION

In a screening on an agar plate supplemented with olive oil a strain of the Gram-negative bacteria *Gallaecimonas pentaromativorans* was found to be positive for triglyceride degradation. A lipase was identified encoded in the same operon with its chaperone protein.

The present invention thus relates to isolated polypeptides with lipase activity as well as to isolated polypeptides having the ability to function as a chaperone to the polypeptide having lipase activity.

Accordingly, the present invention relates in a first aspect to isolated polypeptides with lipase activity, selected from the group consisting of:
  (a) a polypeptide having at least 85% sequence identity to the mature polypeptide of SEQ ID NO: 2;
  (b) a polypeptide encoded by a polynucleotide that hybridizes under high stringency conditions with (i) nucleic acids 70 to 927 of SEQ ID NO: 1 or the full-length complement of (i);
  (c) a polypeptide encoded by a polynucleotide having at least 85% sequence identity to the mature lipase polypeptide coding sequence of SEQ ID NO: 1;
  (d) a polypeptide which is a variant of SEQ ID NO: 2 comprising a substitution and/or deletion and/or insertion, wherein the variant has lipase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41 or 42 positions; and
  (e) a polypeptide which is a fragment of any of the polypeptides of (a), (b), (c) or (d), wherein the fragment has lipase activity and comprises at least 200 amino acids.

In a second aspect the present invention relates to isolated polypeptides having the ability to function as a chaperone to the polypeptides of the first aspect, selected from the group consisting of:
  (a) a polypeptide having at least 60% sequence identity to the mature polypeptide of SEQ ID NO: 3;
  (b) a polypeptide encoded by a polynucleotide that hybridizes under medium-high stringency conditions with (i) nucleic acids 971 to 1786 of SEQ ID NO: 1 or the full-length complement of (i);
  (c) a polypeptide encoded by a polynucleotide having at least 60% sequence identity to the mature chaperone polypeptide coding sequence of SEQ ID NO: 1;
  (d) a polypeptide which is a variant of SEQ ID NO: 3 comprising a substitution and/or deletion and/or insertion, wherein the variant comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions; and
  (e) a polypeptide which is a fragment of any of the polypeptides of (a), (b), (c) or (d) and has at least 90% of the length of the mature polypeptide.

In a third aspect the present invention relates to compositions comprising the polypeptide with lipase activity according to the first aspect and optionally the polypeptide having the ability to function as a chaperone according to the second aspect.

The present invention also relates to methods for hydrolyzing a lipid, methods for cleaning an object, isolated polynucleotides encoding the polypeptide of the first or second aspect; nucleic acid constructs, vectors, and host cells comprising the polynucleotides; and methods of producing the polypeptides.

Overview of Sequence Listing

The present invention relates to a set of sequences. For ease, these are listed below;

SEQ ID NO: 1 is the DNA sequence of the polycistronic operon as isolated from *Gallaecimonas pentaromativorans*.

SEQ ID NO: 2 is the amino acid sequence of the lipase as deduced from SEQ ID NO: 1.

SEQ ID NO: 3 is the amino acid sequence of the chaperone as deduced from SEQ ID NO: 1.

SEQ ID NO: 4 is the codon optimized DNA sequence encoding the lipase of SEQ ID NO: 2.

SEQ ID NO: 5 is the codon optimized DNA sequence encoding the chaperone of SEQ ID NO: 3.

SEQ ID NO: 6 is the DNA sequence encoding the *E. coli* maltose binding protein.

SEQ ID NO: 7 is the amino acid sequence of the *E. coli* maltose binding protein.

SEQ ID NO: 8 is the DNA sequence encoding the chaperone fusion protein (Chap-MBP).

SEQ ID NO: 9 is the amino acid sequence of the chaperone protein.

SEQ ID NO: 10 to SEQ ID NO: 19 are various primers and linkers.

SEQ ID NO: 20 is the *Gallaecimonas xiamenensis* lipase (uniprot:K2JZA4).

SEQ ID NO: 21 is the chaperone protein of the *G. xiamenensis* lipase (uniprot:K2JK28).

BRIEF DESCRIPTION OF THE DRAWING FIGURES

FIG. 1 shows plasmid map of pIVT2.
FIG. 2 shows plasmid map of pIVT3.

DEFINITIONS

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Chaperones: Chaperones are proteins that assist the folding or unfolding of other proteins. Most newly synthesized proteins can fold in absence of chaperones; however, the lipase of the present invention requires a chaperone for correct folding.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide having one or more (e.g., several) amino acids absent from the amino (N-) and/or carboxyl (C-) terminus of the mature polypeptide; wherein the fragment has lipase activity. In one aspect, the fragment contains at least 200, at least 225, at least 250, at least 275, or even at least 280 amino acids—such as 281, 282, 283, or 284 amino acids. In one aspect, the fragment comprises at least 50%, at least 55%, at least 60%, at least 65%, at least 70%, at least 80%, at least 85%, at least 90%, or at least 95% of the length of the mature polypeptide (i.e. amino acids 1 to 285) of SEQ ID NO: 2.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, polypeptide, variant, nucleic acid, protein, peptide or cofactor, that is at least partially removed from one or more (e.g., several) or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Lipase: The terms "lipase", "lipase enzyme", "lipolytic enzyme", "lipid esterase", "lipolytic polypeptide", and "lipolytic protein" refers to an enzyme in class EC 3.1,1 as defined by Enzyme Nomenclature. It may have lipase activity (triacylglycerol lipase, EC 3.1.1.3), cutinase activity (EC 3.1.1.74), sterol esterase activity (EC 3.1.1.13) and/or wax-ester hydrolase activity (EC 3.1.1.50). For purposes of the present invention, lipase activity is activity of the refolded lipase and determined according to the procedure described in the Examples section (Lipase assay: Hydrolytic activity on fatty acids pNP esters). In one aspect, the polypeptides of the present invention have at least 20%, e.g., at least 25%, at least 30%, at least 35%, at least 40%, at least 45%, at least 50%, at least 55%, at least 60%, at least 65%, at least 70%, at least 80%, at least 85%, at least 90%, at least 95%, or at least 100% of the lipase activity of the polypeptide of SEQ ID NO: 2.

Low temperature: "Low temperature" is a temperature of 5-35° C., such as 5-30° C., 5-25° C., 5-20° C., 5-15° C., or 5-10° C. In another embodiment, "Low temperature" is a temperature of 10-35° C., such as 10-30° C., 10-25° C., 10-20° C., or 10-15° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide having lipase activity is amino acids 1 to 285 of SEQ ID NO: 2. In one aspect, the mature polypeptide having the ability to function as a chaperone to the lipase is amino acids 1 to 271 of SEQ ID NO: 3.

Mature polypeptide coding sequence: The term "mature polypeptide coding sequence" means a polynucleotide that encodes a mature polypeptide having lipase activity and/or a polynucleotide that encodes a mature polypeptide having the ability to function as a chaperone to the lipase. In one aspect, the mature polypeptide coding sequence of the lipase is nucleotides 70 to 927 of SEQ ID NO: 1. Nucleotides 1 to 69 of SEQ ID NO: 1 encodes a signal peptide.

In one aspect, the mature polypeptide coding sequence of the polypeptide having the ability to function as a chaperone to the lipase is nucleotides 971 to 1786 of SEQ ID NO: 1. Nucleotides 929 to 970 of SEQ ID NO: 1 encode a signal peptide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent lipase: The term "parent" or "parent lipase" means a lipase to which a substitution is made to produce the lipase variants of the present invention. The parent may be a naturally occurring (wild-type) polypeptide or a variant or fragment thereof.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol*. 48: 443-453) as implemented in the Needle program of the EMBOSS package (EMBOSS: The European Molecular Biology Open Software Suite, Rice et al., 2000, *Trends Genet*. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the nobrief option) is used as the percent identity and is calculated as follows:

(Identical Residues×100)/(Length of Alignment Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the nobrief option) is used as the percent identity and is calculated as follows:

(Identical Deoxyribonucleotides×100)/(Length of Alignment Total Number of Gaps in Alignment)

Stringency conditions: Very low stringency conditions: The term "very low stringency conditions" means for probes of at least 100 nucleotides in length, prehybridization and hybridization at 42° C. in 5×SSPE, 0.3% SDS, 200 micrograms/mL sheared and denatured salmon sperm DNA, and 25% formamide, following standard Southern blotting procedures for 12 to 24 hours. The carrier material is finally washed three times each for 15 minutes using 2×SSC, 0.2% SDS at 45° C. Low stringency conditions: The term "low stringency conditions" means for probes of at least 100 nucleotides in length, prehybridization and hybridization at 42° C. in 5×SSPE, 0.3% SDS, 200 micrograms/mL sheared and denatured salmon sperm DNA, and 25% formamide, following standard Southern blotting procedures for 12 to 24 hours. The carrier material is finally washed three times each for 15 minutes using 2×SSC, 0.2% SDS at 50° C. Medium stringency conditions: The term "medium stringency conditions" means for probes of at least 100 nucleotides in length, prehybridization and hybridization at 42° C. in 5×SSPE, 0.3% SDS, 200 micrograms/mL sheared and denatured salmon sperm DNA, and 35% formamide, following standard Southern blotting procedures for 12 to 24 hours. The carrier material is finally washed three times each for 15 minutes using 2×SSC, 0.2% SDS at 55° C. Medium-high stringency conditions: The term "medium-high stringency conditions" means for probes of at least 100 nucleotides in length, prehybridization and hybridization at 42° C. in 5×SSPE, 0.3% SDS, 200 micrograms/mL sheared and denatured salmon sperm DNA, and either 35% formamide, following standard Southern blotting procedures for 12 to 24 hours. The carrier material is finally washed three times each for 15 minutes using 2×SSC, 0.2% SDS at 60° C. High stringency conditions: The term "high stringency conditions" means for probes of at least 100 nucleotides in length, prehybridization and hybridization at 42° C. in 5×SSPE, 0.3% SDS, 200 micrograms/mL sheared and denatured salmon sperm DNA, and 50% formamide, following standard Southern blotting procedures for 12 to 24 hours. The carrier material is finally washed three times each for 15 minutes using 2×SSC, 0.2% SDS at 65° C. Very high stringency conditions: The term "very high stringency conditions" means for probes of at least 100 nucleotides in length, prehybridization and hybridization at 42° C. in 5×SSPE, 0.3% SDS, 200 micrograms/mL sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Subsequence: The term "subsequence" means a polynucleotide having one or more (e.g., several) nucleotides absent from the 5' and/or 3' end of a mature polypeptide coding sequence; wherein the subsequence encodes a fragment having lipase activity.

In one aspect, the subsequence contains at least 600, at least 675, at least 750, at least 825, or even at least 840 amino acids—such as 843, 846, 849, or 852 nucleotides.

In one aspect, a subsequence contains at least 50%, at least 55%, at least 60%, at least 65%, at least 70%, at least 80%, at least 85%, at least 90%, and at least 95% of the number of nucleotides of 70 to 927 of SEQ ID NO: 1.

Variant: The term "variant" means a polypeptide having lipase activity comprising a substitution at one or more (e.g., several) positions i.e. a variant of the present invention is also a polypeptide of the present invention. A substitution means a replacement of an amino acid occupying a position with a different amino acid; a deletion means removal of an amino acid occupying a position; and an insertion means adding 1-3 amino acids adjacent to an amino acid occupying a position. In one aspect, the variants of the present invention have at least 20%, e.g., at least 40%, at least 50%, at least 60%, at least 70%, at least 80%, at least 90%, at least 95%, or at least 100% of the lipase activity of SEQ ID NO: 2. In one aspect, lipase activity is measured according to the Lipase assay: Hydrolytic activity on fatty acids pNP esters as described herein.

Wash performance: In the present context the term "wash performance" is used as an enzyme's ability to remove lipid or lipid-containing stains present on the object to be cleaned. The wash performance may be quantified by calculating the so-called G/(B+R) value defined in the description of AMSA in the Methods section below. The term "wash performance" includes cleaning in general e.g. hard surface cleaning as in dish wash, but also wash performance on textiles such as laundry, and also industrial and institutional cleaning.

Wild-type lipase: The term "wild-type" lipase means a lipase expressed by a naturally occurring microorganism, such as a bacterium, yeast, or filamentous fungus found in nature. A "wild-type" lipase may be recombinantly expressed in a host cell.

DETAILED DESCRIPTION OF THE INVENTION

Polypeptides with Lipase Activity

In an embodiment, the present invention relates to isolated polypeptides with lipase activity, selected from the group consisting of:

(a) a polypeptide having at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2;

(b) a polypeptide encoded by a polynucleotide that hybridizes under low stringency conditions, medium stringency conditions, medium-high stringency conditions, high stringency conditions, or very high stringency conditions with (i) nucleic acids 70 to 927 of SEQ ID NO: 1, or the full-length complement of (i);

(c) a polypeptide encoded by a polynucleotide having at least 85%, at least 90%, at least 91%, at least 92%, at least 93%, at least 94%, at least 95%, at least 96%, at least 97%, at least 98%, at least 99%, or 100% sequence identity to the mature lipase polypeptide coding sequence of SEQ ID NO: 1;

(d) a polypeptide which is a variant of SEQ ID NO: 2 comprising a substitution, deletion, and/or insertion at one or more (e.g. several) positions; and (e) a polypeptide which is a fragment of any of the polypeptides of (a), (b), (c) or (d). In a particular embodiment the invention relates to polypeptides having a sequence identity to the mature polypeptide of SEQ ID NO: 2 of at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the lipase activity of the mature polypeptide of SEQ ID NO: 2.

In a particular embodiment the invention relates to polypeptides having a sequence identity to the mature polypeptide of SEQ ID NO: 2 of at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the lipase activity of the mature polypeptide of SEQ ID NO: 2.

In a particular embodiment the invention relates to polypeptides having a sequence identity to the mature polypeptide of SEQ ID NO: 2 of at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the lipase activity of the mature polypeptide of SEQ ID NO: 2.

In a particular embodiment the invention relates to polypeptides having a sequence identity to the mature polypeptide of SEQ ID NO: 2 of at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the lipase activity of the mature polypeptide of SEQ ID NO: 2.

In a particular embodiment the invention relates to polypeptides having a sequence identity to the mature polypeptide of SEQ ID NO: 2 of at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the lipase activity of the mature polypeptide of SEQ ID NO: 2.

In a particular embodiment the invention relates to polypeptides having a sequence identity to the mature polypeptide of SEQ ID NO: 2 of at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the lipase activity of the mature polypeptide of SEQ ID NO: 2.

In a particular embodiment the invention relates to polypeptides having a sequence identity to the mature polypeptide of SEQ ID NO: 2 of at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the lipase activity of the mature polypeptide of SEQ ID NO: 2.

A polypeptide of the present invention preferably comprises or consists of the amino acid sequence of SEQ ID NO: 2 or an allelic variant thereof; or is a fragment thereof having lipase activity. In another aspect, the polypeptide comprises or consists of the mature polypeptide of SEQ ID NO: 2. A polypeptide of the present invention preferably comprises or consists of amino acids 1 to 285 of SEQ ID NO: 2.

In another embodiment, the present invention relates to an isolated polypeptide having lipase activity encoded by a polynucleotide that hybridizes under very low stringency conditions, low stringency conditions, medium stringency conditions, medium-high stringency conditions, high stringency conditions, or very high stringency conditions with (i) the mature lipase polypeptide coding sequence of SEQ ID NO: 1 or of SEQ ID NO: 3, or the full-length complement of (i) (Sambrook et al., 1989, Molecular Cloning, A Laboratory Manual, 2d edition, Cold Spring Harbor, N.Y.).

In another aspect, the polypeptide is a fragment of the polypeptide of SEQ ID NO: 2. The fragment may contain at least 250 amino acid residues, e.g., at least 255, at least 260, at least 265, at least 270, at least 275, or at least 280 amino acid residues. In one aspect, the fragment contains at least 50%, at least 55%, at least 60%, at least 65%, at least 70%, at least 75%, at least 80%, at least 85%, at least 90%, or at least 95% of the length of the mature polypeptide (i.e. amino acids 1 to 285) of SEQ ID NO: 2.

The polynucleotide of positions 70 to 927 of SEQ ID NO: 1 or a subsequence thereof, as well as the polypeptide of SEQ ID NO: 2 or a fragment thereof may be used to design nucleic acid probes to identify and clone DNA encoding polypeptides having lipase activity from strains of different genera or species according to methods well known in the art.

Similarly, the polynucleotide of positions 971 to 1786 of SEQ ID NO: 1 or a subsequence thereof, as well as the polypeptide of SEQ ID NO: 3 or a fragment thereof may be used to design nucleic acid probes to identify and clone DNA encoding polypeptides having the ability to function as a chaperone to the polypeptides having lipase activity.

Such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having lipase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleic acid probe corresponding to (i) nucleic acids 70 to 927 or nucleic acids 971 to 1786 of SEQ ID NO: 1; (ii) any of the mature lipase polypeptide coding sequences of SEQ ID NO: 1; (iii) a full-length complement thereof; or (iv) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is SEQ ID NO: 1. In another aspect, the nucleic acid probe consists of at least 15 and up to 1000 nucleotides of SEQ ID NO: 1. In another aspect, the nucleic acid probe is a polynucleotide that encodes the polypeptide of SEQ ID NO: 2; or a fragment thereof. In yet another aspect, the nucleic acid probe is a polynucleotide that encodes the polypeptide of SEQ ID NO: 3; or a fragment thereof.

In another embodiment, the present invention relates to an isolated polypeptide having lipase activity encoded by a polynucleotide having a sequence identity to the mature lipase polypeptide coding sequence of SEQ ID NO: 1 of at least 85%, at least 90%, at least 91%, at least 92%, at least 93%, at least 94%, at least 95%, at least 96%, at least 97%, at least 98%, at least 99%, or 100%.

In another embodiment, the present invention relates to an isolated polypeptide having the ability to function as a chaperone to the polypeptide of SEQ ID NO: 2, the isolated polypeptide selected from the group consisting of:

(a) a polypeptide having at least 60%, at least 65%, at least 70%, at least 75%, at least at least 80%, at least 85%, at least 86%, at least 86%, at least 87%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 3;

(b) a polypeptide encoded by a polynucleotide that hybridizes under low stringency conditions, medium stringency conditions, medium-high stringency conditions, high stringency conditions, or very high stringency conditions with (i) nucleic acids 971 to 1786 of SEQ ID NO: 1 or the full-length complement of (i);

(c) a polypeptide encoded by a polynucleotide having at least 60%, at least 65%, at least 70%, at least 75%, at least at least 80%, at least 85%, at least 86%, at least 86%, at least 87%, at least 89%, at least 90%, at least 91%, at least 92%, at least 93%, at least 94%, at least 95%, at least 96%, at least 97%, at least 98%, at least 99%, or 100% sequence identity to the mature chaperone polypeptide coding sequence of SEQ ID NO: 1;

(d) a polypeptide which is a variant of SEQ ID NO: 3 comprising a substitution, deletion, and/or insertion at one or more (e.g. several) positions; and (e) a polypeptide which is a fragment of any of the polypeptides of (a), (b), (c) or (d).

In another embodiment, the present invention relates to variants of the lipase polypeptide of SEQ ID NO: 2, or of a fragment thereof comprising a substitution at one or more (e.g., several) positions. In an embodiment, the number of amino acid substitutions introduced into the polypeptide of SEQ ID NO: 2 is 1-50, 1-40, 1-30, 1-20, 1-10 or 1-5, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 35, 36, 37, 38, 39, 40, 41, 42, 43, 44, 45, 46, 47, 48, 49 or 50.

In another embodiment, the present invention relates to variants of the chaperone polypeptide of SEQ ID NO: 3, or of a fragment thereof comprising a substitution at one or more (e.g., several) positions. In an embodiment, the number of amino acid substitutions introduced into the polypeptide of SEQ ID NO: 3 is 1-50, 1-40, 1-30, 1-20, 1-10 or 1-5, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 35, 36, 37, 38, 39, 40, 41, 42, 43, 44, 45, 46, 47, 48, 49 or 50.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for lipase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO95/17413; or WO95/22625. Other methods that can be used include error-prone PCR, phage display (e.g., Lowman et al., 1991, *Biochemistry* 30: 10832-10837; U.S. Pat. No. 5,223,409; WO92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, Proteins: Structure, *Function, and Genetics* 6: 240-248; and Stevens, 2003, *Drug Discovery World* 4: 35-48.

It is contemplated that the polypeptide of the invention having lipase activity as described above may also provide basis for one or more (e.g. several) substitutions for generation of lipase variants. Accordingly the polypeptide will also be a parent lipase.

Sources of Polypeptides with Lipase Activity and of Polypeptides with the Ability to Function as Chaperones The polypeptide with lipase activity and/or polypeptides with the ability to function as chaperones of the present invention may be obtained from microorganisms of any genus.

The polypeptide with lipase activity may be a microbial lipase. In a preferred aspect, the polypeptide is a bacterial lipase. In a more preferred aspect, the polypeptide is a *Gallaecimonas* sp. lipase. In an even more preferred aspect, the polypeptide is a *Gallaecimonas pentaromativorans* lipase, e.g., the lipase of SEQ ID NO: 2, the mature polypeptide of SEQ ID NO: 2, a polypeptide having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2; or a fragment thereof.

The lipase of SEQ ID NO: 2 is dependent on a chaperone in order to fold into an enzymatically active conformation. The chaperone polypeptide may be a microbial chaperone. In a preferred aspect, the chaperone polypeptide is a bacterial chaperone. In a more preferred aspect, the chaperone polypeptide is a *Gallaecimonas* sp. chaperone. In an even more preferred aspect, the chaperone polypeptide is a *Gallaecimonas pentaromativorans* chaperone, e.g., the chaperone of SEQ ID NO: 3, a polypeptide having at least 60%, at least 65%, at least 70%, at least 75%, at least at least 80%, at least 85%, at least 86%, at least 86%, at least 87%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 3, or a fragment thereof.

It will be understood that for the aforementioned species, the invention encompasses other taxonomic equivalents, e.g., anamorphs, regardless of the species name by which they are known. Those skilled in the art will readily recognize the identity of appropriate equivalents.

Strains of bacterial and fungal species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and *Agricultural Research* Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Preparation of Polypeptides

The present invention also relates to methods for obtaining a polypeptide having lipase activity, comprising: (a) introducing into a parent lipase (e.g. a wild type) a substitution at one or more (e.g., several) positions corresponding to positions of the polypeptide of SEQ ID NO: 2; and (b) recovering the variant.

Furthermore, the present invention also relates to methods for obtaining a polypeptide having the ability to function as a chaperone to the polypeptide having lipase activity, comprising: (a) introducing into a parent chaperone (e.g. a wild type) a substitution at one or more (e.g., several) positions corresponding to positions of the polypeptide of SEQ ID NO: 3; and (b) recovering the variant.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., US2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO95/17413; or WO95/22625. Other methods that can be used include error-prone PCR, phage display (e.g., Lowman et al., 1991, *Biochemistry* 30: 10832-10837; U.S. Pat. No. 5,223,409; WO92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of a polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO96/00787), *Fusarium venenatum* amyloglucosidase (WO00/56900), *Fusarium venenatum* Daria (WO00/56900), *Fusarium venenatum* Quinn (WO00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator sequence is operably linked to the 3'-terminus of the polynucleotide encoding the polypeptide. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader sequence is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polypeptide-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used. Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus nigerglucoamylase, Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the polypeptide and the signal peptide sequence is positioned next to the N-terminus of the propeptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAM $\beta$1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO00/24883). Isolation of the AMA1 gene and construction of plasmids or vectors comprising the gene can be accomplished according to the methods disclosed in WO00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a polypeptide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

In a preferred aspect, the cell is an *E. coli* cell.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO96/00787. Yeast may be transformed using the procedures described by Becker and Guarente, In Abelson, J. N. and Simon, M. I., editors, *Guide to Yeast Genetics and Molecular Biology*, Methods in Enzymology, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide, comprising: (a) cultivating a host cell of the present invention under conditions suitable for expression of the polypeptide; and (b) recovering the polypeptide. The polypeptide with lipase activity and the chaperone polypeptide may be expressed in the same host cell. Alternatively the polypeptide with lipase activity and the chaperone polypeptide may be expressed in separate host cells.

The host cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide. Examples of lipase activity assays are known in the art including plate assay and pNP assay as described in the in the examples.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

The chaperones can bind their substrate lipases with high affinity to form 1:1 complexes in vitro, which allow copurification of both proteins from a fermentation broth.

In an alternative aspect, the polypeptide is not recovered, but rather a host cell of the present invention expressing the polypeptide is used as a source of the polypeptide.

Compositions

Compositions comprising the polypeptides of the present inventions are also contemplated. Such compositions preferably comprise both the polypeptide with lipase activity and the chaperone polypeptide. However, also compositions comprising only the polypeptide with lipase activity or compositions comprising only the chaperone polypeptide are contemplated.

In one aspect the present invention relates to compositions comprising an isolated polypeptide with lipase activity having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2.

In one aspect the present invention relates to compositions comprising an isolated polypeptide with lipase activity having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 20.

In certain aspects the present invention relates to compositions comprising an isolated polypeptide with lipase activity having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2 and an isolated polypeptide having the ability to function as a chaperone to the lipase polypeptide having at least 60%, at least 65%, at least 70%, at least 75%, at least at least 80%, at least 85%, at least 86%, at least 86%, at least 87%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 3.

In certain aspects the present invention relates to compositions comprising an isolated polypeptide with lipase activity having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2 and an isolated polypeptide having the ability to function as a chaperone to the lipase polypeptide having at least 60%, at least 65%, at least 70%, at least 75%, at least at least 80%, at least 85%, at least 86%, at least 86%, at least 87%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 21.

In certain aspects the present invention relates to compositions comprising an isolated polypeptide with lipase activity having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 20 and an isolated polypeptide having the ability to function as a chaperone to the lipase polypeptide having at least 60%, at least 65%, at least 70%, at least 75%, at least at least 80%, at least 85%, at least 86%, at least 86%, at least 87%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 3.

In certain aspects the present invention relates to compositions comprising an isolated polypeptide with lipase activity having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 20 and an isolated polypeptide having the ability to function as a chaperone to the lipase polypeptide having at least 60%, at least 65%, at least 70%, at least 75%, at least at least 80%, at least 85%, at least 86%, at least 86%, at least 87%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 21.

Such compositions of the invention comprising both the lipase and its cognate chaperone preferably comprises lipase:chaperone in a molar ratio of at least 1:4, at least 1:3, at least 1:2, at least 1:1, at least 1.5:1.0, at least 2:1, at least 3:1, or even at least 4:1, and preferably in a ratio of no more than 4:1, no more than 3:1, no more than 2:1, no more than 1:1, no more than 1:2, no more than 1:3, and even no more than 1:4.

The non-limiting list of composition components illustrated hereinafter are suitable for use in the compositions and methods herein may be desirably incorporated in certain embodiments of the invention, e.g. to assist or enhance cleaning performance, for treatment of the substrate to be cleaned, or to modify the aesthetics of the composition as is the case with perfumes, colorants, dyes or the like. The levels of any such components incorporated in any compositions are in addition to any materials previously recited for incorporation. The precise nature of these additional components, and levels of incorporation thereof, will depend on the physical form of the composition and the nature of the cleaning operation for which it is to be used. Although components mentioned below are categorized by general header according to a particular functionality, this is not to be construed as a limitation, as a component may comprise additional functionalities as will be appreciated by the skilled artisan.

Unless otherwise indicated the amounts in percentage is by weight of the composition (wt %). Suitable component materials include, but are not limited to, surfactants, builders, chelating agents, dye transfer inhibiting agents, dispersants, enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, hueing dyes, perfumes, perfume delivery systems, structure elasticizing agents, fabric softeners, carriers, hydrotropes, processing aids, solvents and/or pigments. In addition to the disclosure below, suitable examples of such other components and levels of use are found in U.S. Pat. Nos. 5,576,282, 6,306,812, and 6,326,348 hereby incorporated by reference.

Thus, in certain embodiments the invention do not contain one or more of the following adjuncts materials: surfactants, soaps, builders, chelating agents, dye transfer inhibiting agents, dispersants, additional enzymes, enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, perfume delivery systems, structure elasticizing agents, fabric softeners, carriers, hydrotropes, processing aids, solvents and/or pigments. However, when one or more components are present, such one or more components may be present as detailed below.

Detergent Compositions

In one aspect, the invention relates to a detergent composition comprising:
  (a) the lipase of the invention; and
  (b) a builder.

In one aspect, the invention relates to a detergent composition comprising:
  (a) the lipase of the invention; and
  (b) a builder, wherein the builder is an aminopolycarboxylate-based chelating agent, preferably selected from the group consisting of etheylenediaminetetraacetic acid (EDTA), diethylenetriaminepentaacetic acid (DTPA), methylglycinediacetic acid (MGDA), and glutamic acid-N,N-diacetic acid (GLDA), In one aspect, the invention relates to a detergent composition comprising:
  (a) the lipase of the invention; and
  (b) a surfactant.

In one aspect, the invention relates to a detergent composition comprising:
(a) the lipase of the invention; and
(b) a surfactant, wherein the surfactant is a sodium (linear alkyl)benzenesulfonate (LAS).

In one aspect, the invention relates to a detergent composition comprising:
(a) the lipase of the invention; and
(b) a surfactant, wherein the surfactant is a sodium alkyl sulfate (AS).

In one aspect, the invention relates to a detergent composition comprising:
(a) the lipase of the invention; and
(b) a surfactant, wherein the surfactant is a sodium lauryl ether sulfate (AEOS).

In one aspect, the invention relates to a detergent composition comprising:
(a) the lipase of the invention; and
(b) a surfactant, wherein the surfactant is an alcohol ethoxylate (AEO).

In one aspect, the invention relates to a detergent composition comprising:
(a) the lipase of the invention; and
(b) a surfactant, wherein the surfactant is an alpha-olefinsulfonate (AOS).

In one aspect, the invention relates to a detergent composition comprising:
(a) the lipase of the invention;
(b) a surfactant; and
(c) a builder.

In one aspect, the invention relates to a detergent composition comprising:
(a) the lipase of the invention;
(b) a surfactant; and
(c) a builder, wherein the builder is an aminopolycarboxylate-based chelating agent, preferably selected from the group consisting of etheylenediaminetetraacetic acid (EDTA), diethylenetriaminepentaacetic acid (DTPA), methylglycinediacetic acid (MGDA), and glutamic acid-N,N-diacetic acid (GLDA).

In one aspect, the invention relates to a detergent composition comprising:
(a) the lipase of the invention;
(b) a surfactant, wherein the surfactant is a sodium (linear alkyl)benzenesulfonate (LAS); and
(c) a builder, wherein the builder is an aminopolycarboxylate-based chelating agent, preferably selected from the group consisting of etheylenediaminetetraacetic acid (EDTA), diethylenetriaminepentaacetic acid (DTPA), methylglycinediacetic acid (MGDA), and glutamic acid-N,N-diacetic acid (GLDA).

In one aspect, the invention relates to a detergent composition comprising:
(a) the lipase of the invention;
(b) a surfactant, wherein the surfactant is a sodium alkyl sulfate (AS); and
(c) a builder, wherein the builder is an aminopolycarboxylate-based chelating agent, preferably selected from the group consisting of etheylenediaminetetraacetic acid (EDTA), diethylenetriaminepentaacetic acid (DTPA), methylglycinediacetic acid (MGDA), and glutamic acid-N,N-diacetic acid (GLDA).

In one aspect, the invention relates to a detergent composition comprising:
(a) the lipase of the invention;
(b) a surfactant, wherein the surfactant is a sodium lauryl ether sulfate (AEOS); and
(c) a builder, wherein the builder is an aminopolycarboxylate-based chelating agent, preferably selected from the group consisting of etheylenediaminetetraacetic acid (EDTA), diethylenetriaminepentaacetic acid (DTPA), methylglycinediacetic acid (MGDA), and glutamic acid-N,N-diacetic acid (GLDA).

In one aspect, the invention relates to a detergent composition comprising:
(a) the lipase of the invention;
(b) a surfactant, wherein the surfactant is an alcohol ethoxylate (AEO); and
(c) a builder, wherein the builder is an aminopolycarboxylate-based chelating agent, preferably selected from the group consisting of etheylenediaminetetraacetic acid (EDTA), diethylenetriaminepentaacetic acid (DTPA), methylglycinediacetic acid (MGDA), and glutamic acid-N,N-diacetic acid (GLDA).

In one aspect, the invention relates to a detergent composition comprising:
(a) the lipase of the invention;
(b) a surfactant, wherein the surfactant is an alpha-olefinsulfonates (AOS); and
(c) a builder, wherein the builder is an aminopolycarboxylate-based chelating agent, preferably selected from the group consisting of etheylenediaminetetraacetic acid (EDTA), diethylenetriaminepentaacetic acid (DTPA), methylglycinediacetic acid (MGDA), and glutamic acid-N,N-diacetic acid (GLDA).

In one aspect, the invention relates to a detergent composition comprising:
(a) the lipase of the invention; and
(b) a bleach catalyst.

In one aspect, the invention relates to a detergent composition comprising:
(a) the lipase of the invention; and
(b) a bleach catalyst, wherein the bleach catalyst is a manganese catalyst, preferably manganese triazacyclononane (MnTACN).

In one aspect, the invention relates to a detergent composition comprising:
(a) the lipase of the invention;
(b) a bleach catalyst; and
(c) a surfactant.

In one aspect, the invention relates to a detergent composition comprising:
(a) the lipase of the invention; and
(b) a bleach catalyst, wherein the bleach catalyst is a manganese catalyst, preferably manganese triazacyclononane (MnTACN); and
(c) a surfactant.

In one aspect, the invention relates to a detergent composition comprising:
(a) the lipase of the invention;
(b) a bleach catalyst; and
(c) a surfactant, wherein the surfactant is selected from the group consisting of sodium (linear alkyl)benzenesulfonate (LAS), sodium alkyl sulfate (AS), sodium lauryl ether sulfate (AEOS), alcohol ethoxylate (AEO) and alpha-olefinsulfonate (AOS).

In one aspect, the invention relates to a detergent composition comprising:
(a) the lipase of the invention;
(b) a bleach catalyst, wherein the bleach catalyst is a manganese catalyst, preferably manganese triazacyclononane (MnTACN); and
(c) a surfactant, wherein the surfactant is selected from the group coinsisting of sodium (linear alkyl)benzenesulfonate (LAS), sodium alkyl sulfate (AS), sodium lauryl ether sulfate (AEOS), alcohol ethoxylate (AEO) and alpha-olefinsulfonate (AOS).

In one aspect, the invention relates to a detergent composition comprising:
(a) the lipase of the invention;
(b) a bleach catalyst, wherein the bleach catalyst is a manganese catalyst, preferably manganese triazacyclononane (MnTACN);
(c) a surfactant, wherein the surfactant is selected from the group coinsisting of sodium (linear alkyl)benzenesulfonate (LAS), sodium alkyl sulfate (AS), sodium lauryl ether sulfate (AEOS), alcohol ethoxylate (AEO) and alpha-olefinsulfonate (AOS); and
(d) a builder.

In one aspect, the invention relates to a detergent composition comprising:
(a) the lipase of the invention;
(b) a bleach catalyst, wherein the bleach catalyst is a manganese catalyst, preferably manganese triazacyclononane (MnTACN);
(c) a surfactant, wherein the surfactant is selected from the group coinsisting of sodium (linear alkyl)benzenesulfonate (LAS), sodium alkyl sulfate (AS), sodium lauryl ether sulfate (AEOS), alcohol ethoxylate (AEO) and alpha-olefinsulfonate (AOS); and
(d) a builder, wherein the builder is an aminopolycarboxylate-based chelating agent, preferably selected from the group consisting of etheylenediaminetetraacetic acid (EDTA), diethylenetriaminepentaacetic acid (DTPA), methylglycinediacetic acid (MGDA), and glutamic acid-N,N-diacetic acid (GLDA).

Surfactants

The compositions according to the present invention may comprise a surfactant or surfactant system wherein the surfactant can be selected from nonionic surfactants, anionic surfactants, cationic surfactants, ampholytic surfactants, zwitterionic surfactants, semi-polar nonionic surfactants and mixtures thereof. When present, surfactant is typically present at a level of from 0.1 to 60 wt %, from 0.2 to 40 wt %, from 0.5 to 30 wt %, from 1 to 50 wt %, from 1 to 40 wt %, from 1 to 30 wt %, from 1 to 20 wt %, from 3 to 10 wt %, from 3 to 5 wt %, from 5 to 40 wt %, from 5 to 30 wt %, from 5 to 15 wt %, from 3 to 20 wt %, from 3 to 10 wt %, from 8 to 12 wt %, from 10 to 12 wt % or from 20 to 25 wt %.

Suitable anionic detersive surfactants include sulphate and sulphonate detersive surfactants.

Suitable sulphonate detersive surfactants include alkyl benzene sulphonate, in one aspect, $C_{10-13}$ alkyl benzene sulphonate. Suitable alkyl benzene sulphonate (LAS) may be obtained, by sulphonating commercially available linear alkyl benzene (LAB); suitable LAB includes low 2-phenyl LAB, such as Isochem® or Petrelab®, other suitable LAB include high 2-phenyl LAB, such as Hyblene®. A suitable anionic detersive surfactant is alkyl benzene sulphonate that is obtained by DETAL catalyzed process, although other synthesis routes, such as HF, may also be suitable. In one aspect a magnesium salt of LAS is used.

Suitable sulphate detersive surfactants include alkyl sulphate, in one aspect, $C_{8-18}$ alkyl sulphate, or predominantly $C_{12}$ alkyl sulphate.

Another suitable sulphate detersive surfactant is alkyl alkoxylated sulphate, in one aspect, alkyl ethoxylated sulphate, in one aspect, a $C_{8-18}$ alkyl alkoxylated sulphate, in another aspect, a $C_{8-18}$ alkyl ethoxylated sulphate, typically the alkyl alkoxylated sulphate has an average degree of alkoxylation of from 0.5 to 20, or from 0.5 to 10, typically the alkyl alkoxylated sulphate is a $C_{8-18}$ alkyl ethoxylated sulphate having an average degree of ethoxylation of from 0.5 to 10, from 0.5 to 7, from 0.5 to 5 or from 0.5 to 3.

The alkyl sulphate, alkyl alkoxylated sulphate and alkyl benzene sulphonates may be linear or branched, substituted or un-substituted.

The detersive surfactant may be a mid-chain branched detersive surfactant, in one aspect, a mid-chain branched anionic detersive surfactant, in one aspect, a mid-chain branched alkyl sulphate and/or a mid-chain branched alkyl benzene sulphonate, e.g. a mid-chain branched alkyl sulphate. In one aspect, the mid-chain branches are $C_{1-4}$ alkyl groups, typically methyl and/or ethyl groups.

Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

Suitable non-ionic detersive surfactants are selected from the group consisting of: $C_8$-$C_{18}$ alkyl ethoxylates, such as, NEODOL®; $C_6$-$C_{12}$ alkyl phenol alkoxylates wherein the alkoxylate units may be ethyleneoxy units, propyleneoxy units or a mixture thereof; $C_{12}$-$C_{18}$ alcohol and $C_6$-$C_{12}$ alkyl phenol condensates with ethylene oxide/propylene oxide block polymers such as Pluronic®; $C_{14}$-$C_{22}$ mid-chain branched alcohols; $C_{14}$-$C_{22}$ mid-chain branched alkyl alkoxylates, typically having an average degree of alkoxylation of from 1 to 30; alkylpolysaccharides, in one aspect, alkylpolyglycosides; polyhydroxy fatty acid amides; ether capped poly(oxyalkylated) alcohol surfactants; and mixtures thereof.

Suitable non-ionic detersive surfactants include alkyl polyglucoside and/or an alkyl alkoxylated alcohol.

In one aspect, non-ionic detersive surfactants include alkyl alkoxylated alcohols, in one aspect $C_{8-18}$ alkyl alkoxylated alcohol, e.g. a $C_{8-18}$ alkyl ethoxylated alcohol, the alkyl alkoxylated alcohol may have an average degree of alkoxylation of from 1 to 50, from 1 to 30, from 1 to 20, or from 1 to 10. In one aspect, the alkyl alkoxylated alcohol may be a $C_{8-18}$ alkyl ethoxylated alcohol having an average degree of ethoxylation of from 1 to 10, from 1 to 7, more from 1 to 5 or from 3 to 7. The alkyl alkoxylated alcohol can be linear or branched, and substituted or un-substituted. Suitable nonionic surfactants include Lutensol®.

Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

Suitable cationic detersive surfactants include alkyl pyridinium compounds, alkyl quaternary ammonium compounds, alkyl quaternary phosphonium compounds, alkyl ternary sulphonium compounds, and mixtures thereof.

Suitable cationic detersive surfactants are quaternary ammonium compounds having the general formula: $(R)(R_1)(R_2)(R_3)N^+X^-$, wherein, R is a linear or branched, substituted or unsubstituted $C_{6-18}$ alkyl or alkenyl moiety, $R_1$ and $R_2$ are independently selected from methyl or ethyl moieties, $R_3$ is a hydroxyl, hydroxymethyl or a hydroxyethyl moiety, X is an anion which provides charge neutrality, suitable anions include: halides, e.g. chloride; sulphate; and sulphonate. Suitable cationic detersive surfactants are mono-$C_{6-18}$ alkyl mono-hydroxyethyl di-methyl quaternary ammonium chlorides. Highly suitable cationic detersive surfactants are mono-$C_{8-10}$ alkyl mono-hydroxyethyl di-methyl quaternary ammonium chloride, mono-$C_{10-12}$ alkyl mono-hydroxyethyl di-methyl quaternary ammonium chloride and mono-$C_{10}$ alkyl mono-hydroxyethyl di-methyl quaternary ammonium chloride.

Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, ester quats, and combinations thereof.

Suitable amphoteric/zwitterionic surfactants include amine oxides and betaines such as alkyldimethylbetaines, sulfobetaines, or combinations thereof. Amine-neutralized anionic surfactants—Anionic surfactants of the present invention and adjunct anionic cosurfactants, may exist in an acid form, and said acid form may be neutralized to form a surfactant salt which is desirable for use in the present detergent compositions. Typical agents for neutralization include the metal counterion base such as hydroxides, e.g., NaOH or KOH. Further preferred agents for neutralizing anionic surfactants of the present invention and adjunct anionic surfactants or cosurfactants in their acid forms include ammonia, amines, or alkanolamines. Alkanolamines are preferred. Suitable non-limiting examples including monoethanolamine, diethanolamine, triethanolamine, and other linear or branched alkanolamines known in the art; e.g., highly preferred alkanolamines include 2-amino-1-propanol, 1-aminopropanol, monoisopropanolamine, or 1-amino-3-propanol. Amine neutralization may be done to a full or partial extent, e.g. part of the anionic surfactant mix may be neutralized with sodium or potassium and part of the anionic surfactant mix may be neutralized with amines or alkanolamines.

Non-Limiting Examples of Semipolar Surfactants Include Amine Oxides (AO) Such as Alkyldimethylamineoxide Surfactant systems comprising mixtures of one or more anionic and in addition one or more nonionic surfactants optionally with an additional surfactant such as a cationic surfactant, may be preferred. Preferred weight ratios of anionic to nonionic surfactant are at least 2:1, or at least 1:1 to 1:10.

In certain embodiments of the invention the composition comprises surfactants or surfactant systems selected from sodium dodecyl benzene sulfonate, sodium hydrogenated cocoate, sodium laureth sulfate, C12-14 pareth-7, C12-15 pareth-7, sodium C12-15 pareth sulfate, and C14-15 pareth-4.

Soap

The compositions herein may contain soap. Without being limited by theory, it may be desirable to include soap as it acts in part as a surfactant and in part as a builder and may be useful for suppression of foam and may furthermore interact favorably with the various cationic compounds of the composition to enhance softness on textile fabrics treaded with the inventive compositions. Any soap known in the art for use in laundry detergents may be utilized. In one embodiment, the compositions contain from 0 wt % to 20 wt %, from 0.5 wt % to 20 wt %, from 4 wt % to 10 wt %, or from 4 wt % to 7 wt % of soap.

Examples of soap useful herein include oleic acid soaps, palmitic acid soaps, palm kernel fatty acid soaps, and mixtures thereof. Typical soaps are in the form of mixtures of fatty acid soaps having different chain lengths and degrees of substitution. One such mixture is topped palm kernel fatty acid.

In one embodiment, the soap is selected from free fatty acid. Suitable fatty acids are saturated and/or unsaturated and can be obtained from natural sources such a plant or animal esters (e.g., palm kernel oil, palm oil, coconut oil, babassu oil, safflower oil, tall oil, castor oil, tallow and fish oils, grease, and mixtures thereof), or synthetically prepared (e.g., via the oxidation of petroleum or by hydrogenation of carbon monoxide via the Fisher Tropsch process).

Examples of suitable saturated fatty acids for use in the compositions of this invention include captic, lauric, myristic, palmitic, stearic, arachidic and behenic acid. Suitable unsaturated fatty acid species include: palmitoleic, oleic, linoleic, linolenic and ricinoleic acid. Examples of preferred fatty acids are saturated Cn fatty acid, saturated $Ci_2$-$Ci_4$ fatty acids, and saturated or unsaturated Cn to $Ci_8$ fatty acids, and mixtures thereof.

When present, the weight ratio of fabric softening cationic cosurfactant to fatty acid is preferably from about 1:3 to about 3:1, more preferably from about 1:1.5 to about 1.5:1, most preferably about 1:1.

Levels of soap and of nonsoap anionic surfactants herein are percentages by weight of the detergent composition, specified on an acid form basis. However, as is commonly understood in the art, anionic surfactants and soaps are in practice neutralized using sodium, potassium or alkanolammonium bases, such as sodium hydroxide or monoethanolamine.

Hydrotropes

The compositions of the present invention may comprise one or more hydrotropes. A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation, see e.g. review by Hodgdon and Kaler (2007), Current Opinion in Colloid & Interface Science 12: 121-128. Hydrotropes do not display a critical concentration above which self-aggregation occurs as found for surfactants and lipids forming miceller, lamellar or other well defined mesophases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain from 0 to 10 wt %, such as from 0 to 5 wt %, 0.5 to 5 wt %, or from 3% to 5 wt %, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Builders

The compositions of the present invention may comprise one or more builders, co-builders, builder systems or a mixture thereof. When a builder is used, the cleaning composition will typically comprise from 0 to 65 wt %, at least 1 wt %, from 2 to 60 wt % or from 5 to 10 wt % builder. In a dish wash cleaning composition, the level of builder is typically 40 to 65 wt % or 50 to 65 wt %. The composition may be substantially free of builder; substantially free means "no deliberately added" zeolite and/or phosphate. Typical zeolite builders include zeolite A, zeolite P and zeolite MAP. A typical phosphate builder is sodium tri-polyphosphate.

The builder and/or co-builder may particularly be a chelating agent that forms water-soluble complexes with Ca and Mg. Any builder and/or co-builder known in the art for use in detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), iminodiethanol (DEA) and 2,2',2"-nitrilotriethanol (TEA), and carboxymethylinulin (CMI), and combinations thereof. The cleaning composition may include a co-builder alone, or in combination with a builder, e.g. a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), etheylenediaminetetraacetic acid (EDTA), diethylenetri-aminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diylbis(phosphonic acid) (HEDP), ethylenediaminetetra-kis(methylene)tetrakis(phosphonic acid) (EDTMPA), diethylenetriaminepentakis (methylene) pentakis(phosphonic acid) (DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl) aspartic acid (SMAS), N-(2-sulfoethyl) aspartic acid (SEAS), N-(2-sulfomethyl) glutamic acid (SMGL), N-(2-sulfoethyl) glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N, N-diacetic acid (SLDA), taurine-N, N-diacetic acid (TUDA) and sulfomethyl-N,N-diacetic acid (SMDA), N-(hydroxyethyl)-ethylidenediaminetriacetate (HEDTA), diethanolglycine (DEG), Diethylenetriamine Penta (Methylene Phosphonic acid) (DTPMP), aminotris(methylenephosphonic acid) (ATMP), and combinations and salts thereof. Further exemplary builders and/or co-builders are described in, e.g., WO09/102854, U.S. Pat. No. 5,977,053.

Chelating Agents and Crystal Growth Inhibitors

The compositions herein may contain a chelating agent and/or a crystal growth inhibitor. Suitable molecules include copper, iron and/or manganese chelating agents and mixtures thereof. Suitable molecules include DTPA (Diethylene triamine pentaacetic acid), HEDP (Hydroxyethane diphosphonic acid), DTPMP (Diethylene triamine penta(methylene phosphonic acid)), 1,2-Dihydroxybenzene-3,5-disulfonic acid disodium salt hydrate, ethylenediamine, diethylene triamine, ethylenediaminedisuccinic acid (EDDS), N-hydroxyethylethylenediaminetri-acetic acid (HEDTA), triethylenetetra-aminehexaacetic acid (TTNA), N-hydroxyethyl-iminodiacetic acid (HEIDA), dihydroxyethylglycine (DHEG), ethylenediaminetetrapropionic acid (EDTP), carboxymethyl inulin and 2-Phosphonobutane 1,2,4-tricarboxylic acid (Bayhibit® AM) and derivatives thereof. Typically the composition may comprise from 0.005 to 15 wt % or from 3.0 to 10 wt % chelating agent or crystal growth inhibitor.

Bleach Component

The bleach component suitable for incorporation in the methods and compositions of the invention comprise one or a mixture of more than one bleach component. Suitable bleach components include bleaching catalysts, photobleaches, bleach activators, hydrogen peroxide, sources of hydrogen peroxide, pre-formed peracids and mixtures thereof. In general, when a bleach component is used, the compositions of the present invention may comprise from 0 to 30 wt %, from 0.00001 to 90 wt %, 0.0001 to 50 wt %, from 0.001 to 25 wt % or from 1 to 20 wt %. Examples of suitable bleach components include:

(1) Pre-formed peracids: Suitable preformed peracids include, but are not limited to, compounds selected from the group consisting of pre-formed peroxyacids or salts thereof, typically either a peroxycarboxylic acid or salt thereof, or a peroxysulphonic acid or salt thereof.

The pre-formed peroxyacid or salt thereof is preferably a peroxycarboxylic acid or salt thereof, typically having a chemical structure corresponding to the following chemical formula:

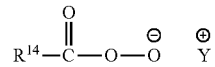

wherein: $R^{14}$ is selected from alkyl, aralkyl, cycloalkyl, aryl or heterocyclic groups; the $R^{14}$ group can be linear or branched, substituted or unsubstituted; and Y is any suitable counter-ion that achieves electric charge neutrality, preferably Y is selected from hydrogen, sodium or potassium. Preferably, $R^{14}$ is a linear or branched, substituted or unsubstituted $C_{6-9}$ alkyl. Preferably, the peroxyacid or salt thereof is selected from peroxyhexanoic acid, peroxyheptanoic acid, peroxyoctanoic acid, peroxynonanoic acid, peroxydecanoic acid, any salt thereof, or any combination thereof. Particularly preferred peroxyacids are phthalimido-peroxy-alkanoic acids, in particular ε-phthahlimido peroxy hexanoic acid (PAP). Preferably, the peroxyacid or salt thereof has a melting point in the range of from 30° C. to 60° C. The pre-formed peroxyacid or salt thereof can also be a peroxysulphonic acid or salt thereof, typically having a chemical structure corresponding to the following chemical formula:

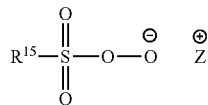

wherein: $R^{15}$ is selected from alkyl, aralkyl, cycloalkyl, aryl or heterocyclic groups; the $R^{15}$ group can be linear or branched, substituted or unsubstituted; and Z is any suitable counter-ion that achieves electric charge neutrality, preferably Z is selected from hydrogen, sodium or potassium. Preferably $R^{15}$ is a linear or branched, substituted or unsubstituted $C_{6-9}$ alkyl. Preferably such bleach components may be present in the compositions of the invention in an amount from 0.01 to 50 wt % or from 0.1 to 20 wt %.

(2) Sources of hydrogen peroxide include e.g., inorganic perhydrate salts, including alkali metal salts such as sodium salts of perborate (usually mono- or tetra-hydrate), percarbonate, persulphate, perphosphate, persilicate salts and mixtures thereof. In one aspect of the invention the inorganic perhydrate salts such as those selected from the group consisting of sodium salts of perborate, percarbonate and mixtures thereof. When employed, inorganic perhydrate salts are typically present in amounts of 0.05 to 40 wt % or 1 to 30 wt % of the overall composition and are typically incorporated into such compositions as a crystalline solid that may be coated. Suitable coatings include: inorganic salts such as alkali metal silicate, carbonate or borate salts or mixtures thereof, or organic materials such as water-soluble or dispersible polymers, waxes, oils or fatty soaps. Preferably such bleach components may be present in the compositions of the invention in an amount of 0.01 to 50 wt % or 0.1 to 20 wt %.

(3) The term bleach activator is meant herein as a compound which reacts with hydrogen peroxide to form a peracid via perhydrolysis. The peracid thus formed constitutes the activated bleach. Suitable bleach activators to be used herein include those belonging to the class of esters, amides, imides or anhydrides. Suitable bleach activators are those having R—(C=O)-L wherein R is an alkyl group, optionally branched, having, when the bleach activator is hydrophobic, from 6 to 14 carbon atoms, or from 8 to 12 carbon atoms and, when the bleach activator is hydrophilic, less than 6 carbon atoms or less than 4 carbon atoms; and L is leaving group. Examples of suitable leaving groups are benzoic acid and derivatives thereof—especially benzene sulphonate. Suitable bleach activators include dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED), sodium 4-[(3,5,5-trimethylhexanoyl)oxy] benzene-1-sulfonate (ISONOBS), 4-(dodecanoyloxy)benzene-1-sulfonate (LOBS), 4-(decanoyloxy)benzene-1-sulfonate, 4-(decanoyloxy)benzoate (DOBS or DOBA), 4-(nonanoyloxy)benzene-1-sulfonate (NOBS), and/or those disclosed in WO98/17767. A family of bleach activators disclosed in EP624154 and particularly preferred in that family is acetyl triethyl citrate (ATC). ATC or a short chain triglyceride like triacetin has the advantage that it is environmentally friendly. Furthermore acetyl triethyl citrate and triacetin have good hydrolytical stability in the product upon storage and are efficient bleach activators. Finally ATC is multifunctional, as the citrate released in the perhydrolysis reaction may function as a builder. Alternatively, the bleaching system may comprise peroxyacids of, for example, the amide, imide, or sulfone type. The bleaching system may also comprise peracids such as 6-(phthalimido)peroxyhexanoic acid (PAP). Suitable bleach activators are also disclosed in WO98/17767. While any suitable bleach activator may be employed, in one aspect of the invention the subject cleaning composition may comprise NOBS, TAED or mixtures thereof. When present, the peracid and/or bleach activator is generally present in the composition in an amount of 0.1 to 60 wt %, 0.5 to 40 wt % or 0.6 to 10 wt % based on the fabric and home care composition. One or more hydrophobic peracids or precursors thereof may be used in combination with one or more hydrophilic peracid or precursor thereof. Preferably such bleach components may be present in the compositions of the invention in an amount of 0.01 to 50 wt %, or 0.1 to 20 wt %.

The amounts of hydrogen peroxide source and peracid or bleach activator may be selected such that the molar ratio of available oxygen (from the peroxide source) to peracid is from 1:1 to 35:1, or even 2:1 to 10:1.

(4) Diacyl peroxides preferred diacyl peroxide bleaching species include those selected from diacyl peroxides of the general formula: $R^1$—C(O)—OO—(O)C—$R^2$, in which $R^1$ represents a $C_6$-$C_{18}$ alkyl, preferably $C_6$-$C_{12}$ alkyl group containing a linear chain of at least 5 carbon atoms and optionally containing one or more substituents (e.g. 1\1' $(CH_3)_3$, —COOH or —CN) and/or one or more interrupting moieties (e.g. —CONH— or —CH=CH—) interpolated between adjacent carbon atoms of the alkyl radical, and $R^2$ represents an aliphatic group compatible with a peroxide moiety, such that $R^1$ and $R^2$ together contain a total of 8 to 30 carbon atoms. In one preferred aspect $R^1$ and $R^2$ are linear unsubstituted $C_6$-$C_{12}$ alkyl chains. Most preferably $R^1$ and $R^2$ are identical. Diacyl peroxides, in which both $R^1$ and $R^2$ are $C_6$-$C_{12}$ alkyl groups, are particularly preferred. Preferably, at least one of, most preferably only one of, the R groups ($R_1$ or $R_2$), does not contain branching or pendant rings in the alpha position, or preferably neither in the alpha nor beta positions or most preferably in none of the alpha or beta or gamma positions.

In one further preferred embodiment the DAP may be asymmetric, such that preferably the hydrolysis of R1 acyl group is rapid to generate peracid, but the hydrolysis of R2 acyl group is slow.

The tetraacyl peroxide bleaching species is preferably selected from tetraacyl peroxides of the general formula: $R^3$—C(O)—OO—C(O)—$(CH_2)$n-C(O)—OO—C(O)—$R^3$, in which $R^3$ represents a $C_1$-$C_9$ alkyl, or $C_3$-$C_7$, group and n represents an integer from 2 to 12, or 4 to 10 inclusive.

Preferably, the diacyl and/or tetraacyl peroxide bleaching species is present in an amount sufficient to provide at least 0.5 ppm, at least 10 ppm, or at least 50 ppm by weight of the wash liquor. In a preferred embodiment, the bleaching species is present in an amount sufficient to provide from 0.5 to 300 ppm, from 30 to 150 ppm by weight of the wash liquor.

Preferably the bleach component comprises a bleach catalyst (5 and 6).

(5) Preferred are organic (non-metal) bleach catalysts include bleach catalyst capable of accepting an oxygen atom from a peroxyacid and/or salt thereof, and transferring the oxygen atom to an oxidizeable substrate. Suitable bleach catalysts include, but are not limited to: iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof.

Suitable iminium cations and polyions include, but are not limited to, N-methyl-3,4-dihydroisoquinolinium tetrafluoroborate, prepared as described in *Tetrahedron* (1992), 49(2), 423-38 (e.g. compound 4, p. 433); N-methyl-3,4-dihydroisoquinolinium p-toluene sulphonate, prepared as described in U.S. Pat. No. 5,360,569 (e.g. Column 11, Example 1); and N-octyl-3,4-dihydroisoquinolinium p-toluene sulphonate, prepared as described in U.S. Pat. No. 5,360,568 (e.g. Column 10, Ex. 3).

Suitable iminium zwitterions include, but are not limited to, N-(3-sulfopropyl)-3,4-dihydroisoquinolinium, inner salt, prepared as described in U.S. Pat. No. 5,576,282 (e.g. Column 31, Ex. II); N-[2-(sulphooxy)dodecyl]-3,4-dihydroisoquinolinium, inner salt, prepared as described in U.S. Pat. No. 5,817,614 (e.g. Column 32, Ex. V); 2-[3-[(2-ethylhexyl)oxy]-2-(sulphooxy)propyl]-3,4-dihydroisoquinolinium, inner salt, prepared as described in WO05/047264 (e.g. p. 18, Ex. 8), and 2-[3-[(2-butyloctyl)oxy]-2-(sulphooxy)propyl]-3,4-dihydroisoquinolinium, inner salt.

Suitable modified amine oxygen transfer catalysts include, but are not limited to, 1,2,3,4-tetrahydro-2-methyl-1-isoquinolinol, which can be made according to the procedures described in *Tetrahedron Letters* (1987), 28(48), 6061-6064. Suitable modified amine oxide oxygen transfer catalysts include, but are not limited to, sodium 1-hydroxy-N-oxy-N-[2-(sulphooxy)decyl]-1,2,3,4-tetrahydroisoquinoline.

Suitable N-sulphonyl imine oxygen transfer catalysts include, but are not limited to, 3-methyl-1,2-benzisothiazole 1,1-dioxide, prepared according to the procedure described in the *Journal of Organic Chemistry* (1990), 55(4), 1254-61.

Suitable N-phosphonyl imine oxygen transfer catalysts include, but are not limited to, [R-(E)]-N-[(2-chloro-5-nitrophenyl)methylene]-P-phenyl-P-(2,4,6-trimethylphenyl)-phosphinic amide, which can be made according to the procedures described in the Journal of the Chemical Society, Chemical Communications (1994), (22), 2569-70.

Suitable N-acyl imine oxygen transfer catalysts include, but are not limited to, [N(E)]-N-(phenylmethylene)acetamide, which can be made according to the procedures described in Polish Journal of Chemistry (2003), 77(5), 577-590.

Suitable thiadiazole dioxide oxygen transfer catalysts include but are not limited to, 3-methyl-4-phenyl-1,2,5-thiadiazole 1,1-dioxide, which can be made according to the procedures described in U.S. Pat. No. 5,753,599 (Column 9, Ex. 2).

Suitable perfluoroimine oxygen transfer catalysts include, but are not limited to, (Z)-2,2,3,3,4,4,4-heptafluoro-N-(nonafluorobutyl)butanimidoyl fluoride, which can be made according to the procedures described in *Tetrahedron Letters* (1994), 35(34), 6329-30.

Suitable cyclic sugar ketone oxygen transfer catalysts include, but are not limited to, 1,2:4,5-di-O-isopropylidene-D-erythro-2,3-hexodiuro-2,6-pyranose as prepared in U.S. Pat. No. 6,649,085 (Column 12, Ex. 1).

Preferably, the bleach catalyst comprises an iminium and/or carbonyl functional group and is typically capable of forming an oxaziridinium and/or dioxirane functional group upon acceptance of an oxygen atom, especially upon acceptance of an oxygen atom from a peroxyacid and/or salt thereof. Preferably, the bleach catalyst comprises an oxaziridinium functional group and/or is capable of forming an oxaziridinium functional group upon acceptance of an oxygen atom, especially upon acceptance of an oxygen atom from a peroxyacid and/or salt thereof. Preferably, the bleach catalyst comprises a cyclic iminium functional group, preferably wherein the cyclic moiety has a ring size of from five to eight atoms (including the nitrogen atom), preferably six atoms. Preferably, the bleach catalyst comprises an aryliminium functional group, preferably a bi-cyclic aryliminium functional group, preferably a 3,4-dihydroisoquinolinium functional group. Typically, the imine functional group is a quaternary imine functional group and is typically capable of forming a quaternary oxaziridinium functional group upon acceptance of an oxygen atom, especially upon acceptance of an oxygen atom from a peroxyacid and/or salt thereof. In another aspect, the detergent composition comprises a bleach component having a log $P_{o/w}$ no greater than 0, no greater than -0.5, no greater than -1.0, no greater than -1.5, no greater than -2.0, no greater than -2.5, no greater than -3.0, or no greater than -3.5. The method for determining log $P_{o/w}$ is described in more detail below.

Typically, the bleach ingredient is capable of generating a bleaching species having a $X_{SO}$ of from 0.01 to 0.30, from 0.05 to 0.25, or from 0.10 to 0.20. The method for determining $X_{SO}$ is described in more detail below. For example, bleaching ingredients having an isoquinolinium structure are capable of generating a bleaching species that has an oxaziridinium structure. In this example, the $X_{SO}$ is that of the oxaziridinium bleaching species.

Preferably, the bleach catalyst has a chemical structure corresponding to the following chemical formula:

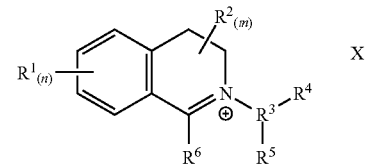

wherein: n and m are independently from 0 to 4, preferably n and m are both 0; each $R^1$ is independently selected from a substituted or unsubstituted radical selected from the group consisting of hydrogen, alkyl, cycloalkyl, aryl, fused aryl, heterocyclic ring, fused heterocyclic ring, nitro, halo, cyano, sulphonato, alkoxy, keto, carboxylic, and carboalkoxy radicals; and any two vicinal $R^1$ substituents may combine to form a fused aryl, fused carbocyclic or fused heterocyclic ring; each $R^2$ is independently selected from a substituted or unsubstituted radical independently selected from the group consisting of hydrogen, hydroxy, alkyl, cycloalkyl, alkaryl, aryl, aralkyl, alkylenes, heterocyclic ring, alkoxys, arylcarbonyl groups, carboxyalkyl groups and amide groups; any $R^2$ may be joined together with any other of $R^2$ to form part of a common ring; any geminal $R^2$ may combine to form a carbonyl; and any two $R^2$ may combine to form a substituted or unsubstituted fused unsaturated moiety; $R^3$ is a $C_1$ to $C_{20}$ substituted or unsubstituted alkyl; $R^4$ is hydrogen or the moiety $Q_t$-A, wherein: Q is a branched or unbranched alkylene, t=0 or 1 and A is an anionic group selected from the group consisting of $OSO_3^-$, $SO_3^-$, $CO_2^-$, $OCO_2^-$, $OPO_3^{2-}$, $OPO_3H^-$ and $OPO_2^-$; $R^5$ is hydrogen or the moiety —$CR^{11}R^{12}$—Y-$G_b$-$Y_c$—[$(CR^9R^{10})_y$—O]$_k$—$R^8$, wherein: each Y is independently selected from the group consisting of O, S, N—H, or N—$R^8$; and each $R^8$ is independently selected from the group consisting of alkyl, aryl and heteroaryl, said moieties being substituted or unsubstituted, and whether substituted or unsubstituted said moieties having less than 21 carbons; each G is independently selected from the group consisting of CO, $SO_2$, SO, PO and $PO_2$; $R^9$ and $R^{10}$ are independently selected from the group consisting of H and $C_1$-$C_4$ alkyl; $R^{11}$ and $R^{12}$ are independently selected from the group consisting of H and alkyl, or when taken together may join to form a carbonyl; b=0 or 1; c can=0 or 1, but c must=0 if b=0; y is an integer from 1 to 6; k is an integer from 0 to 20; $R^6$ is H, or an alkyl, aryl or heteroaryl moiety; said moieties being substituted or unsubstituted; and X, if present, is a suitable charge balancing counterion, preferably X is present when $R^4$ is hydrogen, suitable X, include but are not limited to: chloride, bromide, sulphate, methosulphate, sulphonate, p-toluenesulphonate, borontetraflouride and phosphate.

In one embodiment of the present invention, the bleach catalyst has a structure corresponding to general formula below:

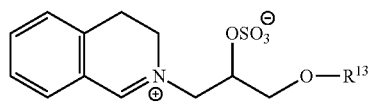

wherein $R^{13}$ is a branched alkyl group containing from three to 24 carbon atoms (including the branching carbon atoms) or a linear alkyl group containing from one to 24 carbon atoms; preferably $R^{13}$ is a branched alkyl group containing from eight to 18 carbon atoms or linear alkyl group containing from eight to eighteen carbon atoms; preferably $R^{13}$ is selected from the group consisting of 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl; preferably $R^{13}$ is selected from the group consisting of 2-butyloctyl, 2-pentylnonyl, 2-hexyldecyl, iso-tridecyl and iso-pentadecyl.

Preferably the bleach component comprises a source of peracid in addition to bleach catalyst, particularly organic bleach catalyst. The source of peracid may be selected from (a) pre-formed peracid; (b) percarbonate, perborate or persulfate salt (hydrogen peroxide source) preferably in combination with a bleach activator; and (c) perhydrolase enzyme and an ester for forming peracid in situ in the presence of water in a textile or hard surface treatment step.

When present, the peracid and/or bleach activator is generally present in the composition in an amount of from 0.1 to 60 wt %, from 0.5 to 40 wt % or from 0.6 to 10 wt % based on the composition. One or more hydrophobic peracids or precursors thereof may be used in combination with one or more hydrophilic peracid or precursor thereof.

The amounts of hydrogen peroxide source and peracid or bleach activator may be selected such that the molar ratio of available oxygen (from the peroxide source) to peracid is from 1:1 to 35:1, or 2:1 to 10:1.

(6) Metal-containing Bleach Catalysts—The bleach component may be provided by a catalytic metal complex. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra(methylenephosphonic acid) and water-soluble salts thereof. Such catalysts are disclosed in U.S. Pat. No. 4,430,243. Preferred catalysts are described in WO09/839406, U.S. Pat. No. 6,218,351 and WO00/012667. Particularly preferred are transition metal catalyst or ligands therefore that are cross-bridged polydentate N-donor ligands.

Some non-limiting examples of bleach catalysts that may be used in the compositions of the present invention include manganese oxalate, manganese acetate, manganese-collagen, cobalt-amine catalysts and manganese triazacyclononane (MnTACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn (O)3Mn(Me3-TACN)](PF6)2, and [2,2',2"-nitrilotris(ethane-1,2-diylazanylylidene-ĸN-methanylylidene)triphenolato-ĸ3O]manganese(III). The bleach catalysts may also be other metal compounds, such as iron or cobalt complexes.

If desired, the compositions herein can be catalyzed by means of a manganese compound. Such compounds and levels of use are well known in the art and include, e.g., the manganese-based catalysts disclosed in U.S. Pat. No. 5,576,282.

Cobalt bleach catalysts useful herein are known, and are described e.g. in U.S. Pat. Nos. 5,597,936; 5,595,967. Such cobalt catalysts are readily prepared by known procedures, such as taught e.g. in U.S. Pat. Nos. 5,597,936 and 5,595,967.

Compositions herein may also suitably include a transition metal complex of ligands such as bispidones (U.S. Pat. No. 7,501,389) and/or macropolycyclic rigid ligands—abbreviated as "MRLs". As a practical matter, and not by way of limitation, the compositions and processes herein can be adjusted to provide on the order of at least one part per hundred million of the active MRL species in the aqueous washing medium, and will typically provide from 0.005 to 25 ppm, from 0.05 to 10 ppm, or from 0.1 to 5 ppm, of the MRL in the wash liquor.

Suitable transition-metals in the instant transition-metal bleach catalyst include e.g. manganese, iron and chromium. Suitable MRLs include 5,12-diethyl-1,5,8,12-tetraazabicyclo[6.6.2]hexadecane. Suitable transition metal MRLs are readily prepared by known procedures, such as taught e.g. in U.S. Pat. No. 6,225,464 and WO00/32601.

(7) Photobleaches suitable photobleaches include e.g. sulfonated zinc phthalocyanine sulfonated aluminium phthalocyanines, xanthene dyes and mixtures thereof. Preferred bleach components for use in the present compositions of the invention comprise a hydrogen peroxide source, bleach activator and/or organic peroxyacid, optionally generated in situ by the reaction of a hydrogen peroxide source and bleach activator, in combination with a bleach catalyst. Preferred bleach components comprise bleach catalysts, preferably organic bleach catalysts, as described above.

Particularly preferred bleach components are the bleach catalysts in particular the organic bleach catalysts.

Exemplary bleaching systems are also described, e.g. in WO2007/087258, WO2007/087244, WO2007/087259 and WO2007/087242.

Fabric Hueing Agents

The composition may comprise a fabric hueing agent. Suitable fabric hueing agents include dyes, dye-clay conjugates, and pigments. Suitable dyes include small molecule dyes and polymeric dyes. Suitable small molecule dyes include small molecule dyes selected from the group consisting of dyes falling into the Color Index (C.I.) classifications of Direct Blue, Direct Red, Direct Violet, Acid Blue, Acid Red, Acid Violet, Basic Blue, Basic Violet and Basic Red, or mixtures thereof.

In another aspect, suitable small molecule dyes include small molecule dyes selected from the group consisting of Color Index (Society of Dyers and Colorists, Bradford, UK) numbers Direct Violet 9, Direct Violet 35, Direct Violet 48, Direct Violet 51, Direct Violet 66, Direct Violet 99, Direct Blue 1, Direct Blue 71, Direct Blue 80, Direct Blue 279, Acid Red 17, Acid Red 73, Acid Red 88, Acid Red 150, Acid Violet 15, Acid Violet 17, Acid Violet 24, Acid Violet 43, Acid Red 52, Acid Violet 49, Acid Violet 50, Acid Blue 15, Acid Blue 17, Acid Blue 25, Acid Blue 29, Acid Blue 40, Acid Blue 45, Acid Blue 75, Acid Blue 80, Acid Blue 83, Acid Blue 90 and Acid Blue 113, Acid Black 1, Basic Violet 1, Basic Violet 3, Basic Violet 4, Basic Violet 10, Basic Violet 35, Basic Blue 3, Basic Blue 16, Basic Blue 22, Basic Blue 47, Basic Blue 66, Basic Blue 75, Basic Blue 159 and mixtures thereof. In another aspect, suitable small molecule dyes include small molecule dyes selected from the group consisting of Color Index (Society of Dyers and Colorists, Bradford, UK) numbers Acid Violet 17, Acid Violet 43, Acid Red 52, Acid Red 73, Acid Red 88, Acid Red 150, Acid Blue 25, Acid Blue 29, Acid Blue 45, Acid Blue 113, Acid Black 1, Direct Blue 1, Direct Blue 71, Direct Violet 51 and mixtures thereof. In another aspect, suitable small molecule dyes include small molecule dyes selected from the group consisting of Color Index (Society of Dyers and Colorists, Bradford, UK) numbers Acid Violet 17, Direct Blue 71, Direct Violet 51, Direct Blue 1, Acid Red 88, Acid Red 150, Acid Blue 29, Acid Blue 113 or mixtures thereof.

Suitable polymeric dyes include polymeric dyes selected from the group consisting of polymers containing conjugated chromogens (dye-polymer conjugates) and polymers with chromogens co-polymerized into the backbone of the polymer and mixtures thereof.

In another aspect, suitable polymeric dyes include polymeric dyes selected from the group consisting of fabric-substantive colorants sold under the name of Liquitint® (Milliken), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In still another aspect, suitable polymeric dyes include polymeric dyes selected from the group consisting of Liquitint® Violet CT, carboxymethyl cellulose (CMC) conjugated with a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenyl-methane polymeric colorants, alkoxylated thiophene polymeric colorants, and mixtures thereof.

Preferred hueing dyes include the whitening agents found in WO08/87497. These whitening agents may be characterized by the following structure (I):

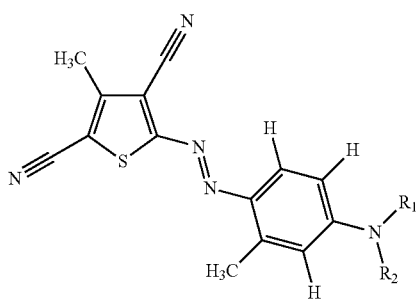

wherein $R_1$ and $R_2$ can independently be selected from:
a) $[(CH_2CR'HO)_x(CH_2CR''HO)_yH]$
wherein R' is selected from the group consisting of H, $CH_3$, $CH_2O(CH_2CH_2O)_zH$, and mixtures thereof; wherein R" is selected from the group consisting of H, $CH_2O(CH_2CH_2O)_zH$, and mixtures thereof; wherein $x+y\leq5$; wherein $y\geq1$; and wherein $z=0$ to 5;
b) $R_1$=alkyl, aryl or aryl alkyl and $R_2$=$[(CH_2CR'HO)_x(CH_2CR''HO)_yH]$
wherein R' is selected from the group consisting of H, $CH_3$, $CH_2O(CH_2CH_2O)_zH$, and mixtures thereof; wherein R" is selected from the group consisting of H, $CH_2O(CH_2CH_2O)_zH$, and mixtures thereof; wherein $x+y\leq10$; wherein $y\geq1$; and wherein $z=0$ to 5;
c) $R_1$=$[CH_2CH_2(OR_3)CH_2OR_4]$ and $R_2$=$[CH_2CH_2(OR_3)CH_2OR_4]$
wherein $R_3$ is selected from the group consisting of H, $(CH_2CH_2O)_zH$, and mixtures thereof; and wherein $z=0$ to 10;
wherein $R_4$ is selected from the group consisting of $(C_1-C_{16})$alkyl, aryl groups, and mixtures thereof; and
d) wherein R1 and R2 can independently be selected from the amino addition product of styrene oxide, glycidyl methyl ether, isobutyl glycidyl ether, isopropylglycidyl ether, t-butyl glycidyl ether, 2-ethylhexylgycidyl ether, and glycidylhexadecyl ether, followed by the addition of from 1 to 10 alkylene oxide units.

A preferred whitening agent of the present invention may be characterized by the following structure (II):

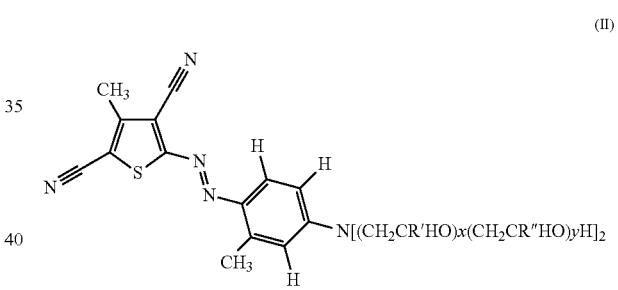

wherein R' is selected from the group consisting of H, $CH_3$, $CH_2O(CH_2CH_2O)_zH$, and mixtures thereof; wherein R" is selected from the group consisting of H, $CH_2O(CH_2CH_2O)_zH$, and mixtures thereof; wherein $x+y\leq5$; wherein $y\geq1$; and wherein $z=0$ to 5.

A further preferred whitening agent of the present invention may be characterized by the following structure (III):

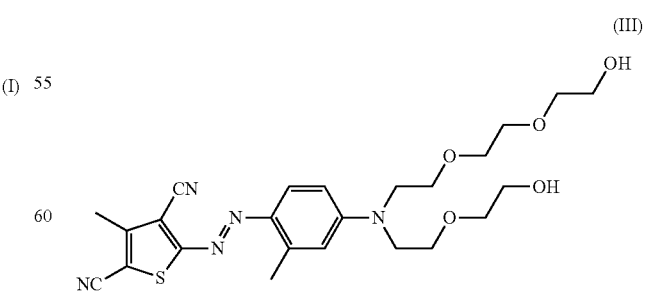

typically comprising a mixture having a total of 5 EO groups. Suitable preferred molecules are those in Structure I having the following pendant groups in "part a" above.

TABLE 1

|   | R1 | | | | R2 | | | |
|---|---|---|---|---|---|---|---|---|
|   | R' | R" | x | y | R' | R" | x | y |
| a | H | H | 3 | 1 | H | H | 0 | 1 |
| b | H | H | 2 | 1 | H | H | 1 | 1 |
| c = b | H | H | 1 | 1 | H | H | 2 | 1 |
| d = a | H | H | 0 | 1 | H | H | 3 | 1 |

Further whitening agents of use include those described in US2008/34511 (Unilever). A preferred agent is "Violet 13".

Suitable dye clay conjugates include dye clay conjugates selected from the group comprising at least one cationic/basic dye and a smectite clay, and mixtures thereof. In another aspect, suitable dye clay conjugates include dye clay conjugates selected from the group consisting of one cationic/basic dye selected from the group consisting of C.I. Basic Yellow 1 through 108, C.I. Basic Orange 1 through 69, C.I. Basic Red 1 through 118, C.I. Basic Violet 1 through 51, C.I. Basic Blue 1 through 164, C.I. Basic Green 1 through 14, C.I. Basic Brown 1 through 23, CI Basic Black 1 through 11, and a clay selected from the group consisting of Montmorillonite clay, Hectorite clay, Saponite clay and mixtures thereof. In still another aspect, suitable dye clay conjugates include dye clay conjugates selected from the group consisting of: Montmorillonite Basic Blue B7 C.I. 42595 conjugate, Montmorillonite Basic Blue B9 C.I. 52015 conjugate, Montmorillonite Basic Violet V3 C.I. 42555 conjugate, Montmorillonite Basic Green G1 C.I. 42040 conjugate, Montmorillonite Basic Red R1 C.I. 45160 conjugate, Montmorillonite C.I. Basic Black 2 conjugate, Hectorite Basic Blue B7 C.I. 42595 conjugate, Hectorite Basic Blue B9 C.I. 52015 conjugate, Hectorite Basic Violet V3 C.I. 42555 conjugate, Hectorite Basic Green G1 C.I. 42040 conjugate, Hectorite Basic Red R1 C.I. 45160 conjugate, Hectorite C.I. Basic Black 2 conjugate, Saponite Basic Blue B7 C.I. 42595 conjugate, Saponite Basic Blue B9 C.I. 52015 conjugate, Saponite Basic Violet V3 C.I. 42555 conjugate, Saponite Basic Green G1 C.I. 42040 conjugate, Saponite Basic Red R1 C.I. 45160 conjugate, Saponite C.I. Basic Black 2 conjugate and mixtures thereof.

Suitable pigments include pigments selected from the group consisting of flavanthrone, indanthrone, chlorinated indanthrone containing from 1 to 4 chlorine atoms, pyranthrone, dichloropyranthrone, monobromodichloropyranthrone, dibromodichloropyranthrone, tetrabromopyranthrone, perylene-3,4,9,10-tetracarboxylic acid diimide, wherein the imide groups may be unsubstituted or substituted by C1-C3-alkyl or a phenyl or heterocyclic radical, and wherein the phenyl and heterocyclic radicals may additionally carry substituents which do not confer solubility in water, anthrapyrimidinecarboxylic acid amides, violanthrone, isoviolanthrone, dioxazine pigments, copper phthalocyanine which may contain up to 2 chlorine atoms per molecule, polychloro-copper phthalocyanine or polybromochloro-copper phthalocyanine containing up to 14 bromine atoms per molecule and mixtures thereof.

In another aspect, suitable pigments include pigments selected from the group consisting of Ultramarine Blue (CI Pigment Blue 29), Ultramarine Violet (CI Pigment Violet 15) and mixtures thereof.

The aforementioned fabric hueing agents can be used in combination (any mixture of fabric hueing agents can be used). Suitable hueing agents are described in more detail in U.S. Pat. No. 7,208,459. Preferred levels of dye in compositions of the invention are 0.00001 to 0.5 wt %, or 0.0001 to 0.25 wt %. The concentration of dyes preferred in water for the treatment and/or cleaning step is from 1 ppb to 5 ppm, 10 ppb to 5 ppm or 20 ppb to 5 ppm. In preferred compositions, the concentration of surfactant will be from 0.2 to 3 g/l.

Encapsulates

The composition may comprise an encapsulate. In one aspect, an encapsulate comprising a core, a shell having an inner and outer surface, said shell encapsulating said core.

In one aspect of said encapsulate, said core may comprise a material selected from the group consisting of perfumes; brighteners; dyes; insect repellants; silicones; waxes; flavors; vitamins; fabric softening agents; skin care agents in one aspect, paraffins; enzymes; anti-bacterial agents; bleaches; sensates; and mixtures thereof; and said shell may comprise a material selected from the group consisting of polyethylenes; polyamides; polyvinylalcohols, optionally containing other co-monomers; polystyrenes; polyisoprenes; polycarbonates; polyesters; polyacrylates; aminoplasts, in one aspect said aminoplast may comprise a polyureas, polyurethane, and/or polyureaurethane, in one aspect said polyurea may comprise polyoxymethyleneurea and/or melamine formaldehyde; polyolefins; polysaccharides, in one aspect said polysaccharide may comprise alginate and/or chitosan; gelatin; shellac; epoxy resins; vinyl polymers; water insoluble inorganics; silicone; and mixtures thereof.

In one aspect of said encapsulate, said core may comprise perfume.

In one aspect of said encapsulate, said shell may comprise melamine formaldehyde and/or cross linked melamine formaldehyde.

In a one aspect, suitable encapsulates may comprise a core material and a shell, said shell at least partially surrounding said core material, is disclosed. 85% or 90% of said encapsulates may have a fracture strength of from 0.2 to 10 MPa, from 0.4 to 5 MPa, from 0.6 to 3.5 MPa, or from 0.7 to 3 MPa; and a benefit agent leakage of from 0 to 30%, from 0 to 20%, or from 0 to 5%.

In one aspect, 85% or 90% of said encapsulates may have a particle size from 1 to 80 microns, from 5 to 60 microns, from 10 to 50 microns, or from 15 to 40 microns. In one aspect, 85% or 90% of said encapsulates may have a particle wall thickness from 30 to 250 nm, from 80 to 180 nm, or from 100 to 160 nm.

In one aspect, said encapsulates' core material may comprise a material selected from the group consisting of a perfume raw material and/or optionally a material selected from the group consisting of vegetable oil, including neat and/or blended vegetable oils including castor oil, coconut oil, cottonseed oil, grape oil, rapeseed, soybean oil, corn oil, palm oil, linseed oil, safflower oil, olive oil, peanut oil, coconut oil, palm kernel oil, castor oil, lemon oil and mixtures thereof; esters of vegetable oils, esters, including dibutyl adipate, dibutyl phthalate, butyl benzyl adipate, benzyl octyl adipate, tricresyl phosphate, trioctyl phosphate and mixtures thereof; straight or branched chain hydrocarbons, including those straight or branched chain hydrocarbons having a boiling point of greater than about 80° C.; partially hydrogenated terphenyls, dialkyl phthalates, alkyl biphenyls, including monoisopropylbiphenyl, alkylated naphthalene, including dipropylnaphthalene, petroleum spirits, including kerosene, mineral oil and mixtures thereof; aromatic solvents, including benzene, toluene and mixtures thereof; silicone oils; and mixtures thereof.

In one aspect, said encapsulates' wall material may comprise a suitable resin including the reaction product of an aldehyde and an amine, suitable aldehydes include, formaldehyde. Suitable amines include melamine, urea, benzoguanamine, glycoluril, and mixtures thereof.

Suitable melamines include methylol melamine, methylated methylol melamine, imino melamine and mixtures thereof. Suitable ureas include dimethylol urea, methylated dimethylol urea, urea-resorcinol, and mixtures thereof.

In one aspect, suitable formaldehyde scavengers may be employed with the encapsulates e.g. in a capsule slurry and/or added to a composition before, during or after the encapsulates are added to such composition. Suitable capsules may be made by the following teaching of US2008/0305982; and/or US2009/0247449.

In a preferred aspect the composition can also comprise a deposition aid, preferably consisting of the group comprising cationic or nonionic polymers. Suitable polymers include cationic starches, cationic hydroxyethylcellulose, polyvinylformaldehyde, locust bean gum, mannans, xyloglucans, tamarind gum, polyethyleneterephthalate and polymers containing dimethylaminoethyl methacrylate, optionally with one or monomers selected from the group comprising acrylic acid and acrylamide.

Perfumes

In one aspect the composition comprises a perfume that comprises one or more perfume raw materials selected from the group consisting of 1,1'-oxybis-2-propanol; 1,4-cyclohexanedicarboxylic acid, diethyl ester; (ethoxymethoxy)cyclododecane; 1,3-nonanediol, monoacetate; (3-methylbutoxy)acetic acid, 2-propenyl ester; beta-methyl cyclododecaneethanol; 2-methyl-3-[(1,7,7-trimethylbicyclo[2.2.1]hept-2-ypoxy]-1-propanol; oxacyclohexadecan-2-one; alpha-methyl-benzenemethanol acetate; trans-3-ethoxy-1,1,5-trimethylcyclohexane; 4-(1,1-dimethylethyl)cyclohexanol acetate; dodecahydro-3a,6,6,9a-tetramethylnaphtho[2,1-b]furan; beta-methyl benzenepropanal; beta-methyl-3-(1-methylethyl)benzenepropanal; 4-phenyl-2-butanone; 2-methylbutanoic acid, ethyl ester; benzaldehyde; 2-methylbutanoic acid, 1-methylethyl ester; dihydro-5-pentyl-2(3H)furanone; (2E)-1-(2,6,6-trimethyl-2-cyclohexen-1-yl)-2-buten-1-one; dodecanal; undecanal; 2-ethyl-alpha, alpha-dimethylbenzenepropanal; decanal; alpha, alpha-dimethylbenzeneethanol acetate; 2-(phenylmethylene)octanal; 2-[[3-[4-(1,1-dimethylethyl)phenyl]-2-methylpropylidene]amino]benzoic acid, methyl ester; 1-(2,6,6-trimethyl-3-cyclohexen-1-yl)-2-buten-1-one; 2-pentylcyclopentanone; 3-oxo-2-pentyl cyclopentaneacetic acid, methyl ester; 4-hydroxy-3-methoxybenzaldehyde; 3-ethoxy-4-hydroxybenzaldehyde; 2-heptylcyclopentanone; 1-(4-methylphenyl)ethanone; (3E)-4-(2,6,6-trimethyl-1-cyclohexen-1-yl)-3-buten-2-one; (3E)-4-(2,6,6-trimethyl-2-cyclohexen-1-yl)-3-buten-2-one; benzeneethanol; 2H-1-benzopyran-2-one; 4-methoxybenzaldehyde; 10-undecenal; propanoic acid, phenylmethyl ester; beta-methylbenzenepentanol; 1,1-diethoxy-3,7-dimethyl-2,6-octadiene; alpha, alpha-dimethylbenzeneethanol; (2E)-1-(2,6,6-trimethyl-1-cyclohexen-1-yl)-2-buten-1-one; acetic acid, phenylmethyl ester; cyclohexanepropanoic acid, 2-propenyl ester; hexanoic acid, 2-propenyl ester; 1,2-dimethoxy-4-(2-propenyl)benzene; 1,5-dimethyl-bicyclo[3.2.1]octan-8-one oxime; 4-(4-hydroxy-4-methylpentyl)-3-cyclohexene-1-carboxaldehyde; 3-buten-2-ol; 2-[[[2,4(or 3,5)-dimethyl-3-cyclohexen-1-yl]methylene]amino]benzoic acid, methyl ester; 8-cyclohexadecen-1-one; methyl ionone; 2,6-dimethyl-7-octen-2-ol; 2-methoxy-4-(2-propenyl)phenol; (2E)-3,7-dimethyl-2,6-Octadien-1-ol; 2-hydroxy-Benzoic acid, (3Z)-3-hexenyl ester; 2-tridecenenitrile; 4-(2,2-dimethyl-6-methylenecyclohexyl)-3-methyl-3-buten-2-one; tetrahydro-4-methyl-2-(2-methyl-1-propenyl)-2H-pyran; Acetic acid, (2-methylbutoxy)-, 2-propenyl ester; Benzoic acid, 2-hydroxy-, 3-methylbutyl ester; 2-Buten-1-one, 1-(2,6,6-trimethyl-1-cyclohexen-1-yl)-, (Z)—; Cyclopentanecarboxylic acid, 2-hexyl-3-oxo-, methyl ester; Benzenepropanal, 4-ethyl-.alpha.,.alpha.-dimethyl-; 3-Cyclohexene-1-carboxaldehyde, 3-(4-hydroxy-4-methylpentyl)-; Ethanone, 1-(2,3,4,7,8,8a-hexahydro-3,6,8,8-tetramethyl-1H-3a,7-methanoazulen-5-yl)-, [3R-(3.alpha.,3a.beta.,7.beta.,8a.alpha.)]-; Undecanal, 2-methyl-2H-Pyran-2-one, 6-butyltetrahydro-; Benzenepropanal, 4-(1,1-dimethylethyl)-.alpha.-methyl-; 2(3H)-Furanone, 5-heptyldihydro-; Benzoic acid, 2-[(7-hydroxy-3,7-dimethyloctylidene)amino]-, methyl; Benzoic acid, 2-hydroxy-, phenylmethyl ester; Naphthalene, 2-methoxy-; 2-Cyclopenten-1-one, 2-hexyl-; 2(3H)-Furanone, 5-hexyldihydro-; Oxiranecarboxylic acid, 3-methyl-3-phenyl-, ethyl ester; 2-Oxabicyclo[2.2.2]octane, 1,3,3-trimethyl-; Benzenepentanol, .gamma.-methyl-; 3-Octanol, 3,7-dimethyl-; 3,7-dimethyl-2,6-octadienenitrile; 3,7-dimethyl-6-octen-1-ol; Terpineol acetate; 2-methyl-6-methylene-7-Octen-2-ol, dihydro derivative; 3a,4,5,6,7,7a-hexahydro-4,7-Methano-1H-inden-6-ol propanoate; 3-methyl-2-buten-1-ol acetate; (Z)-3-Hexen-1-ol acetate; 2-ethyl-4-(2,2,3-trimethyl-3-cyclopenten-1-yl)-2-buten-1-ol; 4-(octahydro-4,7-methano-5H-inden-5-ylidene)-butanal; 3-2,4-dimethyl-cyclohexene-1-carboxaldehyde; 1-(1,2,3,4,5,6,7,8-octahydro-2,3,8,8-tetramethyl-2-naphthalenyl)-ethanone; 2-hydroxy-benzoic acid, methyl ester; 2-hydroxy-benzoic acid, hexyl ester; 2-phenoxy-ethanol; 2-hydroxy-benzoic acid, pentyl ester; 2,3-heptanedione; 2-hexen-1-ol; 6-Octen-2-ol, 2,6-dimethyl-; damascone (alpha, beta, gamma or delta or mixtures thereof), 4,7-Methano-1H-inden-6-ol, 3a,4,5,6,7,7a-hexahydro-, acetate; 9-Undecenal; 8-Undecenal; Isocyclocitral; Ethanone, 1-(1,2,3,5,6,7,8,8a-octahydro-2,3,8,8-tetramethyl-2-naphthalenyl)-; 3-Cyclohexene-1-carboxaldehyde, 3,5-dimethyl-; 3-Cyclohexene-1-carboxaldehyde, 2,4-dimethyl-; 1,6-Octadien-3-ol, 3,7-dimethyl-; 1,6-Octadien-3-ol, 3,7-dimethyl-, acetate; Lilial (p-t-Bucinal), and Cyclopentanone, 2-[2-(4-methyl-3-cyclohexen-1-yl)propyl]- and 1-methyl-4-(1-methylethenyl)cyclohexene and mixtures thereof.

In one aspect the composition may comprise an encapsulated perfume particle comprising either a water-soluble hydroxylic compound or melamine-formaldehyde or modified polyvinyl alcohol. In one aspect the encapsulate comprises (a) an at least partially water-soluble solid matrix comprising one or more water-soluble hydroxylic compounds, preferably starch; and (b) a perfume oil encapsulated by the solid matrix.

In a further aspect the perfume may be pre-complexed with a polyamine, preferably a polyethylenimine so as to form a Schiff base.

Polymers

The composition may comprise one or more polymers. Examples are carboxymethylcellulose, poly(vinyl-pyrrolidone), poly (ethylene glycol), poly(vinyl alcohol), poly (vinylpyridine-N-oxide), poly(vinylimidazole), polycarboxylates such as polyacrylates, maleic/acrylic acid copolymers and lauryl methacrylate/acrylic acid co-polymers.

The composition may comprise one or more amphiphilic cleaning polymers such as the compound having the following general structure: bis(($C_2H_5O$)($C_2H_4O$)n)($CH_3$)—$N^+$—$C_xH_{2x}$—$N^+$—($CH_3$)-bis(($C_2H_5O$)($C_2H_4O$)n), wherein n=from 20 to 30, and x=from 3 to 8, or sulphated or sulphonated variants thereof.

The composition may comprise amphiphilic alkoxylated grease cleaning polymers which have balanced hydrophilic and hydrophobic properties such that they remove grease particles from fabrics and surfaces. Specific embodiments of the amphiphilic alkoxylated grease cleaning polymers of the present invention comprise a core structure and a plurality of alkoxylate groups attached to that core structure. These may comprise alkoxylated polyalkylenimines, preferably having an inner polyethylene oxide block and an outer polypropylene oxide block.

Alkoxylated polycarboxylates such as those prepared from polyacrylates are useful herein to provide additional grease removal performance. Such materials are described in WO91/08281 and PCT90/01815. Chemically, these materials comprise polyacrylates having one ethoxy side-chain per every 7-8 acrylate units. The side-chains are of the formula —$(CH_2CH_2O)_m(CH_2)_nCH_3$ wherein m is 2-3 and n is 6-12. The side-chains are ester-linked to the polyacrylate "backbone" to provide a "comb" polymer type structure. The molecular weight can vary, but is typically in the range of 2000 to 50,000. Such alkoxylated polycarboxylates can comprise from 0.05 wt % to 10 wt % of the compositions herein.

The isoprenoid-derived surfactants of the present invention, and their mixtures with other cosurfactants and other adjunct ingredients, are particularly suited to be used with an amphilic graft co-polymer, preferably the amphilic graft co-polymer comprises (i) polyethyelene glycol backbone; and (ii) and at least one pendant moiety selected from polyvinyl acetate, polyvinyl alcohol and mixtures thereof. A preferred amphilic graft co-polymer is Sokalan HP22, supplied from BASF. Suitable polymers include random graft copolymers, preferably a polyvinyl acetate grafted polyethylene oxide copolymer having a polyethylene oxide backbone and multiple polyvinyl acetate side chains. The molecular weight of the polyethylene oxide backbone is preferably 6000 and the weight ratio of the polyethylene oxide to polyvinyl acetate is 40 to 60 and no more than 1 grafting point per 50 ethylene oxide units.

Carboxylate Polymer

The composition of the present invention may also include one or more carboxylate polymers such as a maleate/acrylate random copolymer or polyacrylate homopolymer. In one aspect, the carboxylate polymer is a polyacrylate homopolymer having a molecular weight of from 4,000 to 9,000 Da, or from 6,000 to 9,000 Da.

Soil Release Polymer

The composition of the present invention may also include one or more soil release polymers having a structure as defined by one of the following structures (I), (II) or (III):

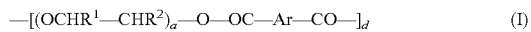   (I)

   (II)

   (III)

wherein:
a, b and c are from 1 to 200;
d, e and f are from 1 to 50;
Ar is a 1,4-substituted phenylene;
sAr is 1,3-substituted phenylene substituted in position 5 with $SO_3Me$;
Me is Li, K, Mg/2, Ca/2, Al/3, ammonium, mono-, di-, tri-, or tetraalkylammonium wherein the alkyl groups are $C_1$-$C_{18}$ alkyl or $C_2$-$C_{10}$ hydroxyalkyl, or mixtures thereof;
$R^1$, $R^2$, $R^3$, $R^4$, $R^5$ and $R^6$ are independently selected from H or $C_1$-$C_{18}$ n- or iso-alkyl; and $R^7$ is a linear or branched $C_1$-$C_{18}$ alkyl, or a linear or branched $C_2$-$C_{30}$ alkenyl, or a cycloalkyl group with 5 to 9 carbon atoms, or a $C_8$-$C_{30}$ aryl group, or a $C_6$-$C_{30}$ arylalkyl group.

Suitable soil release polymers are polyester soil release polymers such as Repel-o-tex polymers, including Repel-o-tex, SF-2 and SRP6 supplied by Rhodia. Other suitable soil release polymers include Texcare polymers, including Texcare SRA100, SRA300, SRN100, SRN170, SRN240, SRN300 and SRN325 supplied by Clariant. Other suitable soil release polymers are Marloquest polymers, such as Marloquest SL supplied by Sasol.

Cellulosic Polymer

The composition of the present invention may also include one or more cellulosic polymers including those selected from alkyl cellulose, alkyl alkoxyalkyl cellulose, carboxyalkyl cellulose, alkyl carboxyalkyl cellulose. In one aspect, the cellulosic polymers are selected from the group comprising carboxymethyl cellulose, methyl cellulose, methyl hydroxyethyl cellulose, methyl carboxymethyl cellulose, and mixtures thereof. In one aspect, the carboxymethyl cellulose has a degree of carboxymethyl substitution from 0.5 to 0.9 and a molecular weight from 100,000 to 300,000 Da.

Enzymes

The composition may comprise one or more enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, malanases, R-glucanases, arabinosidases, hyaluronidase, chondroitinase, laccase, chlorophyllases and amylases, or mixtures thereof. A typical combination is an enzyme cocktail that may comprise e.g. a protease and lipase in conjunction with amylase. When present in a composition, the aforementioned additional enzymes may be present at levels from 0.00001 to 2 wt %, from 0.0001 to 1 wt % or from 0.001 to 0.5 wt % enzyme protein by weight of the composition.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO99/001544.

Other cellulases are endo-beta-1,4-glucanase enzyme having a sequence of at least 97% identity to the amino acid sequence of position 1 to position 773 of SEQ ID NO:2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes A/S) Carezyme Premium™ (Novozymes A/S), Celluclean™ (Novozymes A/S), Celluclean Classic™ (Novozymes A/S), Cellusoft™ (Novozymes A/S), Whitezyme™ (Novozymes A/S), Clazinase™, and Puradax HA™ (Genencor International Inc.), and KAC-500(B)™ (Kao Corporation).

Proteases

Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those obtained from Bacillus such as Bacillus lentus, B. alkalophilus, B. subtilis, B. amyloliquefaciens, Bacillus pumilus and Bacillus gibsonii described in; U.S. Pat. No. 7,262,042 and WO09/021867, and subtilisin lentus, subtilisin Novo, subtilisin Carlsberg, Bacillus licheniformis, subtilisin BPN', subtilisin 309, subtilisin 147 and subtilisin 168 described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the Fusarium protease described in WO89/06270, WO94/25583 and WO05/040372, and the chymotrypsin proteases obtained from Cellumonas described in WO05/052161 and WO05/052146.

A further preferred protease is the alkaline protease from Bacillus lentus DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Genencor Int.) such as those obtained from Bacillus amyloliquefaciens.

Examples of useful proteases are the variants described in: WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 27, 36, 57, 68, 76, 87, 95, 96, 97, 98, 99, 100, 101, 102, 103, 104, 106, 118, 120, 123, 128, 129, 130, 160, 167, 170, 194, 195, 199, 205, 206, 217, 218, 222, 224, 232, 235, 236, 245, 248, 252 and 274 using the BPN' numbering. More preferred the subtilase variants may comprise the mutations: S3T, V41, S9R, A15T, K27R, *36D, V68A, N76D, N87S,R, *97E, A98S, S99G,D,A, S99AD, S101G,M,R S103A, V104I,Y,N, S106A, G118V,R, H120D,N, N123S, S128L, P129Q, S130A, G160D, Y167A, R170S, A194P, G195E, V199M, V205I, L217D, N218D, M222S, A232V, K235L, Q236H, Q245R, N252K, T274A (using BPN' numbering).

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Neutrase®, Everlase® and Esperase® (Novozymes NS), those sold under the tradename Maxatase®, Maxacal®, Maxapem®, Purafect®, Purafect Prime®, Preferenz™, Purafect MA®, Purafect Ox®, Purafect OxP®, Puramax®, Properase®, Effectenz™, FN2®, FN3®, FN4®, Excellase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (Bacillus alkalophilus subtilisin) from Kao.

Lipases and Cutinases

Suitable lipases and cutinases include those of bacterial or fungal origin. Chemically modified or protein engineered mutant enzymes are included. Examples include lipase from Thermomyces, e.g. from T. lanuginosus (previously named Humicola lanuginosa) as described in EP258068 and EP305216, cutinase from Humicola, e.g. H. insolens (WO96/13580), lipase from strains of Pseudomonas (some of these now renamed to Burkholderia), e.g. P. alcaligenes or P. pseudoalcaligenes (EP218272), P. cepacia (EP331376), P. sp. strain SD705 (WO95/06720 & WO96/27002), P. wisconsinensis (WO96/12012), GDSL-type Streptomyces lipases (WO10/065455), cutinase from Magnaporthe grisea (WO10/107560), cutinase from Pseudomonas mendocina (U.S. Pat. No. 5,389,536), lipase from Thermobifida fusca (WO11/084412), Geobacillus stearothermophilus lipase (WO11/084417), lipase from Bacillus subtilis (WO11/084599), and lipase from Streptomyces griseus (WO11/150157) and S. pristinaespiralis (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g. acyltransferases with homology to Candida antarctica lipase A (WO10/111143), acyltransferase from Mycobacterium smegmatis (WO05/56782), perhydrolases from the CE 7 family (WO09/67279), and variants of the M. smegmatis perhydrolase in particular the S54V variant used in the commercial product Gentle Power Bleach from Huntsman Textile Effects Pte Ltd (WO10/100028).

Amylases

Suitable amylases which can be used together with the enzyme of the invention may be an alpha-amylase or a glucoamylase and may be of bacterial or fungal origin. Chemically modified or protein engineered mutants are included. Amylases include, for example, alpha-amylases obtained from Bacillus, e.g., a special strain of Bacillus licheniformis, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase obtained from B. amyloliquefaciens shown in SEQ ID NO: 6 of WO 2006/066594 and residues 36-483 of the B. licheniformis alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase obtained from B. amyloliquefaciens shown in SEQ ID NO: 6 of WO 2006/066594 and residues 36-483 of SEQ ID NO: 4 are those having the substitutions:

M197T;
H156Y+A181T+N190F+A209V+Q264S; or
G48A+T491+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one or more of the following positions: Q87, Q98, S125, N128, T131, T165, K178, R180, S181, T182, G183, M201, F202, N225, S243, N272, N282, Y305, R309, D319, Q320, O359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E, R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;
N128C+K178L+I182G+F202Y+Y305R+D319T+G475K;
S125A+N128C+K178L+T182G+Y305R+G475K; or
S125A+N128C+T131I+T165I+K178L+T182G+Y305R+G475K, wherein the variants are C-terminally truncated and optionally further comprises a substitution at position 243 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase and Preferenz S100 (from Genencor International Inc./DuPont).

Other Enzymes

In one aspect, other preferred enzymes include microbial-derived endoglucanases exhibiting endo-beta-1,4-glucanase activity (EC3.2.1.4), including a bacterial polypeptide endogenous to a member of the genus Bacillus which has a sequence of at least 90%, 91%, 92%, 93%, 94%, 95%, 96%, 97%, 98%, 99% or 100% identity to the amino acid sequence SEQ ID NO:2 in U.S. Pat. No. 7,141,403 and mixtures thereof. Suitable endoglucanases are sold under the tradenames Celluclean® and Whitezyme® (Novozymes).

Other preferred enzymes include pectate lyases sold under the tradenames Pectawash®, Pectaway®, Xpect® and mannanases sold under the tradenames Mannaway® (Novozymes), and Purabrite® (Danisco/Dupont).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g. as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP238216.

Dye Transfer Inhibiting Agents

The compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a composition, the dye transfer inhibiting agents may be present at levels from 0.0001 to 10 wt %, from 0.01 to 5 wt % or from 0.1 to 3 wt %.

Brighteners

The compositions of the present invention can also contain additional components that may tint articles being cleaned, such as fluorescent brighteners.

The composition may comprise C.I. fluorescent brightener 260 in alpha-crystalline form having the following structure:

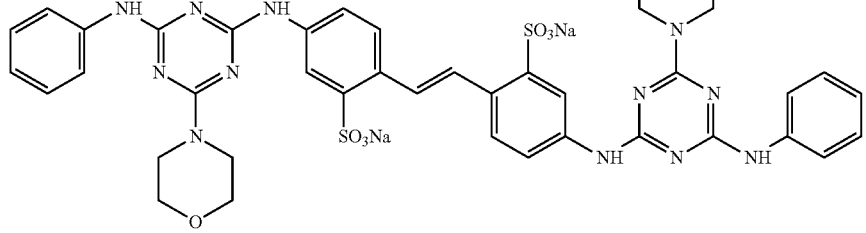

In one aspect, the brightener is a cold water soluble brightener, such as the C.I. fluorescent brightener 260 in alpha-crystalline form. In one aspect the brightener is predominantly in alpha-crystalline form, which means that typically at least 50 wt %, at least 75 wt %, at least 90 wt %, at least 99 wt %, or even substantially all, of the C.I. fluorescent brightener 260 is in alpha-crystalline form.

The brightener is typically in micronized particulate form, having a weight average primary particle size of from 3 to 30 micrometers, from 3 micrometers to 20 micrometers, or from 3 to 10 micrometers.

The composition may comprise C.I. fluorescent brightener 260 in beta-crystalline form, and the weight ratio of: (i) C.I. fluorescent brightener 260 in alpha-crystalline form, to (ii) C.I. fluorescent brightener 260 in beta-crystalline form may be at least 0.1, or at least 0.6. BE680847 relates to a process for making C.I fluorescent brightener 260 in alpha-crystalline form.

Commercial optical brighteners which may be useful in the present invention can be classified into subgroups, which include, but are not necessarily limited to, derivatives of stilbene, pyrazoline, coumarin, carboxylic acid, methinecyanines, dibenzothiophene-5,5-dioxide, azoles, 5- and 6-membered-ring heterocycles, and other miscellaneous agents. Examples of such brighteners are disclosed in "The Production and Application of Fluorescent Brightening Agents", M. Zahradnik, Published by John Wiley & Sons, New York (1982). Specific nonlimiting examples of optical brighteners which are useful in the present compositions are those identified in U.S. Pat. Nos. 4,790,856 and 3,646,015.

A further suitable brightener has the structure below:

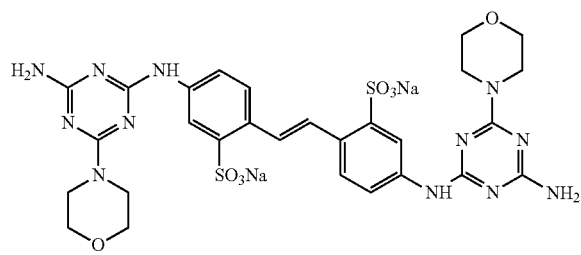

Suitable fluorescent brightener levels include lower levels of from 0.01 wt %, from 0.05 wt %, from 0.1 wt % or from 0.2 wt % to upper levels of 0.5 wt % or 0.75 wt %.

In one aspect the brightener may be loaded onto a clay to form a particle. Silicate salts—The compositions of the present invention can also contain silicate salts, such as sodium or potassium silicate. The composition may comprise of from 0 wt % to less than 10 wt % silicate salt, to 9 wt %, or to 8 wt %, or to 7 wt %, or to 6 wt %, or to 5 wt %, or to 4 wt %, or to 3 wt %, or even to 2 wt %, and from above 0 wt %, or from 0.5 wt %, or from 1 wt % silicate salt. A suitable silicate salt is sodium silicate.

Dispersants

The compositions of the present invention can also contain dispersants. Suitable water-soluble organic materials include the homo- or co-polymeric acids or their salts, in which the polycarboxylic acid comprises at least two carboxyl radicals separated from each other by not more than two carbon atoms.

Enzyme Stabilizers

Enzymes for use in compositions can be stabilized by various techniques. The enzymes employed herein can be stabilized by the presence of water-soluble sources of calcium and/or magnesium ions. Examples of conventional stabilizing agents are, e.g. a polyol such as propylene glycol or glycerol, a sugar or sugar alcohol, lactic acid, boric acid, or a boric acid derivative, e.g. an aromatic borate ester, or a phenyl boronic acid derivative such as 4-formylphenyl boronic acid, and the composition may be formulated as described in, for example, WO92/19709 and WO92/19708 In case of aqueous compositions comprising protease, a reversible protease inhibitor, such as a boron compound including borate, 4-formyl phenylboronic acid, phenylboronic acid and derivatives thereof, or compounds such as calcium formate, sodium formate and 1,2-propane diol can be added to further improve stability.

Solvents

Suitable solvents include water and other solvents such as lipophilic fluids. Examples of suitable lipophilic fluids include siloxanes, other silicones, hydrocarbons, glycol ethers, glycerine derivatives such as glycerine ethers, perfluorinated amines, perfluorinated and hydrofluoroether solvents, low-volatility nonfluorinated organic solvents, diol solvents, other environmentally-friendly solvents and mixtures thereof.

Structurant/Thickeners

Structured liquids can either be internally structured, whereby the structure is formed by primary ingredients (e.g. surfactant material) and/or externally structured by providing a three dimensional matrix structure using secondary ingredients (e.g. polymers, clay and/or silicate material). The composition may comprise a structurant, from 0.01 to 5 wt %, or from 0.1 to 2.0 wt %. The structurant is typically selected from the group consisting of diglycerides and triglycerides, ethylene glycol distearate, microcrystalline cellulose, cellulose-based materials, microfiber cellulose, hydrophobically modified alkali-swellable emulsions such as Polygel W30 (3VSigma), biopolymers, xanthan gum, gellan gum, and mixtures thereof. A suitable structurant includes hydrogenated castor oil, and non-ethoxylated derivatives thereof. A suitable structurant is disclosed in U.S. Pat. No. 6,855,680. Such structurants have a thread-like structuring system having a range of aspect ratios. Other suitable structurants and the processes for making them are described in WO10/034736.

Conditioning Agents

The composition of the present invention may include a high melting point fatty compound. The high melting point fatty compound useful herein has a melting point of 25° C. or higher, and is selected from the group consisting of fatty alcohols, fatty acids, fatty alcohol derivatives, fatty acid derivatives, and mixtures thereof. Such compounds of low melting point are not intended to be included in this section. Non-limiting examples of the high melting point compounds are found in International Cosmetic Ingredient Dictionary, Fifth Edition, 1993, and CTFA Cosmetic Ingredient Handbook, Second Edition, 1992.

The high melting point fatty compound is included in the composition at a level of from 0.1 to 40 wt %, from 1 to 30 wt %, from 1.5 to 16 wt %, from 1.5 to 8 wt % in view of providing improved conditioning benefits such as slippery feel during the application to wet hair, softness and moisturized feel on dry hair.

The compositions of the present invention may contain a cationic polymer. Concentrations of the cationic polymer in the composition typically range from 0.05 to 3 wt %, from 0.075 to 2.0 wt %, or from 0.1 to 1.0 wt %. Suitable cationic polymers will have cationic charge densities of at least 0.5 meq/gm, at least 0.9 meq/gm, at least 1.2 meq/gm, at least 1.5 meq/gm, or less than 7 meq/gm, and less than 5 meq/gm, at the pH of intended use of the composition, which pH will generally range from pH 3 to pH 9, or between pH 4 and pH 8. Herein, "cationic charge density" of a polymer refers to the ratio of the number of positive charges on the polymer to the molecular weight of the polymer. The average molecular weight of such suitable cationic polymers will generally be between 10,000 and 10 million, between 50,000 and 5 million, or between 100,000 and 3 million.

Suitable cationic polymers for use in the compositions of the present invention contain cationic nitrogen-containing moieties such as quaternary ammonium or cationic protonated amino moieties. Any anionic counterions can be used in association with the cationic polymers so long as the polymers remain soluble in water, in the composition, or in a coacervate phase of the composition, and so long as the counterions are physically and chemically compatible with the essential components of the composition or do not otherwise unduly impair composition performance, stability or aesthetics. Nonlimiting examples of such counterions include halides (e.g., chloride, fluoride, bromide, iodide), sulfate and methylsulfate.

Nonlimiting examples of such polymers are described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)).

Other suitable cationic polymers for use in the composition include polysaccharide polymers, cationic guar gum derivatives, quaternary nitrogen-containing cellulose ethers, synthetic polymers, copolymers of etherified cellulose, guar and starch. When used, the cationic polymers herein are either soluble in the composition or are soluble in a complex coacervate phase in the composition formed by the cationic polymer and the anionic, amphoteric and/or zwitterionic surfactant component described hereinbefore. Complex coacervates of the cationic polymer can also be formed with other charged materials in the composition. Suitable cationic polymers are described in U.S. Pat. Nos. 3,962,418; 3,958,581; and US2007/0207109. The composition of the present invention may include a nonionic polymer as a conditioning agent. Polyalkylene glycols having a molecular weight of more than 1000 are useful herein. Useful are those having the following general formula:

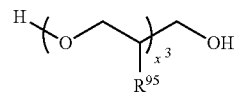

wherein $R^{95}$ is selected from the group consisting of H, methyl, and mixtures thereof. Conditioning agents, and in particular silicones, may be included in the composition. The conditioning agents useful in the compositions of the present invention typically comprise a water insoluble, water dispersible, non-volatile, liquid that forms emulsified, liquid particles. Suitable conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein. Such conditioning agents should be physically and chemically compatible with the essential components of the composition, and should not otherwise unduly impair composition stability, aesthetics or performance.

The concentration of the conditioning agent in the composition should be sufficient to provide the desired conditioning benefits. Such concentration can vary with the conditioning agent, the conditioning performance desired, the average size of the conditioning agent particles, the type and concentration of other components, and other like factors.

The concentration of the silicone conditioning agent typically ranges from 0.01 to 10 wt %. Non-limiting examples of suitable silicone conditioning agents, and optional suspending agents for the silicone, are described in U.S. Reissue Pat. No. 34,584; U.S. Pat. Nos. 5,104,646; 5,106,609; 4,152,416; 2,826,551; 3,964,500; 4,364,837; 6,607,717; 6,482,969; 5,807,956; 5,981,681; 6,207,782; 7,465,439; 7,041,767; 7,217,777; US2007/0286837A1; US2005/0048549A1; US2007/0041929A1; GB849433; DE10036533, which are all incorporated herein by reference; Chemistry and Technology of Silicones, New York: Academic Press (1968); General Electric Silicone Rubber Product Data Sheets SE 30, SE 33, SE 54 and SE 76; Silicon Compounds, Petrarch Systems, Inc. (1984); and in Encyclopedia of Polymer Science and Engineering, vol. 15, 2d ed., pp 204-308, John Wiley & Sons, Inc. (1989).

The compositions of the present invention may also comprise from 0.05 to 3 wt % of at least one organic conditioning oil as the conditioning agent, either alone or in combination with other conditioning agents, such as the silicones (described herein). Suitable conditioning oils include hydrocarbon oils, polyolefins, and fatty esters. Also suitable for use in the compositions herein are the conditioning agents described in U.S. Pat. Nos. 5,674,478 and 5,750,122 or in U.S. Pat. Nos. 4,529,586; 4,507,280; 4,663,158; 4,197,865; 4,217,914; 4,381,919; and 4,422,853.

Hygiene and Malodour

The compositions of the present invention may also comprise one or more of zinc ricinoleate, thymol, quaternary ammonium salts such as Bardac®, polyethylenimines (such as Lupasol® from BASF) and zinc complexes thereof, silver and silver compounds, especially those designed to slowly release Ag$^+$ or nano-silver dispersions.

Probiotics

The compositions may comprise probiotics such as those described in WO09/043709.

Suds Boosters

If high sudsing is desired, suds boosters such as the $C_{10}$-$C_{16}$ alkanolamides or $C_{10}$-$C_{14}$ alkyl sulphates can be incorporated into the compositions, typically at 1 to 10 wt % levels. The $C_{10}$-$C_{14}$ monoethanol and diethanol amides illustrate a typical class of such suds boosters. Use of such suds boosters with high sudsing adjunct surfactants such as the amine oxides, betaines and sultaines noted above is also advantageous. If desired, water-soluble magnesium and/or calcium salts such as $MgCl_2$, $MgSO_4$, $CaCl_2$, $CaSO_4$ and the like, can be added at levels of, typically, 0.1 to 2 wt %, to provide additional suds and to enhance grease removal performance.

Suds Suppressors

Compounds for reducing or suppressing the formation of suds can be incorporated into the compositions of the present invention. Suds suppression can be of particular importance in the so-called "high concentration cleaning process" as described in U.S. Pat. Nos. 4,489,455 and 4,489,574, and in front-loading-style washing machines. A wide variety of materials may be used as suds suppressors, and suds suppressors are well known to those skilled in the art. See e.g. Kirk Othmer Encyclopedia of Chemical Technology, Third Edition, Volume 7, p. 430-447 (John Wiley & Sons, Inc., 1979). Examples of suds supressors include monocarboxylic fatty acid and soluble salts therein, high molecular weight hydrocarbons such as paraffin, fatty acid esters (e.g., fatty acid triglycerides), fatty acid esters of monovalent alcohols, aliphatic $C_{18}$-$C_{40}$ ketones (e.g., stearone), N-alkylated amino triazines, waxy hydrocarbons preferably having a melting point below about 100° C., silicone suds suppressors, and secondary alcohols. Suds supressors are described in U.S. Pat. Nos. 2,954,347; 4,265,779; 4,265,779; 3,455,839; 3,933,672; 4,652,392; 4,978,471; 4,983,316; 5,288,431; 4,639,489; 4,749,740; 4,798,679; 4,075,118; EP89307851.9; EP150872; and DOS 2,124,526.

For any detergent compositions to be used in automatic laundry washing machines, suds should not form to the extent that they overflow the washing machine. Suds suppressors, when utilized, are preferably present in a "suds suppressing amount". By "suds suppressing amount" is meant that the formulator of the composition can select an amount of this suds controlling agent that will sufficiently control the suds to result in a low-sudsing laundry detergent for use in automatic laundry washing machines.

The compositions herein will generally comprise from 0 to 10 wt % of suds suppressor. When utilized as suds suppressors, monocarboxylic fatty acids, and salts therein, will be present typically in amounts up to 5 wt %. Preferably, from 0.5 to 3 wt % of fatty monocarboxylate suds suppressor is utilized. Silicone suds suppressors are typically utilized in amounts up to 2.0 wt %, although higher amounts may be used. Monostearyl phosphate suds suppressors are generally utilized in amounts ranging from 0.1 to 2 wt %. Hydrocarbon suds suppressors are typically utilized in amounts ranging from 0.01 to 5.0 wt %, although higher levels can be used. The alcohol suds suppressors are typically used at 0.2 to 3 wt %.

The compositions herein may have a cleaning activity over a broad range of pH. In certain embodiments the compositions have cleaning activity from pH4 to pH11.5. In other embodiments, the compositions are active from pH6 to pH11, from pH 7 to pH 11, from pH 8 to pH 11, from pH 9 to pH 11, or from pH 10 to pH 11.5.

The compositions herein may have cleaning activity over a wide range of temperatures, e.g., from 10° C. or lower to 90° C. Preferably the temperature will be below 50° C. or 40° C. or even 30° C. In certain embodiments, the optimum temperature range for the compositions is from 10° C. to 20° C., from 15° C. to 25° C., from 15° C. to 30° C., from 20° C. to 30° C., from 25° C. to 35° C., from 30° C. to 40° C., from 35° C. to 45° C., or from 40° C. to 50° C.

Form of the Composition

The compositions described herein are advantageously employed for example, in laundry applications, hard surface cleaning, dishwashing applications, as well as cosmetic applications such as dentures, teeth, hair and skin. The compositions of the invention are in particular solid or liquid cleaning and/or treatment compositions. In one aspect the invention relates to a composition, wherein the form of the composition is selected from the group consisting of a regular, compact or concentrated liquid; a gel; a paste; a soap bar; a regular or a compacted powder; a granulated solid; a homogenous or a multilayer tablet with two or more layers (same or different phases); a pouch having one or more compartments; a single or a multi-compartment unit dose form; or any combination thereof.

The form of the composition may separate the components physically from each other in compartments such as e.g. water dissolvable pouches or in different layers of tablets. Thereby negative storage interaction between components can be avoided. Different dissolution profiles of each of the compartments can also give rise to delayed dissolution of selected components in the wash solution.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by Mono-Sol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids (US2009/0011970 A1).

Water-Soluble Film—

The compositions of the present invention may also be encapsulated within a water-soluble film. Preferred film materials are preferably polymeric materials. The film material can e.g. be obtained by casting, blow-moulding, extrusion or blown extrusion of the polymeric material, as known in the art. Preferred polymers, copolymers or derivatives thereof suitable for use as pouch material are selected from polyvinyl alcohols, polyvinyl pyrrolidone, polyalkylene oxides, acrylamide, acrylic acid, cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides including starch and gelatine, natural gums such as xanthum and carragum. More preferred polymers are selected from polyacrylates and water-soluble acrylate copolymers, methylcellulose, carboxymethylcellulose sodium, dextrin, ethylcellulose, hydroxyethyl cellulose, hydroxypropyl methylcellulose, maltodextrin, polymethacrylates, and most preferably selected from polyvinyl alcohols, polyvinyl alcohol copolymers and hydroxypropyl methyl cellulose (HPMC), and combinations thereof. Preferably, the level of polymer in the pouch material, e.g. a PVA polymer, is at least 60 wt %. The polymer can have any weight average molecular weight, preferably from about 1.000 to 1.000.000, from about 10.000 to 300.000, from about 20.000 to 150.000. Mixtures of polymers can also be used as the pouch material.

Naturally, different film material and/or films of different thickness may be employed in making the compartments of the present invention. A benefit in selecting different films is that the resulting compartments may exhibit different solubility or release characteristics.

Preferred film materials are PVA films known under the MonoSol trade reference M8630, M8900, H8779 and those described in U.S. Pat. Nos. 6,166,117 and 6,787,512 and PVA films of corresponding solubility and deformability characteristics.

The film material herein can also comprise one or more additive ingredients. For example, it can be beneficial to add plasticisers, e.g. glycerol, ethylene glycol, diethyleneglycol, propylene glycol, sorbitol and mixtures thereof. Other additives include functional detergent additives to be delivered to the wash water, e.g. organic polymeric dispersants, etc.

Processes of Making the Compositions

The compositions of the present invention can be formulated into any suitable form and prepared by any process chosen by the formulator, non-limiting examples of which are described in Applicants' examples and in U.S. Pat. No. 4,990,280; US20030087791A1; US20030087790A1; US20050003983A1; US20040048764A1; U.S. Pat. Nos. 4,762,636; 6,291,412; US20050227891A1; EP1070115A2; U.S. Pat. Nos. 5,879,584; 5,691,297; 5,574,005; 5,569,645; 5,565,422; 5,516,448; 5,489,392; 5,486,303 all of which are incorporated herein by reference. The compositions of the invention or prepared according to the invention comprise cleaning and/or treatment composition including, but not limited to, compositions for treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use: car or carpet shampoos, bathroom cleaners including toilet bowl cleaners; as well as cleaning auxiliaries such as bleach additives and "stain-stick" or pre-treat types, substrate-laden compositions such as dryer added sheets. Preferred are compositions and methods for cleaning and/or treating textiles and/or hard surfaces, most preferably textiles. The compositions are preferably compositions used in a pretreatment step or main wash step of a washing process, most preferably for use in textile washing step.

As used herein, the term "fabric and/or hard surface cleaning and/or treatment composition" is a subset of cleaning and treatment compositions that includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, car or carpet shampoos, bathroom cleaners including toilet bowl cleaners; fabric conditioning compositions including softening and/or freshening that may be in liquid, solid and/or dryer sheet form; as well as cleaning auxiliaries such as bleach additives and "stain-stick" or pre-treat types, substrate-laden compositions such as dryer added sheets. All of such compositions which are applicable may be in standard, concentrated or even highly concentrated form even to the extent that such compositions may in certain aspect be non-aqueous.

Method of Use

The present invention includes a method for cleaning any surface including treating a textile or a hard surface or other surfaces in the field of fabric and/or home care. In one aspect of the invention, the method comprises the step of contacting the surface to be treated in a pre-treatment step or main wash step of a washing process, most preferably for use in a textile washing step or alternatively for use in dishwashing including both manual as well as automated/mechanical dishwashing. In one embodiment of the invention the lipase variant and other components are added sequentially into the method for cleaning and/or treating the surface. Alternatively, the lipase variant and other components are added simultaneously.

As used herein, washing includes but is not limited to, scrubbing, and mechanical agitation. Washing may be conducted with a foam composition as described in WO08/101958 and/or by applying alternating pressure (pressure/vaccum) as an addition or as an alternative to scrubbing and mechanical agitation. Drying of such surfaces or fabrics may be accomplished by any one of the common means employed either in domestic or industrial settings. The cleaning compositions of the present invention are ideally suited for use in laundry as well as dishwashing applications. Accordingly, the present invention includes a method for cleaning an object including but not limiting to fabric, tableware, cutlery and kitchenware. The method comprises the steps of contacting the object to be cleaned with a said cleaning composition comprising at least one embodiment of Applicants' cleaning composition, cleaning additive or mixture thereof. The fabric may comprise most any fabric capable of being laundered in normal consumer or institutional use conditions. The solution may have a pH from 8 to 10.5. The compositions may be employed at concentrations from 500 to 15.000 ppm in solution. The water temperatures typically range from 5° C. to 90° C. The water to fabric ratio is typically from 1:1 to 30:1.

In one aspect the invention relates to a method of using the polypeptide with at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to SEQ ID NO: 2 for producing a composition. In one aspect the invention relates to use of the composition for cleaning an object.

In one aspect the invention relates to a method of producing the composition, comprising adding a polypeptide with at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identity to SEQ ID NO: 2, and a surfactant. In one aspect the invention relates to a method for cleaning a surface, comprising contacting a lipid stain present on the surface to be cleaned with the cleaning composition. In one aspect the invention relates to a method for hydrolyzing a lipid present in a soil and/or a stain on a surface, comprising contacting the soil and/or the stain with the cleaning composition.

Plants

The present invention also relates to plants, e.g., a transgenic plant, plant part, or plant cell, comprising a polynucleotide of the present invention so as to express and produce the polypeptide in recoverable quantities. The polypeptide may be recovered from the plant or plant part. Alternatively, the plant or plant part containing the polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca*, *Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing a polypeptide may be constructed in accordance with methods known in the art. In short, the plant or plant cell is constructed by incorporating one or more expression constructs encoding a polypeptide into the plant host genome or chloroplast genome and propagating the resulting modified plant or plant cell into a transgenic plant or plant cell.

The present invention also relates to methods of producing a polypeptide of the present invention comprising: (a) cultivating a transgenic plant or a plant cell comprising a polynucleotide encoding the polypeptide under conditions conducive for production of the polypeptide; and (b) recovering the polypeptide.

Preferred Embodiments of the Invention

Preferred embodiments of the invention are described in the set of items below.

1. An isolated polypeptide with lipase activity, selected from the group consisting of:
   (a) a polypeptide having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2;
   (b) a polypeptide encoded by a polynucleotide that hybridizes under high stringency conditions with (i) nucleic acids 70 to 927 of SEQ ID NO: 1 or the full-length complement of (i);
   (c) a polypeptide encoded by a polynucleotide having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature lipase polypeptide coding sequence of SEQ ID NO: 1;
(d) a polypeptide which is a variant of SEQ ID NO: 2 comprising a substitution and/or deletion and/or insertion, wherein the variant has lipase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41 or 42 positions; and
(e) a polypeptide which is a fragment of any of the polypeptides of (a), (b), (c) or (d), wherein the fragment has lipase activity and comprises at least 200 amino acids.

2. The polypeptide according to item 1, wherein the fragment has lipase activity and comprises at least 225 amino acids, such as at least 250, at least 275 or at least 280 amino acids.

3. The polypeptide according to item 2, wherein the fragment has lipase activity and comprises 281, 282, 283, or 284 amino acids.

4. The polypeptide according to item 1, wherein the variant comprises a substitution, preferably a conservative substitution, in 1, 2, 3, 4, 5, 6, 7, 8, 9 or 10 positions.

5. The polypeptide according to any of items 1 to 4, wherein the polypeptide has at least 25%, at least 30%, at least 35%, at least 40%, at least 45%, at least 50%, at least 55%, at least 60%, at least 65%, at least 70%, at least 80%, at least 85%, at least 90%, at least 95%, or at least 100% of the lipase activity of the polypeptide of SEQ ID NO: 2.

6. The polypeptide according to item 1, wherein the polypeptide comprises or consists of amino acids 1 to 285 of SEQ ID NO: 2.

7. The polypeptide according to item 1, wherein the mature polypeptide coding sequence is nucleic acids 70 to 927 of SEQ ID NO: 1.

8. An isolated polypeptide having the ability to function as a chaperone to the polypeptide of any of items 1 to 7, selected from the group consisting of:
(a) a polypeptide having at least 60%, at least 65%, at least 70%, at least 75%, at least at least 80%, at least 85%, at least 86%, at least 87% at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 3;
(b) a polypeptide encoded by a polynucleotide that hybridizes under medium-high stringency conditions with (i) nucleic acids 971 to 1786 of SEQ ID NO: 1 or the full-length complement of (i);
(c) a polypeptide encoded by a polynucleotide having at least 60%, at least 65%, at least 70%, at least 75%, at least at least 80%, at least 85%, at least 86%, at least 87%, at least 89%, at least 90%, at least 91%, at least 92%, at least 93%, at least 94%, at least 95%, at least 96%, at least 97%, at least 98%, at least 99%, or 100% sequence identity to the mature chaperone polypeptide coding sequence of SEQ ID NO: 1;
(d) a polypeptide which is a variant of SEQ ID NO: 3 comprising a substitution and/or deletion and/or insertion, wherein the variant comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions; and
(e) a polypeptide which is a fragment of any of the polypeptides of (a), (b), (c) or (d) and has at least 90% of the length of the mature polypeptide.

9. The polypeptide according to item 8, wherein the variant comprises a substitution, preferably a conservative substitution, in 1, 2, 3, 4, 5, 6, 7, 8, 9 or 10 positions.

10. The polypeptide according to item 8, wherein the polypeptide comprises or consists of amino acids 1 to 271 of SEQ ID NO: 3.

11. The polypeptide according to item 8, wherein the mature polypeptide coding sequence is nucleic acids 971 to 1786 of SEQ ID NO: 1.

12. A composition comprising a polypeptide with lipase activity, wherein the polypeptide having lipase activity is slected from the group consisting of:
a) the polypeptide according to any of items 1 to 7; and
b) a polypeptide having at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2.

13. A composition comprising a polypeptide with lipase activity, wherein the polypeptide having lipase activity has at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 20.

14. The composition of item 12 further comprising the polypeptide according to any of items 8 to 11.

15. The composition of item 13 further comprising the polypeptide according to any of items 8 to 11.

16. The composition of item 12 further comprising a polypeptide having the ability to function as a chaperone, wherein the polypeptide having the ability to function as a chaperone has at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 21.

17. The composition of item 13 further comprising a polypeptide having the ability to function as a chaperone, wherein the polypeptide having the ability to function as a chaperone has at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 21.

18. The composition of any of items 12 to 17 further comprising at least one surfactant, at least one surfactant system, at least one soap, or any mixtures thereof.

19. The composition of item 18, wherein the surfactant or surfactant systems are selected from anionic surfactants, cationic surfactants, non-ionic surfactants, ampholytic surfactants, zwitterionic surfactants, semipolar nonionic surfactants or any mixtures thereof.

20. The composition of any of items 12 to 19, wherein the composition further comprises one or more additional enzymes selected from the group consisting of protease, lipase, cutinase, amylase, alpha-amylase, carbohydrase, cellulase, pectinase, mannanase, arabinase, galactanase, xylanase, oxidase, laccase, and peroxidase.

21. The composition of any of items 12 to 20, wherein the composition is a laundry cleaning composition, a dishwashing cleaning composition, a hard-surface cleaning composition and/or a personal care cleaning composition.
22. The composition of any of items 12 to 21, wherein the composition is formulated as a regular, compact or concentrated liquid; a gel; a paste; a soap bar; a regular or a compacted powder; a granulated solid; a homogenous or a multilayer tablet with two or more layers (same or different phases); a pouch having one or more compartments; a single or a multi-compartment unit dose form; or any combination thereof.
23. A detergent composition comprising the polypeptide of any of items 1 to 7 or the composition of any of items 12 to 22 and at least one chelating agent; at least one sulfonated polymer; at least one hydrotrope; at least one builder and/or co-builder; at least one perfume; and/or at least one kind of bleaching system.
24. The detergent composition of item 23 wherein said detergent composition is a liquid laundry detergent composition, a powder laundry detergent composition, a liquid dishwash detergent composition, or a powder dishwash detergent composition.
25. Use of the detergent composition according to items 23 to 24 in laundry, manual dishwash or automatic dishwash.
26. Use according to item 25, wherein said use is in laundry or automatic dishwash at low temperature, such as less than 60° C., such as less than 55° C., such as less than 50°, such as less than 45° C., such as less than 40° C., such as less than 35° C., such as less than 30° C., such as less than 25° C., such as less than 20° C., such as less than 15° C.
27. A method of laundering, comprising laundering a fabric with a detergent composition according to any of items 23 to 24, preferably at a temperature of 40° C. or less, or more preferably at a temperature of 30° C. or less, or even more preferably at a temperature of 20° C. or less.
28. A method of dishwashing in an automatic dishwashing machine using the detergent composition of any of items 23 to 24, comprising the steps of adding said detergent composition in a detergent composition compartment in said automatic dishwashing machine, and releasing said detergent composition during a main-wash cycle.
29. A method for hydrolyzing a lipid, comprising contacting the lipid with the polypeptide of any of items 1 to 7, the composition of any of items 12 to 22 or the detergent composition of any of items 23 to 24.
30. A method for cleaning an object, comprising contacting a lipid stain present on the object to be cleaned with the polypeptide according to any of items 1 to 7, the composition of any of items 12 to 22 or the detergent composition of any of items 23 to 24.
31. A method for cleaning a subject, comprising contacting a lipid stain present on the subject to be cleaned with the polypeptide according to any of items 1 to 7, the composition of any of items 12 to 22 or the detergent composition of any of items 23 to 24.
32. An isolated polynucleotide encoding the polypeptide according to any of items 1 to 7 or the polypeptide according to any of items 8 to 10.
33. The polynucleotide of item 32, wherein the polynucleotide is modified to correspond to the codon usage of a host cell intended for recombinant production of the polypeptide.
34. A nucleic acid construct or expression vector comprising the polynucleotide of item 16 operably linked to one or more control sequences that direct the production of the polypeptide in an expression host.
35. A nucleic acid construct comprising the polynucleotide according to any of items 32 or 33.
36. An expression vector comprising the polynucleotide encoding the polypeptide according to any of items 1 to 7 and/or the polypeptide according to any of items 8 to 11.
37. A host cell comprising the polynucleotide encoding the polypeptide according to any of items 1 to 7 and/or the polypeptide according to any of items 8 to 11.
38. A method of producing a polypeptide according to any of items 1 to 7 and/or the polypeptide according to any of items 8 to 11, comprising: (a) cultivating the host cell of item 37 under conditions suitable for expression of the polypeptide; and (b) recovering the polypeptide.
39. A recombinant host cell comprising the polynucleotide of any of items 32 to 33 operably linked to one or more control sequences that direct the production of the polypeptide.
40. A method of producing a polypeptide of any of items 1 to 10, comprising:
    (a) cultivating the recombinant host cell of item 39 under conditions conducive for production of the polypeptide; and
    (b) recovering the polypeptide.

The present invention is further described by the following examples that should not be construed as limiting the scope of the invention.

EXAMPLES

Media and Solutions

Unless otherwise indicated chemicals used as buffers and substrates were commercial products of at least reagent grade. The commercially available enzymes Lipolase™ and Lipex™ were obtained from Novozymes NS.

Lipolase™ comprises the wildtype triacylglycerol lipase from *Thermomyces lanuginosus* expressed in *Aspergillus oryzae*.

Lipex™ comprises a triacylglycerol lipase derived from the wildtype *Thermomyces lanuginosus* triacylglycerol lipase having the mutations T231R and N233R and expressed in *Aspergillus oryzae*.

Lipase Assay: Hydrolytic Activity on Fatty Acids pNP Esters

The hydrolytic activity on various fatty acids may be determined in a kinetic assay using p-nitrophenyl acyl esters as substrate. The 100 mM stock solutions in DMSO of the substrates: p-Nitrophenyl butyrate (C3), p-Nitrophenyl caproate (C6), p-Nitrophenyl caprate (C10), p-Nitrophenyl laurate (C12) and p-Nitrophenyl palmitate (C16) (all from Sigma-Aldrich; Cat. no.: C3:N-9876, C6: N-0502, C10: N-0252, C12: N-2002, C16: N-2752) are diluted to a final concentration of 1 mM into the assay buffer. For pH 5 50 mM Acetate, 0.4% TritonX-100 is use; for pH 7 50 mM HEPES, 0.4% TritonX-100 and for pH 9 50 mM Tris, 0.4% TritonX-100.

Samples for assaying and appropriate controls (Buffer (negative), Lipex™ (positive)) are added in the buffer corresponding to the assayed pH with 10 ppm TritonX-100 present to the substrate solution in the following final concentrations: 0.01 mg/ml; $5 \times 10^{-3}$ mg/ml; $2.5 \times 10^{-4}$ mg/ml; and $1.25 \times 10^{-4}$ mg/ml in 96-well NUNC plates (Cat. No:260836). To evaluate the influence of $Ca^{+2}$ mM $CaCl_2$ (final concentration) are added to half of the samples.

Release of p-nitrophenol by hydrolysis of p-nitrophenyl acyl is monitored at 320 nm for pH 5 and 405 nm for pH 7 and 9 for 5 minutes in 10 second intervals on a Spectra max 190 (Molecular Devices GmbH).

Example 1: Identification of the Lipase and its Chaperone

A polycistronic operon (SEQ ID NO: 1) encoding the lipase of the invention and its intrinsic chaperone was identified in the *Gallaecimonas pentaromativorans* type strain (DSM 21945). The two open reading frames were separated by a single cytosine.

Example 2: Cloning and Expression of a Lipase from *Gallaecimonas pentaromativorans*

The *G. pentaromativorans* lipase was expressed from a synthetic gene in *E. coli*. The synthetic gene was designed based on SEQ ID NO: 1 and codon optimized for expression in E. coll. The expressed DNA sequence was SEQ ID NO: 4 encoding the mature part of the full-length protein (SEQ ID NO: 2).

Expression Vector

Any expression vector designed for *E. coli* will be suitable for expression of the *G. pentaromativorans* lipase in an *E. coli* expression strain. In this instance, pIVT2 (FIG. 1) was used as expression vector. Expression of the gene was driven by a T7 promoter (Methods in Enzymology, volume 185, pages 60-89). The pIVT2 vector contains two ribosome recognition sites, a Shine-Dalgarno site, a T7 terminator, an ampicillin resistance gene (AmpR) to make selection for transformants in *E. coli* possible, and an *E. coli* origin of replication (Col E1 origin).

Expression Cloning

The nucleotide sequence corresponding to the mature part of the encoded lipase was obtained (SEQ ID NO: 4). The insert corresponding to the mature part of the encoded lipase was PCR amplified using the below primers (F-lipase and R-lipase) and standard molecular methods F-lipase:
(SEQ ID NO: 10)
5'-AAGGAGATAAACATATGTCAGGTTATACCCAGACCAAATATCCGA
T-3'

R-lipase:
(SEQ ID NO: 11)
5'-GGTTAGTTAGAAGCTTACAGACCCAGATTTTTCAGACGATTTGC
C-3'

A NdeI restriction site was incorporated in the forward primer (F-lipase) and a HindIII restriction site in the reverse primer (R-lipase) to facilitate use of the IN-FUSION™ Cloning Kit (BD Biosciences, Palo Alto, Calif., USA) to clone the fragment directly into the expression vector pIVT2. The expression vector, pIVT2 was digested with the same restriction enzymes (NdeI and HindIII). The cloning protocol was performed according to the IN-FUSION™ Cloning Kit instructions. The treated plasmid and insert were transformed into One Shot® TOP10F' Chemically Competent *E. coli* cells (Invitrogen, Carlsbad, Calif., USA) according to the manufacturer's protocol. Integration of the insert into the vector and nucleotide sequence of the insert was verified by sequencing of isolated plasmids using commercial available vector primers (M13_Fw(-20) and M13_Rv(-27)). A representative plasmid expression clone free of PCR errors was transformed into BL21(DE3) competent cells (New England Biolabs) according to the manufacturer's protocol.

*E. coli* Intracellular Expression

A recombinant *E. coli* BL21(DE3) clone containing the episomal plasmid expression clone were grown in liquid culture. Lipase expression was done according to the protocol supplied by the manufacturer (Protein Expression Using BL21(DE3) (C2527)). In short, inoculate 1 L of liquid medium (with ampicillin) with 10 ml of freshly grown culture. Incubate at 37° C. 250 rpm until $OD_{600}$ reaches 0.4-0.8. Add Isopropyl␣␣-D-1-thiogalactopyranoside (IPTG) to a final concentration of 400 µM and continue fermentation for 4 hours at 30° C., 250 rpm. Pellet cells by centrifugation and resuspend the obtained cell pellet in 50 mM Tris buffer, pH 7.5. Release of the intracellular expressed lipase was facilitated by cell lysis using a Cell Disrupter (TS series Bench Top model, Constant Systems, UK) at 17,500 PSI. The total lysate was fractioned into a soluble and insoluble sample by centrifugation, and total protein expression was evaluated by SDS-page. The lipase was found in the insoluble sample as inclusion bodies. The insoluble sample was washed twice in 50 mM Tris, pH 7.5 and the enzyme (SEQ ID NO: 2) was purified as described in example 5.

Example 3: Cloning and Expression of a Chaperone from *Gallaecimonas pentaromativorans*

The *G. pentaromativorans* chaperone was expressed from a synthetic gene in E. coll. The synthetic gene was designed based on SEQ ID NO: 1 (*G. pentaromativorans* polycistronic operon) and codon optimized for expression in E. coll. The DNA sequence used for expression was SEQ ID NO: 5. The amino acid sequence of the mature part of the *G. pentaromativorans* chaperone is shown in SEQ ID NO: 3.

The gene encoding the *Escherichia coli* maltose binding protein was derived from the *E. coli* strain K12. The nucleotide sequence is shown in SEQ ID NO: 6. The corresponding amino acid sequence is shown in SEQ ID NO: 7.

Expression Vector

Any expression vector designed for *E. coli* will be able to support expression of the *G. pentaromativorans* in an *E. coli* expression strain. Examples of such are the commercial available pET-based expression systems and the *E. coli* expression strains BL21 or BL21(DE3) (Life Technologies) or XJ Autolysis (Zymoresearch).

In this instance, pIVT3 (FIG. 2) was used as expression vector. Expression of the gene was driven by a T7 promoter. The pIVT3 vector contains two ribosome recognition sites, a Shine-Dalgarno site, a T7 terminator, a kanamycin resistance gene (KanR) to make selection for transformants in *E. coli* possible, and an *E. coli* origin of replication (Col E1 origin). A 6 histidine tag is positioned in frame 5' to an AvrII restriction site.

Expression Cloning

The gene encoding the mature part of the *G. pentaromativorans* chaperone was fused to the 3'end of the gene encoding the *E. coli* maltose binding protein. A 42 basepair long linker sequence AATTCGAGCTC-GAACAACAACAACAATAACAATAACAACAAC (SEQ ID NO: 12) was interspaced between the genes encoding the chaperone and maltose binding protein. A 6× histidine tag, encoded on the expression vector pIVT3, was fused in frame to the 5' end of the mature nucleotide sequence of *E. coli* maltose binding protein. The complete nucleotide sequence of the fusion protein is shown in SEQ ID NO: 8. The amino acid sequence of the fusion protein is shown in SEQ ID NO: 9.

A synthetic gene encoding the mature part of the *G. pentaromativorans* chaperone was obtained (SEQ ID NO: 5). The insert corresponding to the mature part of the encoded chaperone was PCR amplified using the below primers (F-Chaperone and R-Chaperone) and standard molecular methods. A HindIII restriction site was incorporated in the reverse primer (R-Chaperone) to facilitate use of the IN-FUSION™ Cloning Kit (BD Biosciences, Palo Alto, Calif., USA) to clone the fragment directly into the expression vector pIVT3. The linker sequence for fusing the *G. pentaromativorans* chaperone to the *E. coli* maltose binding protein was included in the forward primer (F-Chaperone).

F-Chaperone:
(SEQ ID NO: 13)
5'-5'-AATTCGAGCTCGAACAACAACAACAATAACAATAACAACAACGG
TCTGCTGTATCTGGTTTTTCCGG-3'

R-Chaperone:
(SEQ ID NO: 14)
5'-TGGTTAGTTAGAAGCTTACTGCATACCATTGCTCAGCCACA-3'

The nucleotide sequence corresponding to the mature part of the encoded *E. coli* maltose binding protein (MBP) was PCR amplified from *E. coli* K12 genomic DNA using the below primers and standard molecular methods. An AvrII restriction site was incorporated in the forward primer (F-MBP) to facilitate use of the IN-FUSION™ Cloning Kit (BD Biosciences) to clone the fragment directly into the expression vector pIVT3. The linker sequence for fusing the *G. pentaromativorans* chaperone to the *E. coli* maltose binding protein was included in the reverse primer (R-MBP).

F-MBP:
(SEQ ID NO: 15)
5'-ccatcaccaccctaggAAAATCGAAGAAGGTAAACTGGTAATCTGG
A-3'

R-MBP:
(SEQ ID NO: 16)
5'-GTTGTTGTTATTGTTATTGTTGTTGTTGTTCGAGCTCGAATTAGTCT
GCGCGTCTTTCAGGGCTTCATCGACAGTCTGACGACCGCTGGC-3'

The two PCR products were spliced into a single amplicon by overlap extension PCR using the flanking primers previously used for PCR amplification of the individual PCR products (F-MBP and R-Chaperone). The expression vector, pIVT3 was digested with the same restriction enzymes (AvrII and HindIII). The cloning protocol was performed according to the IN-FUSION™ Cloning Kit instructions. The treated plasmid and amplicon were transformed into One Shot® TOP10F' Chemically Competent *E. coli* cells (Invitrogen, Carlsbad, Calif., USA) according to the manufacturer's protocol. Integration of the insert into the vector and nucleotide sequence of the insert was verified by sequencing of isolated plasmids using commercial available vector primers (M13_Fw(−20) and M13_Rv(−27)) (Life Technologies) and the below sequencing primers (Seq1, Seq2 and Seq3).

Seq1:
(SEQ ID NO: 17)
5'-CAAGCTGATTGCTTACCCGATC-3'

Seq2:
(SEQ ID NO: 18)
5'-AAGAGTTCCTCGAAAACTATCTGCTG-3'

Seq3:
(SEQ ID NO: 19)
5'-GCAGATATTAATGCAGCACTGGC-3'

A representative plasmid expression clone free of PCR errors was transformed into BL21(DE3) competent cells (New England Biolabs) according to the manufacturer's protocol.

Example 4: Fermentation of the Recombinant *E. coli*

A recombinant *E. cog* BL21(DE3) clone containing the episomal plasmid expression clone were grown in liquid culture by inoculating 1 L of liquid medium (with kanamycin) with 10 ml of freshly grown culture. Incubating at 37° C. 250 rpm until $OD_{600}$ reaches 0.4-0.8. Add Isopropyl p-D-1-thiogalactopyranoside (IPTG) to a final concentration of 400 μM and continuing fermentation for 4 hours at 30° C., 250 rpm. Pelleting cells by centrifugation and resuspending the obtained cell pellet in 50 mM Tris buffer, pH 7.5. The intracellular expressed chaperone was released by cell lysis using a Cell Disrupter (TS series Bench Top model, Constant Systems, UK) at 17,500 PSI. The total lysate was fractioned into a soluble and insoluble sample by centrifugation, and total protein expression was evaluated by SDS-page. The chaperone was found in the both in the soluble sample and as inclusion bodies. The soluble sample was used for further work and the fusion protein (SEQ ID NO: 9) was purified as described in example 5.

Example 5: Purification and Refolding

The cells expressing the chaperone fusion protein were harvested by centrifugation and the resuspended in 50 mL (per liter cell culture) of 50 mM Tris pH 7.5. The cells were subsequently disrupted in a cell disrupter (Constant Systems LTD) at 17,500 psi. The lysate was spun at 10,000 g for 10 min at 4° C. to remove cell debris and filtered with a 0.2 μm Nalgene™ Rapid-Flow™ Sterile Disposable Filter.

The sterile supernatant was applied to a 15 ml His-Trap excel column (GE healthcare), equilibrated with 50 mM HEPES pH 8. After washing the column with 5 column volumes (CV) the chaperone fusion protein was eluted with 50 mM HEPES pH 8, 0.8 M Imidazole. Fractions with high A280 absorbance were pooled.

The lipase protein harvested as inclusion bodies was solubilized in 50 mM HEPES pH 7.5+8 M Urea+73 mM Dithioerythritol (10 ml buffer/inclusion bodies from 1l culture). Refolding was done on a Superdex 200 column. The column was equilibrated in 2 CV 50 mM HEPES pH 7.5, 300 mM NaCl, 0.75 M Arginine and then loaded with ⅓ CV of 50 mM HEPES pH 7.5, 300 mM NaCl, 0.75 M Arginine, 1 mM L-Glutathione and purified LIF.

10 ml of re-solubilised lipase protein was injected onto the column and refolded with the chaperone. Fractions were collected and checked for activity on olive oil plates (1.25% Olive oil, 0.008% Brilliant green, 1% agarose, 0.07% polyvinyl alcohol, 50 mM HEPES pH 7.2). 20 μl aliquots of the various fractions, buffer (negative control) and Lipolase™ and Lipex™ (positive controls) were each distributed into punched holes with a diameter of 3 mm and incubated for 4-6 hours at room temperature. Activity was visualized by appearance of a blue ring around the punched hole, indicating a pH drop due to the presence of free fatty acids originating from the hydrolisation of olive oil triglycerides.

Example 6: Enzyme Characterization

Substrate Specificity:

When tested using the 'lipase assay: hydrolytic activity on fatty acids pNP esters' as disclosed herein, the lipase of the invention had highest activity towards shorter chained acyl-ester, with an activity maximum for pNP-carproate (C6) as substrate at the three tested pH values 5, 7 and 9 (see table 2 below). The activity decreased with shorter and longer fatty acid chains of pNP acyl esters and no activity was measured for pNP-palmitate (C16) at any of the tested pH values.

TABLE 2

Activity of the lipase of the invention towards different fatty acid chain lengths using pNP acyl esters.

| | | Linear rate (abs/min) | |
|---|---|---|---|
| | Nr. of carbons in pNP-esters | Lipase + Chap-MBP | Neg. Control |
| pH 5 | C3 | 0.117 | 0.001 |
| | C6 | 0.300 | 0.006 |
| | C10 | 0.082 | 0.006 |
| | C12 | 0.044 | −0.001 |
| | C16 | 0.003 | −0.008 |
| pH 7 | C3 | 0.139 | 0.000 |
| | C6 | 0.218 | 0.003 |
| | C10 | 0.059 | −0.015 |
| | C12 | 0.005 | −0.004 |
| | C16 | −0.004 | −0.002 |
| pH 9 | C3 | 0.305 | 0.015 |
| | C6 | 0.535 | 0.001 |
| | C10 | 0.135 | −0.011 |
| | C12 | 0.018 | 0.020 |
| | C16 | −0.002 | −0.002 |

$Ca^{++}$ Dependency

When tested using the 'lipase assay: hydrolytic activity on fatty acids pNP esters' as disclosed herein, the activity was Ca' dependent and the activity decreased significantly when no calcium was present.

TABLE 3

Comparison of lipase activity on pNP-caproate (C6) at pH 7 with or without added 2 mM $CaCl_2$ and an enzyme concentration of 0.01 mg/mL

| | Linear rate (abs/min) | |
|---|---|---|
| | Lipase + Chap-MBP | Neg. Control |
| + $CaCl_2$ | 0.260 | 0.005 |
| − $CaCl_2$ | 0.008 | −0.001 |

Example 7: Determination of Td by Differential Scanning Calorimetry

The thermostability of the lipase of the invention was determined by Differential Scanning calorimetry (DSC) using a VP-Capillary Differential Scanning calorimeter (MicroCal Inc., Piscataway, N.J., USA). The thermal denaturation temperature, Td (° C.), was taken as the top of denaturation peak (major endothermic peak) in thermograms (Cp vs. T) obtained after heating enzyme solutions (approx. 0.5 mg/ml) in buffer (50 mM Hepes, pH 8.0) at a constant programmed heating rate of 200 K/hr.

Sample- and reference-solutions (approx. 0.2 ml) were loaded into the calorimeter (reference: buffer without enzyme) from storage conditions at 10° C. and thermally pre-equilibrated for 20 minutes at 20° C. prior to DSC scan from 20° C. to 100° C. Denaturation temperatures were determined at an accuracy of approximately +/−1° C.

In complex with the chaperone fusion protein, the thermostability of the lipase was high with a Td value in the range of 79.9-94.1° C. In a non-parallel trial under similar experimental conditions the thermostability of Lipolase was measured to have a Td value of 77.0° C.

Example 8: Relative Wash Performance

Washing experiments were performed, using the Automatic Mechanical Stress Assay (AMSA) in order to assess the wash performance in laundry in detergent with various concentrations of surfactant at pH 8, 9 and 10.

The AMSA plate has a number of slots for test solutions and a lid firmly squeezing the laundry sample, the textile to be washed against all the slot openings. During the washing time, the plate, test solutions, textile and lid were vigorously shaken to bring the test solution in contact with the textile and apply mechanical stress in a regular, periodic oscillating manner. For further description see WO02/42740 especially the paragraph "Special method embodiments" at page 23-24.

The laundry experiments were conducted in glycine buffers at different pH and in Model Detergents with different surfactant level and with different pH. The experimental conditions are specified below:

TABLE 4

| Detergent buffers | |
|---|---|
| Detergents/buffers | 50 mM glycine buffer pH 8 |
| | 50 mM glycine buffer pH 9 |
| | 50 mM glycine buffer pH 10 |
| | 3.3 g/L Detergent 0% surfactant, 50 mM glycine buffer pH 8 |
| | 3.3 g/L Detergent 0% surfactant, 50 mM glycine buffer pH 9 |
| | 3.3 g/L Detergent 0% surfactant, 50 mM glycine buffer pH 10 |
| | 3.3 g/L Detergent 10% surfactant, 50 mM glycine buffer pH 8 |
| | 3.3 g/L Detergent 10% surfactant, 50 mM glycine buffer pH 9 |
| | 3.3 g/L Detergent 10% surfactant, 50 mM glycine buffer pH 10 |

TABLE 4-continued

Detergent buffers

|  |  |
|---|---|
|  | 3.3 g/L Detergent 20% surfactant, 50 mM glycine buffer pH 8 |
|  | 3.3 g/L Detergent 20% surfactant, 50 mM glycine buffer pH 9 |
|  | 3.3 g/L Detergent 20% surfactant, 50 mM glycine buffer pH 10 |
|  | 3.3 g/L Detergent 60% surfactant, 50 mM glycine buffer pH 8 |
|  | 3.3 g/L Detergent 60% surfactant, 50 mM glycine buffer pH 9 |
|  | 3.3 g/L Detergent 60% surfactant, 50 mM glycine buffer pH 10 |
|  | 3.3 g/L Detergent 100% surfactant, 50 mM glycine buffer pH 8 |
| Test solution volume | 160 microliter |
| Wash time | 15 minutes |
| Temperature | 25° C. |
| Water hardness | 15°dH |
| Lipase dosage | 0 ppm & 0.3 ppm |
| Test material | Cream turmeric stain according to WO-2006/125437 |

TABLE 5

Detergent composition (wt %)

| | | | | | |
|---|---|---|---|---|---|
| Total surfactant level compared to estimated average level of surfactants in a typical high-tier commercial EU detergent (defined as 100% surfactant level) | 10% | 10% | 20% | 60% | 100% |
| linear alkylbenzenesulfonic acid (LAS) (Marlon AS3) | 0 | 1.3 | 2.6 | 7.8 | 13 |
| sodium alkyl(C12)ether sulfate (AEOS) (STEOL CS-370 E) | 0 | 1 | 2 | 6 | 10 |
| alcohol ethoxylate (AEO) (Bio-Soft N25-7) | 0 | 1.1 | 2.2 | 6.6 | 11 |
| coco soap (Radiacid 631) | 2.75 | 2.75 | 2.75 | 2.75 | 2.75 |
| soy soap (Edenor SJ) | 2.75 | 2.75 | 2.75 | 2.75 | 2.75 |
| sodium hydroxide | 0 | 0.2 | 0.4 | 1.2 | 2 |
| ethanol | 3 | 3 | 3 | 3 | 3 |
| propane-1,2-diol (MPG) | 6 | 6 | 6 | 6 | 6 |
| glycerol | 2 | 2 | 2 | 2 | 2 |
| triethanolamine (TEA) | 3 | 3 | 3 | 3 | 3 |
| sodium formate | 1 | 1 | 1 | 1 | 1 |
| sodium citrate | 2 | 2 | 2 | 2 | 2 |
| Diethylenetriamine-pentakis(methylenephosphonic acid) (DTMPA) | 0.2 | 0.2 | 0.2 | 0.2 | 0.2 |
| polycarboxylate polymer (PCA) (Sokalan CP-5) | 0.2 | 0.2 | 0.2 | 0.2 | 0.2 |
| Water up to | 100 | 100 | 100 | 100 | 100 |

Final adjustments to the specified pH were done with NaOH or citric acid. Water hardness was adjusted to 15° ° dH by addition of CaCl$_2$ and MgCl$_2$ (Ca$^{2+}$:Mg$^{2+}$=4:1). After washing the textiles were flushed in tap water and excess water was removed from the textiles using filter paper and immediately thereafter the textiles were dried at 85° C. for 5 min.

The wash performance was measured as the color change of the washed soiled textile. The soil was cream mixed with turmeric. Turmeric contains the colorant curcumin, which function as a pH indicator by having pH dependent color change. Lipase activity leads to release of free fatty acids from the cream acylglycerides and this leads to pH decrease and thereby color change of the curcumin pH indicator. Lipase wash performance can therefore be expressed as the extent of color change of light reflected from the washed soiled textile when illuminated with white light.

Color measurements were made with a professional flat-bed scanner (Kodak iQsmart, Kodak, Midtager 29, DK-2605 Brondby, Denmark), which was used to capture an image of the washed soiled textile. To extract a value for the light intensity from the scanned images, 24-bit pixel values from the image were converted into values for red, green and blue (RGB). The intensity value (Int) was calculated by adding the RGB values together as vectors and then taking the length of the resulting vector:

$$Int = \sqrt{r^2 + g^2 + b^2}$$

Color change due to lipase activity was measured as the increase in the reflection of green light (G) relative to the intensity (Int) of the total reflected light. The wash performance (RP(Wash)) of a lipase relative to a reference lipase (Lipolase™) was calculated as: RP(Wash)=(G/(B+R)(tested lipase)−G/(B+R)(no enzyme))/(G/(B+R)(lipase ref.)−G/(B+R)(no enzyme)) and the results are presented in table 6 below.

TABLE 6

Relative wash performance of the lipase of the invention

| | pH | Lipolase RP (wash) | Lipase of the invention RP (wash) |
|---|---|---|---|
| Buffer 0% surfactant | 8 | 1.00 | 1.04 |
|  | 9 | 1.00 | 0.49 |
|  | 10 | 1.00 | 2.16 |
| Detergent 0% surfactant | 8 | 1.00 | 0.89 |
|  | 9 | 1.00 | 0.78 |
|  | 10 | 1.00 | 2.46 |
| Detergent 10% surfactant | 8 | 1.00 | 1.40 |
|  | 9 | 1.00 | 6.59 |
|  | 10 | 1.00 | 14.70 |
| Detergent 20% surfactant | 8 | 1.00 | 2.00 |
|  | 9 | 1.00 | 6.01 |
|  | 10 | 1.00 | 16.59 |
| Detergent 60% surfactant | 8 | 1.00 | 2.75 |
|  | 9 | 1.00 | 3.73 |
|  | 10 | 1.00 | 6.91 |
| Detergent 100% surfactant | 8 | 1.00 | 2.37 |

The results demonstrate that the lipase of the invention has an improved wash performance compared to the reference lipase Lipolase in all case where a surfactant is present. The improved performance is especially large at pH 9 and 10.

Example 8: Activity on Lipid Coated Cellulose

Performance i.e. hydrolytic activity was determined by measuring the release of 4-methylumbelliferone (4-MU) by purified protein samples of the lipase of the invention and reference lipase Lipex at increasing surfactant levels in a model detergent.

Cellulose (Avicel) was coated with a mixture of triglyceride and 4-methylumbelliferyl oleate (4-MU oleate) in an initial substrate preparation step. In the assay, the coated cellulose fibers were suspended in a buffer, a detergent solution, and a lipase solution. The lipase activity was monitored in the cellulose suspension by measuring the fluorescence at Ex: 365 nm and Em: 445 nm as a function of time.

TABLE 7

| Model detergent composition (wt %) | | | |
|---|---|---|---|
| Total surfactant level compared to estimated average level of surfactants in a typical high-tier commercial EU detergent (defined as 100% surfactant level) | 20% | 60% | 100% |
| linear alkylbenzenesulfonic acid (LAS) (Marlon AS3) | 2.6 | 7.8 | 13 |
| sodium alkyl(C12)ether sulfate (AEOS) (STEOL CS-370 E) | 2 | 6 | 10 |
| alcohol ethoxylate (AEO) (Bio-Soft N25-7) | 2.2 | 6.6 | 11 |
| coco soap (Radiacid 631) | 2.75 | 2.75 | 2.75 |
| soy soap (Edenor SJ) | 2.75 | 2.75 | 2.75 |
| sodium hydroxide | 0.4 | 1.2 | 2 |
| ethanol | 3 | 3 | 3 |
| propane-1,2-diol (MPG) | 6 | 6 | 6 |
| glycerol | 2 | 2 | 2 |
| triethanolamine (TEA) | 3 | 3 | 3 |
| sodium formate | 1 | 1 | 1 |
| sodium citrate | 2 | 2 | 2 |
| Diethylenetriaminepentakis (methylenephosphonic acid) (DTMPA) | 0.2 | 0.2 | 0.2 |
| polycarboxylate polymer (PCA) (Sokalan CP-5) | 0.2 | 0.2 | 0.2 |
| Water up to | 100 | 100 | 100 |

HEPES buffer for incubation was based on following stock solution: 1 M HEPES, 5 mM $CaCl_2$, 50 ppm Triton X-100. Adjusted to pH 8.5 with 4 M NaOH.

Coated cellulose fibers were prepared by pipetting 668 uL 4-MU-oleate stock solution (4 mg/mL 4-Methylumbelliferyl oleate in hexane) and 3.03 mL olive oil stock solution into 100 mL hexane in a round bottomed flask for rotational evaporator, and mixed properly before 10 g cellulose fibers was added. The flask was mounted on a rotational evaporator, and hexane was removed by evaporation at reduced pressure and constant mixing (by rotation) to ensure uniformly coating of the substrate on the cellulose. After complete removal of hexane, the coated cellulose fibers were transferred to a brown flask and the material was stored protected from light at 20° C. until use.

The assay was conducted by transferring 180 uL of Substrate suspension to each well in a black micro-well microtiter plate (e.g. Nunclon surface, 96 well black plates with black bottom, NUNC 137101). It is important to keep a constant, thorough mixing of the Substrate suspension when pipetting to ensure that the same amount of coated cellulose fibers are transferred to each well of the microtiter plate.

The assay was started with addition of 20 uL of incubation solution. The enzyme incubation solution should be added immediately after addition of the Detergent working solution (1.835 g Model Detergent (Table 4), 100 ml 1 M HEPES buffer, Water hardness was adjusted to 15° dH by addition of $CaCl_2$ and $MgCl_2$ ($Ca^{2+}$:$Mg^{2+}$=4:1) to the test system and finally adjusted to 500 mL with Milli Q water and pH adjusted to pH 8.5 with 4 M NaOH). For the blank, 20 uL Lipase incubation buffer was added.

The enzyme activity was followed by measuring the fluorescence (kinetic mode) every 30 seconds at Ex: 365 nm and Em: 445 nm from 1 to 6 minutes after enzyme addition. The plate was mixed by shaking for 5 seconds before first measurement but not between the following measurements. The assay was run at room temperature, i.e. approximately at 20° C.

The activity was calculated as the slope of a plot of fluorescence versus time (units: RFU/sec, where RFU is the Relative Fluorescence Signal Unit) using the 1-6 minute time window after enzyme addition and the results are presented in table 8 below.

TABLE 8

| Lipase activity determined by lipid coated cellulose assay | | |
|---|---|---|
| | Lipex (RFSU/Sec) | Lipase of the invention (RFSU/Sec) |
| Detergent 20% surfactant[1] | 19.6 | 29.2 |
| Detergent 60% surfactant[1] | 19.8 | 32.2 |
| Detergent 100% surfactant[1] | 10.7 | 46.2 |

[1]Total surfactant level compared to estimated average level of surfactants in a typical high-tier commercial EU detergent (defined as 100% surfactant level)

The results demonstrate that the lipase of the invention has a higher kinetic activity compared to the reference lipase Lipolase.

The invention claimed is:

1. A detergent composition, comprising:
a polypeptide with lipase activity, wherein the amino acid sequence of the polypeptide with lipase activity has at least 90% sequence identity to the amino acid sequence of SEQ ID NO: 2, or a fragment thereof having lipase activity;
a polypeptide having chaperone activity for the polypeptide with lipase activity, wherein the amino acid sequence of the polypeptide having chaperone activity has at least 85% sequence identity to the amino acid sequence of SEQ ID NO: 3; and
at least one surfactant,
wherein the polypeptide with lipase activity is present in the detergent composition in an amount effective to improve the wash performance in an Automatic Mechanical Stress Assay as compared to the same detergent composition without the polypeptide with lipase activity, and
wherein the at least one surfactant is present in the detergent composition at a level that improves the relative wash performance of the lipase in an Automatic Mechanical Stress Assay as compared to the same detergent composition without the surfactant.

2. The detergent composition of claim 1, wherein the surfactant is selected from anionic surfactants, cationic surfactants, non-ionic surfactants, ampholytic surfactants, zwitterionic surfactants, semipolar nonionic surfactants, or any mixtures thereof.

3. The detergent composition of claim 1, wherein the composition further comprises one or more enzymes selected from the group consisting of protease, lipase, cutinase, amylase, alpha-amylase, carbohydrase, cellulase, pectinase, mannanase, arabinase, galactanase, xylanase, oxidase, laccase, and peroxidase.

4. The detergent composition of claim 1, wherein the composition is a laundry cleaning composition, a dishwashing cleaning composition, a hard-surface cleaning composition or a personal care cleaning composition.

5. The detergent composition of claim 1, wherein the composition is formulated as a regular, compact or concentrated liquid; a gel; a paste; a soap bar; a regular or a compacted powder; a granulated solid; a homogenous or a multilayer tablet with two or more layers of the same or different phases; a pouch having one or more compartments; a single or a multi-compartment unit dose form; or any combination thereof.

6. A method for hydrolyzing a lipid, comprising contacting the lipid with the detergent composition of claim 1 to thereby hydrolyze the lipid.

7. A method for cleaning an object with a lipid stain present on the object, comprising contacting the lipid stain present on the object with the detergent composition of claim 1 to thereby clean the object.

8. A nucleic acid construct or expression vector comprising a polynucleotide encoding a polypeptide having lipase activity,
wherein the polynucleotide is operably linked to one or more heterologous control sequences that direct the production of the polypeptide having lipase activity, and
wherein the amino acid sequence of the polypeptide has at least 90% sequence identity to the amino acid sequence of SEQ ID NO: 2.

9. An isolated recombinant host cell comprising the nucleic acid construct or expression vector of claim 8.

10. A method comprising:
(a) cultivating the recombinant host cell of claim 9 under conditions conducive for production of the polypeptide having lipase activity; and
(b) recovering the polypeptide having lipase activity.

11. The detergent composition of claim 1, wherein the surfactant is present at a level of from 0.1 to 60 wt %.

12. The detergent composition of claim 1, wherein the surfactant is selected from the group consisting of sodium (linear alkyl)benzenesulfonate (LAS), sodium alkyl sulfate (AS), sodium lauryl ether sulfate (AEOS), alcohol ethoxylate (AEO) and alpha-olefinsulfonate (AOS).

13. The detergent composition of claim 1, further comprising a bleach catalyst.

14. The detergent composition of claim 1, further comprising a soap, wherein the soap is present in an amount from 0.5 wt % to 20 wt %.

15. The detergent composition of claim 1, further comprising a soap, wherein the soap is in the form of a mixture of fatty acid soaps.

* * * * *

SEQUENCE LISTING

```
<160> NUMBER OF SEQ ID NOS: 21

<210> SEQ ID NO 1
<211> LENGTH: 1786
<212> TYPE: DNA
<213> ORGANISM: Gallaecimonas pentaromativorans
<220> FEATURE:
<221> NAME/KEY: misc_feature
<222> LOCATION: (1)..(1786)
<223> OTHER INFORMATION: DNA sequence of polycistronic operon of the WT
      Gallaecimonas pentaromativorans lipase and chaperone
<220> FEATURE:
<221> NAME/KEY: misc_feature
<222> LOCATION: (1)..(69)
<223> OTHER INFORMATION: DNA sequence of lipase secretion signal 1..69
      bp
<220> FEATURE:
<221> NAME/KEY: misc_feature
<222> LOCATION: (70)..(927)
<223> OTHER INFORMATION: DNA sequence of mature lipase 70..927 bp
```

```
<220> FEATURE:
<221> NAME/KEY: misc_feature
<222> LOCATION: (929)..(970)
<223> OTHER INFORMATION: DNA sequence of chaperone secretion signal
      929..970 bp
<220> FEATURE:
<221> NAME/KEY: misc_feature
<222> LOCATION: (971)..(1786)
<223> OTHER INFORMATION: DNA sequence of mature chaperone 971.. 1786 bp

<400> SEQUENCE: 1
atgtcactca agtctctgtt tttggggctg gcgctgctgt gcgccttgcc tgtccaaccg      60
gccgctgcca gcggctatac ccaaaccaaa taccctatcg ttctggttca cggccttttt     120
gggtttgatt cactggctgg ggtcgattat tggtacggca taccgcaggc ccttagccaa     180
gacggcgcca cggtctatgt ggtgaacgtg tcggcggcca acagcaccga agtgcgggc      240 gaacagttgc tggtgcaaat cgataacatc ctggcgctta ccggcgccaa gaaggtcaac     300
ctgattggcc attccacgg cggcccact gcccgctatg cggcgtccat cagcccgggc       360
aaggtggcgt cggtcacttc ggtgggcggc gttaactggg gctcgcgctt tgccgatgcc     420
ctgcgcggta ccattgcgcc cggtagcgtg tcggaaagcg tgattggcgc cgccgccaac     480
gccttttcga gcattatcga gttcctctct ggcactccgg ccgacccgca agactcggtg     540
gcggcgctca atgccctgac caccgccggc tcgctggcct ttaacgccag ctaccccgaa     600
ggcatgccca ccaatattg cggccagggc cagatgcagg ccgccaacgg cgtttattac      660
ttctcctgga gtggcgccag cccgctcacc aatgtgctgg acgttaccga cgccgccctg     720
ggcctcacct ccctggtgtt tggcgaaagc aacgacggcc tggtgtctag ctgctcaagc     780
cacttgggta aggtgatccg tgacgactac gccatgaacc cctcgatga ggttaaccag     840 accttcggcc tggtcagcct gtttgaaacc aaccccaaga cgctttatcg caaccaggca    900
aacaggctca aaaacctggg gctttaacat gaagcccttc acgatcatgg tgccggtgtt    960
ggcggtggcc ggcctcttgt acctggtgtt tcccgagcgc caccccatgg cgccggtaaa   1020
ggctgccgcc agcctggctg acacccaggt tgatggcgcc gtgggcagcc gctaccgcat    1080
gagcgccgct ctaaaagccc gctttgacta ctggctgagc gccgtgggcg aattgccgct    1140
ctcggcgctg ccaggcaagc tgcccagtc gctgcgccag gacggctggg ccgaggcgga    1200
tatcaacgcg cgcgctggccg cctttgccca ctaccagcag tatctggacg ccttaagtga   1260
ggttgccaag cctcaggcgg ctgcggccgc cgagctaaag gcagcctggg ccgagcggga    1320
cgccctgcgc cgccagtttt acgcggaggc tgagatcaag ctgctgtggg cgacgaggc    1380 ggcggtggag gatttcaccc tgcgccgcct ggagatccag agtctcgggc tgagcgaagg   1440
cgaacagctc aaatgggagg aagacgccct ggcccaggca ccggcaacgg tgcagcaagc    1500
ctacggcccc agcctgaagt tggcgcagtt gcagcagatg aacggggcca gccgtgacca    1560
actggcagcc cagtatggcg acggcgccgc cgaccggctg atggccgcca aggcgcagca    1620
gcaggggtgg cagggcaagg tggcagccta ccgtgacaag gtaaaaagcc tggcggcgct    1680
acccagcgcc gagaaggccc aggccctggc cgaataccag gcgcgccact tctcggccaa    1740
cgagttaaag cgcttgcggg tgtggctcag taacggcatg caataa                    1786

<210> SEQ ID NO 2
<211> LENGTH: 285
<212> TYPE: PRT
<213> ORGANISM: Gallaecimonas pentaromativorans
```

<220> FEATURE:
<221> NAME/KEY: MISC_FEATURE
<222> LOCATION: (1)..(285)
<223> OTHER INFORMATION: Mature peptide sequence 1..285 of the WT
      Gallaecimonas pentaromativorans lipase

<400> SEQUENCE: 2

Ser Gly Tyr Thr Gln Thr Lys Tyr Pro Ile Val Leu Val His Gly Leu
1               5                   10                  15

Phe Gly Phe Asp Ser Leu Ala Gly Val Asp Tyr Trp Tyr Gly Ile Pro
            20                  25                  30

Gln Ala Leu Ser Gln Asp Gly Ala Thr Val Tyr Val Asn Val Ser
        35                  40                  45

Ala Ala Asn Ser Thr Glu Val Arg Gly Glu Gln Leu Leu Val Gln Ile
    50                  55                  60

Asp Asn Ile Leu Ala Leu Thr Gly Ala Lys Lys Val Asn Leu Ile Gly
65                  70                  75                  80

His Ser His Gly Gly Pro Thr Ala Arg Tyr Ala Ala Ser Ile Ser Pro
                85                  90                  95

Gly Lys Val Ala Ser Val Thr Ser Val Gly Gly Val Asn Trp Gly Ser
            100                 105                 110

Arg Phe Ala Asp Ala Leu Arg Gly Thr Ile Ala Pro Gly Ser Val Ser
        115                 120                 125

Glu Ser Val Ile Gly Ala Ala Ala Asn Ala Phe Ser Ser Ile Ile Glu
    130                 135                 140

Phe Leu Ser Gly Thr Pro Ala Asp Pro Gln Asp Ser Val Ala Ala Leu
145                 150                 155                 160

Asn Ala Leu Thr Thr Ala Gly Ser Leu Ala Phe Asn Ala Ser Tyr Pro
                165                 170                 175

Glu Gly Met Pro Ser Gln Tyr Cys Gly Gln Gly Gln Met Gln Ala Ala
            180                 185                 190

Asn Gly Val Tyr Tyr Phe Ser Trp Ser Gly Ala Ser Pro Leu Thr Asn
        195                 200                 205

Val Leu Asp Val Thr Asp Ala Ala Leu Gly Leu Thr Ser Leu Val Phe
    210                 215                 220

Gly Glu Ser Asn Asp Gly Leu Val Ser Ser Cys Ser Ser His Leu Gly
225                 230                 235                 240

Lys Val Ile Arg Asp Asp Tyr Ala Met Asn His Leu Asp Glu Val Asn
                245                 250                 255

Gln Thr Phe Gly Leu Val Ser Leu Phe Glu Thr Asn Pro Lys Thr Leu
            260                 265                 270

Tyr Arg Asn Gln Ala Asn Arg Leu Lys Asn Leu Gly Leu
        275                 280                 285

<210> SEQ ID NO 3
<211> LENGTH: 271
<212> TYPE: PRT
<213> ORGANISM: Gallaecimonas pentaromativorans
<220> FEATURE:
<221> NAME/KEY: MISC_FEATURE
<222> LOCATION: (1)..(271)
<223> OTHER INFORMATION: Mature peptide sequence 1..271 (of the WT
      Gallaecimonas pentaromativorans chaperone

<400> SEQUENCE: 3

```
Gly Leu Leu Tyr Leu Val Phe Pro Glu Arg His Pro Met Ala Pro Val
1               5                   10                  15
Lys Ala Ala Ala Ser Leu Ala Asp Thr Gln Val Asp Gly Ala Val Gly
            20                  25                  30
Ser Arg Tyr Arg Met Ser Ala Ala Leu Lys Ala Arg Phe Asp Tyr Trp
        35                  40                  45
Leu Ser Ala Val Gly Glu Leu Pro Leu Ser Ala Leu Pro Gly Lys Leu
    50                  55                  60
Ala Gln Ser Leu Arg Gln Asp Gly Trp Ala Glu Ala Asp Ile Asn Ala
65                  70                  75                  80
Ala Leu Ala Ala Phe Ala His Tyr Gln Gln Tyr Leu Asp Ala Leu Ser
                85                  90                  95
Glu Val Ala Lys Pro Gln Ala Ala Ala Ala Glu Leu Lys Ala Ala
            100                 105                 110
Trp Ala Glu Arg Asp Ala Leu Arg Arg Gln Phe Tyr Ala Glu Ala Glu
        115                 120                 125
Ile Lys Leu Leu Trp Gly Asp Glu Ala Ala Val Glu Asp Phe Thr Leu
    130                 135                 140
Arg Arg Leu Glu Ile Gln Ser Leu Gly Leu Ser Gly Glu Gln Leu
145                 150                 155                 160
Lys Trp Glu Glu Asp Ala Leu Ala Gln Ala Pro Ala Thr Val Gln Gln
                165                 170                 175
Ala Tyr Gly Pro Ser Leu Lys Leu Ala Gln Leu Gln Gln Met Asn Gly
            180                 185                 190
Ala Ser Arg Asp Gln Leu Ala Ala Gln Tyr Gly Asp Gly Ala Ala Asp
        195                 200                 205
Arg Leu Met Ala Ala Lys Ala Gln Gln Gln Gly Trp Gln Gly Lys Val
    210                 215                 220
Ala Ala Tyr Arg Asp Lys Val Lys Ser Leu Ala Ala Leu Pro Ser Ala
225                 230                 235                 240
Glu Lys Ala Gln Ala Leu Ala Glu Tyr Gln Ala Arg His Phe Ser Ala
                245                 250                 255
Asn Glu Leu Lys Arg Leu Arg Val Trp Leu Ser Asn Gly Met Gln
            260                 265                 270
```

<210> SEQ ID NO 4
<211> LENGTH: 858
<212> TYPE: DNA
<213> ORGANISM: Artificial
<220> FEATURE:
<223> OTHER INFORMATION: Synthetic gene
<220> FEATURE:
<221> NAME/KEY: misc_feature
<222> LOCATION: (1)..(858)
<223> OTHER INFORMATION: DNA sequence of mature lipase 1..858 bp
<220> FEATURE:
<221> NAME/KEY: misc_feature
<222> LOCATION: (1)..(858)
<223> OTHER INFORMATION: Codon optimized DNA sequence encoding mature
    lipase 1..858 bp

<400> SEQUENCE: 4

```
tcaggttata cccagaccaa atatccgatt gttctggttc atggtctgtt tggttttgat      60
agcctggcag gcgttgatta ttggtatggt attccgcagg cactgagcca ggatggtgca     120
accgtttatg ttgttaatgt tagcgcagca aatagcaccg aagttcgtgg tgaacagctg     180
ctggttcaga ttgataatat tctggcactg accggtgcca aaaaagttaa tctgattggt     240
```

```
catagccatg gtggtccgac cgcacgttat gcagcaagca ttagtccggg taaagttgca    300
agcgttacca gcgttggtgg tgttaattgg ggtagccgtt ttgcagatgc actgcgtggc    360
accattgcac cgggtagcgt tagcgaaagc gttattggtg cagcagcaaa tgcctttagc    420
agcattattg aatttctgag cggtacaccg gcagatccgc aggatagcgt tgcagcactg    480
aatgcactga ccaccgcagg tagcctggcc tttaatgcaa gctatccgga aggtatgccg    540
agccagtatt gtggtcaggg tcagatgcag gcagccaatg tgtttatta ctttagctgg     600 tcaggtgcaa gtccgctgac caatgttctg gatgttaccg atgcagccct gggtctgacc    660
agcctggttt ttggtgaaag caatgatggt ctggttagca gctgtagcag ccatctgggt    720
aaagtgattc gtgatgatta tgcaatgaac cacctggatg aagtgaatca gacctttggc    780
ctggttagcc tgtttgaaac caatccgaaa accctgtatc gtaatcaggc aaatcgtctg    840
aaaaatctgg gtctgtaa                                                 858

<210> SEQ ID NO 5
<211> LENGTH: 816
<212> TYPE: DNA
<213> ORGANISM: Artificial
<220> FEATURE:
<223> OTHER INFORMATION: Synthetic gene
<220> FEATURE:
<221> NAME/KEY: misc_feature
<222> LOCATION: (1)..(816)
<223> OTHER INFORMATION: DNA sequence of mature chaperone 1..816 bp
<220> FEATURE:
<221> NAME/KEY: misc_feature
<222> LOCATION: (1)..(816)
<223> OTHER INFORMATION: Codon optimized DNA sequence encoding mature
      chaperone 1..816 bp

<400> SEQUENCE: 5
ggtctgctgt atctggtttt tccggaacgt catccgatgg caccggttaa agcagcagca     60
agcctggcag atacccaggt tgatggtgca gttggtagcc gttatcgtat gagcgcagca    120
ctgaaagcac gttttgatta ttggctgagc gcagttggtg aactgccgct gagtgcactg    180
cctggtaaac tggcacagag cctgcgtcag gatggttggg ctgaagcaga tattaatgca    240
gcactggcag catttgcaca ttatcagcag tatctggatg cactgagcga agttgcaaaa    300
ccgcaggcag cagcagccgc tgaactgaaa gccgcatggg cagaacgtga tgcactgcgt    360
cgtcagtttt atgcagaagc cgaaattaaa ctgctgtggg gtgatgaagc agcagttgaa    420
gattttaccc tgcgtcgcct ggaaattcag agcctgggtc tgagtgaagg tgaacagctg    480
aaatgggaag aagatgcact ggcccaggca ccggcaaccg ttcagcaggc atatggtccg    540
agcctgaaac tggcgcagct gcagcagatg aatggtgcaa gccgtgatca gctggcagca    600
cagtatggtg atggtccgc agatcgtctg atggcagcaa agcacagca gcagggttgg    660 cagggcaaag ttgcagcata tcgtgataaa gttaaaagtc tggcagccct gccgagcgca    720
gaaaaagcgc aggcactggc cgaatatcag gcacgtcatt ttagcgcaaa cgaactgaaa    780
cgtctgcgtg tgtggctgag caatggtatg cagtaa                            816

<210> SEQ ID NO 6
<211> LENGTH: 1101
<212> TYPE: PRT
<213> ORGANISM: Escherichia coli
<220> FEATURE:
<221> NAME/KEY: MISC_FEATURE
<222> LOCATION: (1)..(1101)
<223> OTHER INFORMATION: DNA sequence encoding the E. coli mature
      maltose binding protein 1..1098 bp
```

<400> SEQUENCE: 6

Ala Ala Ala Ala Thr Cys Gly Ala Ala Gly Ala Ala Gly Gly Thr Ala
1 5 10 15

Ala Ala Cys Thr Gly Gly Thr Ala Ala Thr Cys Thr Gly Gly Ala Thr
20 25 30

Thr Ala Ala Cys Gly Gly Cys Gly Ala Thr Ala Ala Ala Gly Gly Cys
35 40 45

Thr Ala Thr Ala Ala Cys Gly Gly Thr Cys Thr Cys Gly Cys Thr Gly
50 55 60

Ala Ala Gly Thr Cys Gly Gly Thr Ala Ala Gly Ala Ala Ala Thr Thr
65 70 75 80

Cys Gly Ala Gly Ala Ala Ala Gly Ala Thr Ala Cys Cys Gly Gly Ala
85 90 95

Ala Thr Thr Ala Ala Ala Gly Thr Cys Ala Cys Cys Gly Thr Thr Gly
100 105 110

Ala Gly Cys Ala Thr Cys Cys Gly Gly Ala Thr Ala Ala Ala Cys Thr
115 120 125

Gly Gly Ala Ala Gly Ala Gly Ala Ala Ala Thr Thr Cys Cys Cys Ala
130 135 140

Cys Ala Gly Gly Thr Thr Gly Cys Gly Gly Cys Ala Ala Cys Thr Gly
145 150 155 160

Gly Cys Gly Ala Thr Gly Gly Cys Cys Cys Thr Gly Ala Cys Ala Thr
165 170 175

Thr Ala Thr Cys Thr Thr Cys Thr Gly Gly Gly Cys Ala Cys Ala Cys
180 185 190

Gly Ala Cys Cys Gly Cys Thr Thr Thr Gly Gly Thr Gly Gly Cys Thr
195 200 205

Ala Cys Gly Cys Thr Cys Ala Ala Thr Cys Thr Gly Gly Cys Cys Thr
210 215 220

Gly Thr Thr Gly Gly Cys Thr Gly Ala Ala Ala Thr Cys Ala Cys Cys
225 230 235 240

Cys Cys Gly Gly Ala Cys Ala Ala Ala Gly Cys Gly Thr Thr Cys Cys
245 250 255

Ala Gly Gly Ala Cys Ala Ala Gly Cys Thr Gly Thr Ala Thr Cys Cys
260 265 270

Gly Thr Thr Thr Ala Cys Cys Thr Gly Gly Gly Ala Thr Gly Cys Cys
275 280 285

Gly Thr Ala Cys Gly Thr Thr Ala Cys Ala Ala Cys Gly Gly Cys Ala
290 295 300

Ala Gly Cys Thr Gly Ala Thr Thr Gly Cys Thr Thr Ala Cys Cys Cys
305 310 315 320

Gly Ala Thr Cys Gly Cys Thr Gly Thr Thr Gly Ala Ala Gly Cys Gly
325 330 335

Thr Thr Ala Thr Cys Gly Cys Thr Gly Ala Thr Thr Thr Ala Thr Ala
340 345 350

Ala Cys Ala Ala Ala Gly Ala Thr Cys Thr Gly Cys Thr Gly Cys Cys
355 360 365

Gly Ala Ala Cys Cys Cys Gly Cys Cys Ala Ala Ala Ala Ala Cys Cys
370 375 380

Thr Gly Gly Gly Ala Ala Gly Ala Gly Ala Thr Cys Cys Cys Gly Gly
385 390 395 400

Cys Gly Cys Thr Gly Gly Ala Thr Ala Ala Ala Gly Ala Ala Cys Thr
405 410 415

-continued

```
Gly Ala Ala Ala Gly Cys Gly Ala Ala Ala Gly Gly Thr Ala Ala Gly
            420                 425                 430

Ala Gly Cys Gly Cys Gly Cys Thr Gly Ala Thr Gly Thr Thr Cys Ala
        435                 440                 445

Ala Cys Cys Thr Gly Cys Ala Ala Gly Ala Ala Cys Cys Gly Thr Ala
    450                 455                 460

Cys Thr Thr Cys Ala Cys Cys Thr Gly Gly Cys Cys Gly Cys Thr Gly
465                 470                 475                 480

Ala Thr Thr Gly Cys Thr Gly Cys Thr Gly Ala Cys Gly Gly Gly Gly
                485                 490                 495

Gly Thr Thr Ala Thr Gly Cys Gly Thr Thr Cys Ala Ala Gly Thr Ala
            500                 505                 510

Thr Gly Ala Ala Ala Ala Cys Gly Gly Cys Ala Ala Gly Thr Ala Cys
        515                 520                 525

Gly Ala Cys Ala Thr Thr Ala Ala Ala Gly Ala Cys Gly Thr Gly Gly
    530                 535                 540

Gly Cys Gly Thr Gly Gly Ala Thr Ala Ala Cys Gly Cys Thr Gly Gly
545                 550                 555                 560

Cys Gly Cys Gly Ala Ala Ala Gly Cys Gly Gly Gly Thr Cys Thr Gly
                565                 570                 575

Ala Cys Cys Thr Thr Cys Cys Thr Gly Gly Thr Thr Gly Ala Cys Cys
            580                 585                 590

Thr Gly Ala Thr Thr Ala Ala Ala Ala Ala Cys Ala Ala Ala Cys Ala
        595                 600                 605

Cys Ala Thr Gly Ala Ala Thr Gly Cys Ala Gly Ala Cys Ala Cys Cys
    610                 615                 620

Gly Ala Thr Thr Ala Cys Thr Cys Cys Ala Thr Cys Gly Cys Ala Gly
625                 630                 635                 640

Ala Ala Gly Cys Thr Gly Cys Cys Thr Thr Thr Ala Ala Thr Ala Ala
                645                 650                 655

Ala Gly Gly Cys Gly Ala Ala Ala Cys Ala Gly Cys Gly Ala Thr Gly
            660                 665                 670

Ala Cys Cys Ala Thr Cys Ala Ala Cys Gly Gly Cys Cys Cys Gly Thr
        675                 680                 685

Gly Gly Gly Cys Ala Thr Gly Gly Thr Cys Cys Ala Ala Cys Ala Thr
    690                 695                 700

Cys Gly Ala Cys Ala Cys Cys Ala Gly Cys Ala Ala Ala Gly Thr Gly
705                 710                 715                 720

Ala Ala Thr Thr Ala Thr Gly Gly Thr Gly Thr Ala Ala Cys Gly Gly
                725                 730                 735

Thr Ala Cys Thr Gly Cys Cys Gly Ala Cys Cys Thr Thr Cys Ala Ala
            740                 745                 750

Gly Gly Gly Thr Cys Ala Ala Cys Cys Ala Thr Cys Cys Ala Ala Ala
        755                 760                 765

Cys Cys Gly Thr Thr Cys Gly Thr Thr Gly Gly Cys Gly Thr Gly Cys
    770                 775                 780

Thr Gly Ala Gly Cys Gly Cys Ala Gly Gly Thr Ala Thr Thr Ala Ala
785                 790                 795                 800

Cys Gly Cys Cys Gly Cys Cys Ala Gly Thr Cys Cys Gly Ala Ala Cys
                805                 810                 815

Ala Ala Ala Gly Ala Gly Cys Thr Gly Gly Cys Gly Ala Ala Ala Gly
            820                 825                 830
```

```
Ala Gly Thr Thr Cys Cys Thr Cys Gly Ala Ala Ala Ala Cys Thr Ala
            835                 840                 845

Thr Cys Thr Gly Cys Thr Gly Ala Cys Thr Gly Ala Thr Gly Ala Ala
    850                 855                 860

Gly Gly Thr Cys Thr Gly Gly Ala Ala Gly Cys Gly Gly Thr Thr Ala
865                 870                 875                 880

Ala Thr Ala Ala Ala Gly Ala Cys Ala Ala Cys Cys Gly Cys Thr
            885                 890                 895

Gly Gly Gly Thr Gly Cys Cys Gly Thr Ala Gly Cys Gly Cys Thr Gly
            900                 905                 910

Ala Ala Gly Thr Cys Thr Thr Ala Cys Gly Ala Gly Gly Ala Ala Gly
            915                 920                 925

Ala Gly Thr Thr Gly Gly Cys Gly Ala Ala Gly Ala Thr Cys Cys
            930                 935                 940

Ala Cys Gly Thr Ala Thr Thr Gly Cys Cys Gly Cys Ala Cys Cys
945                 950                 955                 960

Ala Thr Gly Gly Ala Ala Ala Cys Gly Cys Cys Cys Ala Gly Ala
            965                 970                 975

Ala Ala Gly Gly Thr Gly Ala Ala Thr Cys Ala Thr Gly Cys Cys
            980                 985                 990

Gly Ala Ala Cys Ala Thr Cys Cys  Cys Gly Cys Ala Gly  Ala Thr Gly
            995                 1000                1005

Thr Cys  Cys Gly Cys Thr Thr  Thr Cys Thr Gly Gly  Thr Ala Thr
    1010                 1015                1020

Gly Cys  Cys Gly Thr Gly Cys  Gly Thr Ala Cys Thr  Gly Cys Gly
    1025                 1030                1035

Gly Thr  Gly Ala Thr Cys Ala  Ala Cys Gly Cys Cys  Gly Cys Cys
    1040                 1045                1050

Ala Gly  Cys Gly Gly Thr Cys  Gly Thr Cys Ala Gly  Ala Cys Thr
    1055                 1060                1065

Gly Thr  Cys Gly Ala Thr Gly  Ala Ala Gly Cys Cys  Cys Thr Gly
    1070                 1075                1080

Ala Ala  Ala Gly Ala Cys Gly  Cys Gly Cys Ala Gly  Ala Cys Thr
    1085                 1090                1095

Thr Ala  Ala
    1100

<210> SEQ ID NO 7
<211> LENGTH: 366
<212> TYPE: PRT
<213> ORGANISM: Escherichia coli
<220> FEATURE:
<221> NAME/KEY: MISC_FEATURE
<222> LOCATION: (1)..(366)
<223> OTHER INFORMATION: Mature peptide sequence 1..366 (of the E. coli
      maltose binding protein)

<400> SEQUENCE: 7

Lys Ile Glu Glu Gly Lys Leu Val Ile Trp Ile Asn Gly Asp Lys Gly
1               5                   10                  15

Tyr Asn Gly Leu Ala Glu Val Gly Lys Lys Phe Glu Lys Asp Thr Gly
            20                  25                  30

Ile Lys Val Thr Val Glu His Pro Asp Lys Leu Glu Glu Lys Phe Pro
        35                  40                  45

Gln Val Ala Ala Thr Gly Asp Gly Pro Asp Ile Ile Phe Trp Ala His
    50                  55                  60
```

Asp Arg Phe Gly Gly Tyr Ala Gln Ser Gly Leu Leu Ala Glu Ile Thr
 65                  70                  75                  80

Pro Asp Lys Ala Phe Gln Asp Lys Leu Tyr Pro Phe Thr Trp Asp Ala
                 85                  90                  95

Val Arg Tyr Asn Gly Lys Leu Ile Ala Tyr Pro Ile Ala Val Glu Ala
            100                 105                 110

Leu Ser Leu Ile Tyr Asn Lys Asp Leu Leu Pro Asn Pro Pro Lys Thr
        115                 120                 125

Trp Glu Glu Ile Pro Ala Leu Asp Lys Glu Leu Lys Ala Lys Gly Lys
130                 135                 140

Ser Ala Leu Met Phe Asn Leu Gln Glu Pro Tyr Phe Thr Trp Pro Leu
145                 150                 155                 160

Ile Ala Ala Asp Gly Gly Tyr Ala Phe Lys Tyr Glu Asn Gly Lys Tyr
                165                 170                 175

Asp Ile Lys Asp Val Gly Val Asp Asn Ala Gly Ala Lys Ala Gly Leu
            180                 185                 190

Thr Phe Leu Val Asp Leu Ile Lys Asn Lys His Met Asn Ala Asp Thr
        195                 200                 205

Asp Tyr Ser Ile Ala Glu Ala Ala Phe Asn Lys Gly Glu Thr Ala Met
210                 215                 220

Thr Ile Asn Gly Pro Trp Ala Trp Ser Asn Ile Asp Thr Ser Lys Val
225                 230                 235                 240

Asn Tyr Gly Val Thr Val Leu Pro Thr Phe Lys Gly Gln Pro Ser Lys
                245                 250                 255

Pro Phe Val Gly Val Leu Ser Ala Gly Ile Asn Ala Ala Ser Pro Asn
            260                 265                 270

Lys Glu Leu Ala Lys Glu Phe Leu Glu Asn Tyr Leu Leu Thr Asp Glu
        275                 280                 285

Gly Leu Glu Ala Val Asn Lys Asp Lys Pro Leu Gly Ala Val Ala Leu
290                 295                 300

Lys Ser Tyr Glu Glu Glu Leu Ala Lys Asp Pro Arg Ile Ala Ala Thr
305                 310                 315                 320

Met Glu Asn Ala Gln Lys Gly Glu Ile Met Pro Asn Ile Pro Gln Met
                325                 330                 335

Ser Ala Phe Trp Tyr Ala Val Arg Thr Ala Val Ile Asn Ala Ala Ser
            340                 345                 350

Gly Arg Gln Thr Val Asp Glu Ala Leu Lys Asp Ala Gln Thr
        355                 360                 365

<210> SEQ ID NO 8
<211> LENGTH: 1986
<212> TYPE: DNA
<213> ORGANISM: Artificial
<220> FEATURE:
<223> OTHER INFORMATION: Synthetic DNA

<400> SEQUENCE: 8
atgaaacatc atcaccatca ccaccctagg aaaatcgaag aagtaaaact ggtaatctgg      60
attaacggcg ataaaggcta taacggtctc gctgaagtcg gtaagaaatt cgagaaagat     120
accggaatta aagtcaccgt tgagcatccg gataaactgg aagagaaatt cccacaggtt     180
gcggcaactg cgatggccc tgacattatc ttctgggcac acgaccgctt tggtggctac     240
gctcaatctg gcctgttggc tgaaatcacc ccggacaaag cgttccagga caagctgtat     300
ccgtttacct gggatgccgt acgttacaac ggcaagctga ttgcttaccc gatcgctgtt     360

-continued

```
gaagcgttat cgctgattta taacaaagat ctgctgccga acccgccaaa aacctgggaa   420
gagatcccgg cgctggataa agaactgaaa gcgaaaggta gagcgcgct gatgttcaac   480 ctgcaagaac cgtacttcac ctggccgctg attgctgctg acggggtta tgcgttcaag   540 tatgaaaacg gcaagtacga cattaaagac gtgggcgtgg ataacgctgg cgcgaaagcg   600
ggtctgacct tcctggttga cctgattaaa aacaaacaca tgaatgcaga caccgattac   660
tccatcgcag aagctgcctt taataaaggc gaaacagcga tgaccatcaa cggcccgtgg   720
gcatggtcca acatcgacac cagcaaagtg aattatggtg taacggtact gccgaccttc   780
aagggtcaac catccaaacc gttcgttggc gtgctgagcg caggtattaa cgccgccagt   840
ccgaacaaag agctggcgaa agagttcctc gaaaactatc tgctgactga tgaaggtctg   900
gaagcggtta ataaagacaa accgctgggt gccgtagcgc tgaagtctta cgaggaagag   960
ttggcgaaag atccacgtat tgccgccacc atggaaaacg cccagaaagg tgaaatcatg  1020
ccgaacatcc gcagatgtc cgctttctgg tatgccgtgc gtactgcggt gatcaacgcc  1080
gccagcggtc gtcagactgt cgatgaagcc ctgaagacg cgcagactaa ttcgagctcg  1140
aacaacaaca acaataacaa taacaacaac ggtctgctgt atctggtttt tccggaacgt  1200
catccgatgg caccggttaa agcagcagca agcctggcag ataccccaggt tgatggtgca  1260 gttggtagcc gttatcgtat gagcgcagca ctgaaagcac gttttgatta ttggctgagc  1320
gcagttggtg aactgccgct gagtgcactg cctggtaaac tggcacagag cctgcgtcag  1380
gatggttggg ctgaagcaga tattaatgca gcactggcag catttgcaca ttatcagcag  1440
tatctggatg cactgagcga agttgcaaaa ccgcaggcag cagcagccgc tgaactgaaa  1500
gccgcatggg cagaacgtga tgcactgcgt cgtcagtttt atgcagaagc cgaaattaaa  1560
ctgctgtggg gtgatgaagc agcagttgaa gattttaccc tgcgtcgcct ggaaattcag  1620
agcctgggtc tgagtgaagg tgaacagctg aaatgggaag aagatgcact ggcccaggca  1680
ccggcaaccg ttcagcaggc atatggtccg agcctgaaac tggcgcagct gcagcagatg  1740
aatggtgcaa gccgtgatca gctggcagca cagtatggtg atggtgccgc agatcgtctg  1800
atggcagcaa agcacagca gcagggttgg cagggcaaag ttgcagcata tcgtgataaa  1860
gttaaaagtc tggcagcccct gccgagcgca gaaaaagcgc aggcactggc cgaatatcag  1920
gcacgtcatt tagcgcaaaa cgaactgaaa cgtctgcgtg tgtggctgag caatggtatg  1980
cagtaa                                                             1986
```

<210> SEQ ID NO 9
<211> LENGTH: 660
<212> TYPE: PRT
<213> ORGANISM: Artificial
<220> FEATURE:
<223> OTHER INFORMATION: Fusion protein

<400> SEQUENCE: 9

Lys His His His His His His Pro Arg Lys Ile Glu Glu Gly Lys Leu
1               5                   10                  15

Val Ile Trp Ile Asn Gly Asp Lys Gly Tyr Asn Gly Leu Ala Glu Val
            20                  25                  30

Gly Lys Lys Phe Glu Lys Asp Thr Gly Ile Lys Val Thr Val Glu His
        35                  40                  45

Pro Asp Lys Leu Glu Glu Lys Phe Pro Gln Val Ala Ala Thr Gly Asp
    50                  55                  60

```
Gly Pro Asp Ile Ile Phe Trp Ala His Asp Arg Phe Gly Gly Tyr Ala
 65                  70                  75                  80

Gln Ser Gly Leu Leu Ala Glu Ile Thr Pro Asp Lys Ala Phe Gln Asp
                 85                  90                  95

Lys Leu Tyr Pro Phe Thr Trp Asp Ala Val Arg Tyr Asn Gly Lys Leu
            100                 105                 110

Ile Ala Tyr Pro Ile Ala Val Glu Ala Leu Ser Leu Ile Tyr Asn Lys
        115                 120                 125

Asp Leu Leu Pro Asn Pro Lys Thr Trp Glu Glu Ile Pro Ala Leu
130                 135                 140

Asp Lys Glu Leu Lys Ala Lys Gly Lys Ser Ala Leu Met Phe Asn Leu
145                 150                 155                 160

Gln Glu Pro Tyr Phe Thr Trp Pro Leu Ile Ala Ala Asp Gly Gly Tyr
                165                 170                 175

Ala Phe Lys Tyr Glu Asn Gly Lys Tyr Asp Ile Lys Asp Val Gly Val
            180                 185                 190

Asp Asn Ala Gly Ala Lys Ala Gly Leu Thr Phe Leu Val Asp Leu Ile
        195                 200                 205

Lys Asn Lys His Met Asn Ala Asp Thr Asp Tyr Ser Ile Ala Glu Ala
210                 215                 220

Ala Phe Asn Lys Gly Glu Thr Ala Met Thr Ile Asn Gly Pro Trp Ala
225                 230                 235                 240

Trp Ser Asn Ile Asp Thr Ser Lys Val Asn Tyr Gly Val Thr Val Leu
                245                 250                 255

Pro Thr Phe Lys Gly Gln Pro Ser Lys Pro Phe Val Gly Val Leu Ser
            260                 265                 270

Ala Gly Ile Asn Ala Ala Ser Pro Asn Lys Glu Leu Ala Lys Glu Phe
        275                 280                 285

Leu Glu Asn Tyr Leu Leu Thr Asp Glu Gly Leu Glu Ala Val Asn Lys
290                 295                 300

Asp Lys Pro Leu Gly Ala Val Ala Leu Lys Ser Tyr Glu Glu Glu Leu
305                 310                 315                 320

Ala Lys Asp Pro Arg Ile Ala Ala Thr Met Glu Asn Ala Gln Lys Gly
                325                 330                 335

Glu Ile Met Pro Asn Ile Pro Gln Met Ser Ala Phe Trp Tyr Ala Val
            340                 345                 350

Arg Thr Ala Val Ile Asn Ala Ala Ser Gly Arg Gln Thr Val Asp Glu
        355                 360                 365

Ala Leu Lys Asp Ala Gln Thr Asn Ser Ser Ser Asn Asn Asn Asn Asn
370                 375                 380

Asn Asn Asn Asn Asn Gly Leu Leu Tyr Leu Val Phe Pro Glu Arg His
385                 390                 395                 400

Pro Met Ala Pro Val Lys Ala Ala Ser Leu Ala Asp Thr Gln Val
                405                 410                 415

Asp Gly Ala Val Gly Ser Arg Tyr Arg Met Ser Ala Ala Leu Lys Ala
            420                 425                 430

Arg Phe Asp Tyr Trp Leu Ser Ala Val Gly Glu Leu Pro Leu Ser Ala
        435                 440                 445

Leu Pro Gly Lys Leu Ala Gln Ser Leu Arg Gln Asp Gly Trp Ala Glu
450                 455                 460

Ala Asp Ile Asn Ala Ala Leu Ala Ala Phe Ala His Tyr Gln Gln Tyr
465                 470                 475                 480
```

Leu Asp Ala Leu Ser Glu Val Ala Lys Pro Gln Ala Ala Ala Ala
                485                 490                 495

Glu Leu Lys Ala Ala Trp Ala Glu Arg Asp Ala Leu Arg Arg Gln Phe
            500                 505                 510

Tyr Ala Glu Ala Glu Ile Lys Leu Leu Trp Gly Asp Glu Ala Ala Val
        515                 520                 525

Glu Asp Phe Thr Leu Arg Arg Leu Glu Ile Gln Ser Leu Gly Leu Ser
    530                 535                 540

Glu Gly Glu Gln Leu Lys Trp Glu Glu Asp Ala Leu Ala Gln Ala Pro
545                 550                 555                 560

Ala Thr Val Gln Gln Ala Tyr Gly Pro Ser Leu Lys Leu Ala Gln Leu
                565                 570                 575

Gln Gln Met Asn Gly Ala Ser Arg Asp Gln Leu Ala Ala Gln Tyr Gly
            580                 585                 590

Asp Gly Ala Ala Asp Arg Leu Met Ala Ala Lys Ala Gln Gln Gln Gly
        595                 600                 605

Trp Gln Gly Lys Val Ala Ala Tyr Arg Asp Lys Val Lys Ser Leu Ala
    610                 615                 620

Ala Leu Pro Ser Ala Glu Lys Ala Gln Ala Leu Ala Glu Tyr Gln Ala
625                 630                 635                 640

Arg His Phe Ser Ala Asn Glu Leu Lys Arg Leu Arg Val Trp Leu Ser
                645                 650                 655

Asn Gly Met Gln
            660

<210> SEQ ID NO 10
<211> LENGTH: 46
<212> TYPE: DNA
<213> ORGANISM: Artificial
<220> FEATURE:
<223> OTHER INFORMATION: Primer

<400> SEQUENCE: 10
aaggagataa acatatgtca ggttataccc agaccaaata tccgat        46

<210> SEQ ID NO 11
<211> LENGTH: 45
<212> TYPE: DNA
<213> ORGANISM: Artificial
<220> FEATURE:
<223> OTHER INFORMATION: Primer

<400> SEQUENCE: 11
ggttagttag aagcttacag acccagattt ttcagacgat ttgcc         45

<210> SEQ ID NO 12
<211> LENGTH: 42
<212> TYPE: DNA
<213> ORGANISM: Artificial
<220> FEATURE:
<223> OTHER INFORMATION: Linker

<400> SEQUENCE: 12
aattcgagct cgaacaacaa caacaataac aataacaaca ac             42

<210> SEQ ID NO 13
<211> LENGTH: 67
<212> TYPE: DNA
<213> ORGANISM: Artificial
<220> FEATURE:
<223> OTHER INFORMATION: Primer

<400> SEQUENCE: 13
aattcgagct cgaacaacaa caacaataac ataacaaca acggtctgct gtatctggtt    60
tttccgg                                                             67

<210> SEQ ID NO 14
<211> LENGTH: 41
<212> TYPE: DNA
<213> ORGANISM: Artificial
<220> FEATURE:
<223> OTHER INFORMATION: Primer

<400> SEQUENCE: 14
tggttagtta gaagcttact gcataccatt gctcagccac a                       41

<210> SEQ ID NO 15
<211> LENGTH: 47
<212> TYPE: DNA
<213> ORGANISM: Artificial
<220> FEATURE:
<223> OTHER INFORMATION: Primer

<400> SEQUENCE: 15
ccatcaccac cctaggaaaa tcgaagaagg taaactggta atctgga                 47

<210> SEQ ID NO 16
<211> LENGTH: 90
<212> TYPE: DNA
<213> ORGANISM: Artificial
<220> FEATURE:
<223> OTHER INFORMATION: Primer

<400> SEQUENCE: 16
gttgttgtta ttgttattgt tgttgttgtt cgagctcgaa ttagtctgcg cgtctttcag    60
ggcttcatcg acagtctgac gaccgctggc                                    90

<210> SEQ ID NO 17
<211> LENGTH: 22
<212> TYPE: DNA
<213> ORGANISM: Artificial
<220> FEATURE:
<223> OTHER INFORMATION: Primer

<400> SEQUENCE: 17
caagctgatt gcttacccga tc                                            22

<210> SEQ ID NO 18
<211> LENGTH: 26
<212> TYPE: DNA
<213> ORGANISM: Artificial
<220> FEATURE:
<223> OTHER INFORMATION: Primer

<400> SEQUENCE: 18
aagagttcct cgaaaactat ctgctg                                        26

<210> SEQ ID NO 19
<211> LENGTH: 23
<212> TYPE: DNA
<213> ORGANISM: Artificial
<220> FEATURE:
<223> OTHER INFORMATION: Primer

<400> SEQUENCE: 19
gcagatatta atgcagcact ggc                                           23

<210> SEQ ID NO 20
<211> LENGTH: 312
<212> TYPE: PRT
<213> ORGANISM: Gallaecimonas xiamenensis

<400> SEQUENCE: 20

| Met | Ser | Leu | Lys | Pro | Leu | Ala | Leu | Gly | Leu | Ala | Leu | Leu | Cys | Ala | Ala |
|---|---|---|---|---|---|---|---|---|---|---|---|---|---|---|---|
| 1 | | | | 5 | | | | | 10 | | | | | 15 | |

Pro Ala Ser Gln Ala Ala Phe Trp His Ser Ser Gly Tyr Thr Gln
        20                  25                  30

Thr His Tyr Pro Ile Val Leu Val His Gly Leu Phe Gly Phe Asp Ser
            35                  40                  45

Leu Ala Gly Val Asp Tyr Trp Tyr Gly Ile Pro Ser Ala Leu Ser Lys
50                  55                  60

Asp Gly Ala Lys Val Tyr Val Val Asn Val Ser Ala Ala Asn Ser Thr
65                  70                  75                  80

Glu Val Arg Gly Glu Gln Leu Leu Ala Gln Ile Asp Asn Ile Leu Ala
                85                  90                  95

Leu Thr Gly Ala Asp Lys Val Asn Leu Ile Gly His Ser His Gly Gly
            100                 105                 110

Pro Thr Ala Arg Tyr Ala Ala Ser Met Ser Pro Asp Lys Val Ala Ser
        115                 120                 125

Val Thr Ser Val Gly Gly Val Asn Trp Gly Ser Ser Phe Ala Asp Ala
130                 135                 140

Val Arg Gly Ala Ile Pro Gln Asp Ser Leu Ser Glu Asp Ile Ile Ala
145                 150                 155                 160

Gly Ala Phe Asn Ala Phe Ala Gly Ile Ile Glu Phe Leu Ser Gly Thr
                165                 170                 175

Pro Ala Asp Pro Gln Asp Ala Val Ala Ala Leu Glu Ser Leu Thr Thr
            180                 185                 190

Ala Gly Thr Leu Ala Phe Asn Ala Arg Tyr Pro Glu Gly Met Pro Ser
        195                 200                 205

Gln Tyr Cys Gly Gln Gly Asp Glu Gln Ala Gly Asn Gly Val Tyr Tyr
210                 215                 220

Tyr Ser Trp Ser Gly Ala Ser Thr Val Thr Asn Val Leu Asp Ile Ser
225                 230                 235                 240

Asp Ala Gly Leu Leu Ala Thr Ser Leu Val Phe Ser Glu Pro Gly Asp
                245                 250                 255

Gly Leu Val Ser Ser Cys Ser Ser His Leu Gly Lys Val Ile Arg Asp
            260                 265                 270

Asn Tyr Gly Met Asn His Leu Asp Glu Val Asn Gln Thr Phe Gly Leu
        275                 280                 285

Val Asn Leu Phe Glu Thr Asn Pro Lys Thr Leu Phe Arg Thr Gln Ala
290                 295                 300

Asn Arg Leu Lys Asn Leu Gly Leu
305                 310

<210> SEQ ID NO 21
<211> LENGTH: 278
<212> TYPE: PRT
<213> ORGANISM: Gallaecimonas xiamenensis

```
<400> SEQUENCE: 21

Met Val Leu Ala Leu Thr Gly Ala Gly Thr Leu Phe Trp Ser Leu Ile
1               5                   10                  15

Gln Ser Pro Lys Gly Pro Ser Ala Pro Val Ala Ser Leu Ala Gly Thr
            20                  25                  30

Gln Thr Asp Gly Ala Leu Gly Pro Gly Phe Val Leu Asp Gly Ala Leu
        35                  40                  45

Lys Asp Arg Phe Asp Tyr Trp Leu Ser Thr Leu Gly Glu Leu Gly Leu
    50                  55                  60

Ala Ala Leu Pro Glu Arg Leu Ala Gln Ser Leu Arg Glu Ala Gly Trp
65                  70                  75                  80

Ser Glu Ala Asp Ile Gly Gln Ala Leu Ala Ala Phe Ala Arg Tyr Gln
                85                  90                  95

Gln Tyr Leu Lys Ala Met Gly Ser Leu Ala Met Pro Ser Arg Ala Ser
            100                 105                 110

Ala Gly Glu Leu Gln Ala Ala Trp Ala Glu Arg Asp Ala Leu Arg Gly
        115                 120                 125

Gln Phe Phe Ser Ala Glu Glu Ile Ala Ala Leu Trp Gly Ala Asp Lys
    130                 135                 140

Gly Leu Glu Glu Leu Thr Leu Arg Arg Leu Glu Ile Gln Ala Leu Asp
145                 150                 155                 160

Leu Asp Pro Gln Ala Arg Gln Asp Trp Leu Asp Asp Glu Leu Ala Lys
                165                 170                 175

Ala Pro Pro Glu Val Gln Arg Ala Leu Gly Pro Ser Gln Arg Leu Ser
            180                 185                 190

Arg Leu Gly Thr Met Glu Gly Ala Ser Arg Asp Gln Leu Ala Ala Glu
        195                 200                 205

Phe Gly Asp Gln Val Ala Asp Arg Leu Glu Gln Val Lys Ala Ala Arg
    210                 215                 220

Gln Asp Trp Gln Gln Arg Val Ala Ala Tyr Arg Ala Glu Ala Glu Arg
225                 230                 235                 240

Leu Gln Gly Leu Pro Gln Ala Glu Arg Gln Glu Ala Leu Ala His Tyr
                245                 250                 255

Gly Asp Gln His Phe Thr Gln Ala Glu Gln Arg Arg Leu Asp Val Trp
            260                 265                 270

Leu Arg His Gln Leu Gln
        275
```